United States Patent
Metchik et al.

(10) Patent No.: US 12,279,982 B2
(45) Date of Patent: Apr. 22, 2025

(54) RETRIEVAL DEVICES FOR HEART VALVE SEALING DEVICES

(71) Applicant: Edwards Lifesciences Corporation, Irvine, CA (US)

(72) Inventors: Asher L. Metchik, Rolling Hills Estates, CA (US); Julia Akiko Roche, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 795 days.

(21) Appl. No.: 17/321,300

(22) Filed: May 14, 2021

(65) Prior Publication Data
US 2021/0267781 A1  Sep. 2, 2021

Related U.S. Application Data

(63) Continuation of application No. PCT/US2019/062391, filed on Nov. 20, 2019.
(Continued)

(51) Int. Cl.
*A61F 2/95* (2013.01)
*A61F 2/24* (2006.01)

(52) U.S. Cl.
CPC .............. *A61F 2/95* (2013.01); *A61F 2/2454* (2013.01); *A61F 2002/9528* (2013.01); *A61F 2220/0016* (2013.01)

(58) Field of Classification Search
CPC .. A61F 2/95; A61F 2002/9511; A61F 2/9522; A61F 2/9524; A61F 2002/9528;
(Continued)

(56) References Cited

U.S. PATENT DOCUMENTS

| 3,874,388 A | 4/1975 | King et al. |
| 4,340,091 A | 7/1982 | Skelton et al. |

(Continued)

FOREIGN PATENT DOCUMENTS

| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Jerrah Edwards
*Assistant Examiner* — Rebecca S Preston
(74) *Attorney, Agent, or Firm* — Anya Adams

(57) ABSTRACT

A retrieval device for retrieving a previously implanted device from a native valve of a patient's heart includes one or more retrieval components. The retrieval components include one or more of a device securing member, a device actuation member, and a clasp capturing member. The securing member is configured to attach the retrieval device to the previously implanted device. The actuation member engages the previously implanted device to move the previously implanted device from a closed configuration to an open configuration. The clasp capturing member is configured to attach to a clasp of the previously implanted device.

9 Claims, 69 Drawing Sheets

Related U.S. Application Data

(60) Provisional application No. 62/808,377, filed on Feb. 21, 2019, provisional application No. 62/770,290, filed on Nov. 21, 2018.

(58) Field of Classification Search
CPC ............ A61F 2002/9534; A61F 2/2454; A61F 2220/0075; A61F 2220/0083
See application file for complete search history.

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,099,534 A * | 8/2000 | Bates .................. A61B 17/221 606/127 |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Galser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Ellasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |

(56) References Cited

U.S. PATENT DOCUMENTS

| | | | |
|---|---|---|---|
| 9,510,837 B2 | 12/2016 | Seguin | |
| 9,510,946 B2 | 12/2016 | Chau et al. | |
| 9,572,660 B2 | 2/2017 | Braido et al. | |
| 9,642,704 B2 | 5/2017 | Tuval et al. | |
| 9,700,445 B2 | 7/2017 | Martin et al. | |
| 9,775,963 B2 | 10/2017 | Miller | |
| D809,139 S | 1/2018 | Marsot et al. | |
| 9,889,002 B2 | 2/2018 | Bonhoeffer et al. | |
| 9,949,824 B2 | 4/2018 | Bonhoeffer et al. | |
| 10,076,327 B2 | 9/2018 | Ellis et al. | |
| 10,076,415 B1 | 9/2018 | Metchik et al. | |
| 10,099,050 B2 | 10/2018 | Chen et al. | |
| 10,105,221 B2 | 10/2018 | Siegel | |
| 10,105,222 B1 | 10/2018 | Metchik et al. | |
| 10,111,751 B1 | 10/2018 | Metchik et al. | |
| 10,123,873 B1 | 11/2018 | Metchik et al. | |
| 10,130,475 B1 | 11/2018 | Metchik et al. | |
| 10,136,993 B1 | 11/2018 | Metchik et al. | |
| 10,159,570 B1 | 12/2018 | Metchik et al. | |
| 10,226,309 B2 | 3/2019 | Ho et al. | |
| 10,231,837 B1 | 3/2019 | Metchik et al. | |
| 10,238,493 B1 | 3/2019 | Metchik et al. | |
| 10,238,494 B2 | 3/2019 | McNiven et al. | |
| 10,238,495 B2 | 3/2019 | Marsot et al. | |
| 10,299,924 B2 | 5/2019 | Kizuka | |
| 10,376,673 B2 | 8/2019 | Van Hoven et al. | |
| 10,575,841 B1 | 3/2020 | Paulos | |
| 2001/0005787 A1 | 6/2001 | Oz et al. | |
| 2002/0013571 A1 | 1/2002 | Goldfarb et al. | |
| 2002/0107531 A1 | 8/2002 | Schreck et al. | |
| 2002/0173811 A1 | 11/2002 | Tu et al. | |
| 2002/0183787 A1 | 12/2002 | Wahr et al. | |
| 2003/0144573 A1 | 7/2003 | Heilman et al. | |
| 2003/0187467 A1 | 10/2003 | Schreck | |
| 2003/0208231 A1 | 11/2003 | Williamson et al. | |
| 2004/0003819 A1* | 1/2004 | St. Goar | A61B 17/122 128/898 |
| 2004/0030382 A1 | 2/2004 | St. Goar et al. | |
| 2004/0034365 A1 | 2/2004 | Lentz et al. | |
| 2004/0044350 A1 | 3/2004 | Martin et al. | |
| 2004/0044365 A1 | 3/2004 | Bachman | |
| 2004/0049207 A1 | 3/2004 | Goldfarb et al. | |
| 2004/0122448 A1 | 6/2004 | Levine | |
| 2004/0127981 A1 | 7/2004 | Rahdert et al. | |
| 2004/0127982 A1 | 7/2004 | Machold et al. | |
| 2004/0147943 A1 | 7/2004 | Kobayashi | |
| 2004/0181135 A1 | 9/2004 | Drysen | |
| 2004/0181206 A1 | 9/2004 | Chiu et al. | |
| 2004/0181238 A1 | 9/2004 | Zarbatany et al. | |
| 2004/0210307 A1 | 10/2004 | Khairkhahan | |
| 2004/0220593 A1 | 11/2004 | Greenhalgh | |
| 2005/0010287 A1 | 1/2005 | Macoviak et al. | |
| 2005/0049618 A1 | 3/2005 | Masuda et al. | |
| 2005/0070926 A1 | 3/2005 | Ortiz | |
| 2005/0137690 A1 | 6/2005 | Salahieh et al. | |
| 2005/0143767 A1 | 6/2005 | Kimura et al. | |
| 2005/0165429 A1 | 7/2005 | Douglas et al. | |
| 2005/0216039 A1 | 9/2005 | Lederman | |
| 2005/0251177 A1 | 11/2005 | Saadat et al. | |
| 2005/0251183 A1 | 11/2005 | Buckman et al. | |
| 2005/0288786 A1 | 12/2005 | Chanduszko | |
| 2006/0020275 A1 | 1/2006 | Goldfarb et al. | |
| 2006/0089671 A1 | 4/2006 | Goldfarb et al. | |
| 2006/0100649 A1 | 5/2006 | Hart | |
| 2006/0122647 A1 | 6/2006 | Callaghan et al. | |
| 2006/0135964 A1 | 6/2006 | Vesely | |
| 2006/0142694 A1 | 6/2006 | Bednarek et al. | |
| 2006/0173251 A1 | 8/2006 | Govari et al. | |
| 2006/0178700 A1 | 8/2006 | Quinn | |
| 2006/0224169 A1 | 10/2006 | Weisenburgh et al. | |
| 2007/0010800 A1 | 1/2007 | Weitzner et al. | |
| 2007/0010877 A1 | 1/2007 | Salahieh et al. | |
| 2007/0016286 A1 | 1/2007 | Herrmann et al. | |
| 2007/0021779 A1 | 1/2007 | Garvin et al. | |
| 2007/0032807 A1 | 2/2007 | Ortiz et al. | |
| 2007/0093857 A1 | 4/2007 | Rogers et al. | |
| 2007/0093890 A1 | 4/2007 | Eliasen et al. | |
| 2007/0156197 A1 | 7/2007 | Root et al. | |
| 2007/0191154 A1 | 8/2007 | Genereux et al. | |
| 2007/0197858 A1 | 8/2007 | Goldfarb et al. | |
| 2007/0198038 A1 | 8/2007 | Cohen et al. | |
| 2007/0265700 A1 | 11/2007 | Ellasen et al. | |
| 2007/0282414 A1 | 12/2007 | Soltis et al. | |
| 2007/0293943 A1 | 12/2007 | Quinn | |
| 2007/0299387 A1 | 12/2007 | Williams et al. | |
| 2007/0299424 A1 | 12/2007 | Cumming et al. | |
| 2008/0039743 A1 | 2/2008 | Fox et al. | |
| 2008/0039953 A1 | 2/2008 | Davis et al. | |
| 2008/0065149 A1 | 3/2008 | Thielen et al. | |
| 2008/0077144 A1 | 3/2008 | Crofford | |
| 2008/0091169 A1 | 4/2008 | Heideman et al. | |
| 2008/0140089 A1 | 6/2008 | Kogiso et al. | |
| 2008/0147093 A1 | 6/2008 | Roskopf et al. | |
| 2008/0147112 A1 | 6/2008 | Sheets et al. | |
| 2008/0149685 A1 | 6/2008 | Smith et al. | |
| 2008/0167713 A1 | 7/2008 | Bolling | |
| 2008/0177300 A1 | 7/2008 | Mas et al. | |
| 2008/0208332 A1 | 8/2008 | Lamphere et al. | |
| 2008/0221672 A1 | 9/2008 | Lamphere et al. | |
| 2008/0255427 A1 | 10/2008 | Satake et al. | |
| 2008/0281411 A1 | 11/2008 | Berreklouw | |
| 2008/0287662 A1 | 11/2008 | Weitzner et al. | |
| 2008/0294247 A1 | 11/2008 | Yang et al. | |
| 2008/0312506 A1 | 12/2008 | Spivey et al. | |
| 2008/0319455 A1 | 12/2008 | Harris et al. | |
| 2009/0005863 A1 | 1/2009 | Goetz et al. | |
| 2009/0024110 A1 | 1/2009 | Heideman et al. | |
| 2009/0131880 A1 | 5/2009 | Speziali et al. | |
| 2009/0156995 A1 | 6/2009 | Martin et al. | |
| 2009/0163934 A1 | 6/2009 | Raschdorf, Jr. et al. | |
| 2009/0166913 A1 | 7/2009 | Guo et al. | |
| 2009/0177266 A1 | 7/2009 | Powell et al. | |
| 2009/0234280 A1 | 9/2009 | Tah et al. | |
| 2009/0275902 A1 | 11/2009 | Heeps et al. | |
| 2009/0287304 A1 | 11/2009 | Dahlgren et al. | |
| 2010/0004739 A1 | 1/2010 | Vesely | |
| 2010/0022823 A1 | 1/2010 | Goldfarb et al. | |
| 2010/0057192 A1 | 3/2010 | Celermajer | |
| 2010/0069834 A1 | 3/2010 | Schultz | |
| 2010/0094317 A1 | 4/2010 | Goldfarb et al. | |
| 2010/0106141 A1 | 4/2010 | Osypka et al. | |
| 2010/0121434 A1 | 5/2010 | Paul et al. | |
| 2010/0249497 A1 | 9/2010 | Peine et al. | |
| 2010/0298929 A1 | 11/2010 | Thornton et al. | |
| 2010/0324595 A1 | 12/2010 | Linder et al. | |
| 2011/0082538 A1 | 4/2011 | Dahlgren et al. | |
| 2011/0137410 A1 | 6/2011 | Hacohen | |
| 2011/0245855 A1 | 10/2011 | Matsuoka et al. | |
| 2011/0257723 A1 | 10/2011 | McNamara | |
| 2011/0295281 A1 | 12/2011 | Mizumoto et al. | |
| 2012/0022633 A1 | 1/2012 | Olson et al. | |
| 2012/0089125 A1 | 4/2012 | Scheibe et al. | |
| 2012/0109160 A1 | 5/2012 | Martinez et al. | |
| 2012/0116419 A1 | 5/2012 | Sigmon, Jr. | |
| 2012/0209318 A1 | 8/2012 | Qadeer | |
| 2012/0277853 A1 | 11/2012 | Rothstein | |
| 2013/0035759 A1 | 2/2013 | Gross et al. | |
| 2013/0041314 A1 | 2/2013 | Dillon | |
| 2013/0066341 A1 | 3/2013 | Ketai et al. | |
| 2013/0066342 A1 | 3/2013 | Dell et al. | |
| 2013/0072945 A1 | 3/2013 | Terada | |
| 2013/0073034 A1 | 3/2013 | Wilson et al. | |
| 2013/0110254 A1 | 5/2013 | Osborne | |
| 2013/0190798 A1 | 7/2013 | Kapadia | |
| 2013/0190861 A1 | 7/2013 | Chau et al. | |
| 2013/0268069 A1 | 10/2013 | Zakai et al. | |
| 2013/0282059 A1 | 10/2013 | Ketai et al. | |
| 2013/0304197 A1 | 11/2013 | Buchbinder et al. | |
| 2013/0325110 A1 | 12/2013 | Khalil et al. | |
| 2014/0031928 A1 | 1/2014 | Murphy et al. | |
| 2014/0046433 A1 | 2/2014 | Kovalsky | |
| 2014/0046434 A1 | 2/2014 | Rolando et al. | |
| 2014/0052237 A1 | 2/2014 | Lane et al. | |
| 2014/0058411 A1 | 2/2014 | Soutorine et al. | |

(56) References Cited

U.S. PATENT DOCUMENTS

| | | |
|---|---|---|
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |

(56) References Cited

U.S. PATENT DOCUMENTS

| | | |
|---|---|---|
| 2021/0259835 A1 | 8/2021 | Tyler et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2014064694 A2 | 5/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faill . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

(56) References Cited

OTHER PUBLICATIONS

Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.

Reul Rm et al., "Mitral valve reconstruction for mitral insufficiency", Prog Cardiovasc Dis., vol. 39, Issue—6, May-Jun. 1997.

Rösch et al., "The Birth, Early Years and Future of Interventional Radiology," Journal of Vascular and Interventional Radiology, vol. 14, No. 7, pp. 841-853, Jul. 1, 2003, Elsevier, United States.

Sabbah et al., "Mechanical Factors in the Degeneration of Porcine Bioprosthetic Valves: an Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation, Ann Thorac Surg., vol. 66, Issue—6, pp. 1640-1646, Nov. 1998.

Urban, Philip MD, "Coronary Artery Stenting", pp. 5-47, © 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob & Smith's Operative Surgery-Cardiac Surgery, vol. 91, No. 2, pp. 415-424, Feb. 1, 1987, Butterworth Scientific, London, UK.

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

\* cited by examiner

RETRIEVAL DEVICES FOR HEART VALVE SEALING DEVICES

RELATED APPLICATIONS

The present application is a continuation of PCT Application No. PCT/US2019/062391, filed Nov. 20, 2019, which claims the benefit of U.S. Provisional Patent Application Ser. No. 62/770,290, filed on Nov. 21, 2018 and U.S. Provisional Patent Application Ser. No. 62/808,377, filed on Feb. 21, 2019. The foregoing applications are incorporated herein by reference in their entirety for all purposes.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In some embodiments, a retrieval device for retrieving a previously implanted device (e.g., one implanted 1-60 minutes or more previously, one implanted 1-24 hours previously, one implanted 1-30 days previously, one implanted a month or more previously, etc.) from a native valve comprises a retrieval shaft for holding one or more retrieval components of the retrieval device. In some embodiments, the retrieval shaft is disposed in a catheter, e.g., within a lumen of a catheter. The retrieval shaft can be moveable inwardly and outwardly relative to the catheter, e.g., the retrieval shaft can be configured to be extended from the catheter.

In some embodiments, the one or more retrieval components comprise a securing member configured to attach the retrieval device to the previously implanted device, and an actuation member or actuation element for engaging the previously implanted device to move or transition the previously implanted device from a closed configuration or attachment configuration (e.g., where the previously implanted device is attached/secured to the native valve) to an open configuration or release configuration (e.g., where the previously implanted device is released from or in a configuration where it can be released from the native valve). The securing member can be the same as or similar to other securing members described anywhere herein. The actuation member or actuation element can be the same as or similar to other actuation members or actuation elements described anywhere herein.

The previously implanted device can include a pair of paddles that are movable between an open position in the open configuration and a closed position in the closed configuration. In some embodiments, the actuation member is configured to engage a cap or other component of the previously implanted device to move the pair of paddles from the closed position to the open position. In some embodiments, the actuation member is configured to engage a coupler of the previously implanted device to move the pair of paddles from the closed position to the open position.

In some embodiments, the previously implanted device includes a pair of gripping clasps that secure the previously implanted device to the native valve. In some embodiments, the retrieval device includes and/or the one or more retrieval components include at least one capturing member for engaging the pair of gripping clasps of the previously implanted device to remove the pair of gripping clasps from the native valve. In some embodiments, the at least one capturing member comprises a first capturing member configured to engage a first gripping clasp of the pair of gripping clasps and a second capturing member configured to engage a second gripping clasp of the pair of gripping clasps. In some embodiments, the at least one capturing member comprises a wire with a loop, and wherein the at least one capturing member is configured to attach to an attachment member of each of the pair of gripping clasps. The attachment member can comprise a hook or any of the other features and/or forms described herein. The at least one capturing member can comprise a hollow shaft or any of the features and/or forms described herein. The securing member can be configured to attach to a collar of the previously implanted device.

In some embodiments, the securing member comprises a first securing portion having a first attachment mechanism configured to attach the first securing portion to the collar and a second securing portion having a second attachment mechanism configured to attach the second securing portion to the collar.

In some embodiments, the first attachment mechanism is a first attachment window and the second attachment mechanism is a second attachment window. In some embodiments, the collar extends through the first attachment window and the second attachment window when the securing member is attached to the collar.

In some embodiments, the one or more retrieval components further comprise a second securing member for attaching the retrieval device to the previously implanted device. In some embodiments, the securing member comprises a wire with a loop that is configured to attach to a collar of the previously implanted device, and wherein the second securing member comprises a hollow shaft that is configured to connect to a shaft of the previously implanted device.

In some embodiments, the one or more retrieval components further comprise a second actuation member that is configured to engage a lock of the previously implanted device to move at least one paddle of the previously implanted device from a locked position to an unlocked position.

In some embodiments, a retrieval device for retrieving a previously implanted device (e.g., one implanted 1-60 minutes or more previously, one implanted 1-24 hours previously, one implanted 1-30 days previously, one implanted a month or more previously, etc.) from a native valve comprises a retrieval shaft for holding one or more retrieval components of the retrieval device. In some embodiments, the retrieval shaft is disposed within a catheter and is configured to be extendable from the catheter.

In some embodiments, the one or more retrieval components comprise an actuation element or actuation member for engaging the previously implanted device to move the previously implanted device from a closed configuration to an open configuration.

In some embodiments, the one or more retrieval components comprise a securing member configured to attach the retrieval device to the previously implanted device, e.g., to a collar of the previously implanted device, etc.

In some embodiments, the one or more retrieval components comprise a first capturing member for engaging a first gripping clasp of the previously implanted device to remove the first gripping clasp from the native valve. In some embodiments, the one or more retrieval components comprise a second capturing member for engaging a second gripping clasp of the previously implanted device to remove the second gripping clasp from the native valve.

The previously implanted device can be configured with a pair of paddles that are movable between an open position in the open configuration and a closed position in the closed configuration. In some embodiments, the actuation element is configured to engage and move a cap or other component of the previously implanted device to move the pair of paddles from the closed position to the open position.

In some embodiments, the securing member is configured to position the retrieval device relative to the previously implanted device such that the actuation element is positioned to engage the previously implanted device to move the previously implanted device from the closed configuration to the open configuration.

In some embodiments, the first capturing member comprises a wire with a loop. In some embodiments, the first capturing member is configured to connect to an attachment member of the first gripping clasp. In some embodiments, the attachment member comprises a hook.

The previously implanted device can be configured with a shaft, a coupler movably attached to the shaft for moving the previously implanted device between the open configuration and the closed configuration, and a lock for moving the coupler between a locked position and an unlocked position. In some embodiments, the actuation element comprises a first actuation element for engaging the coupler of the previously implanted device to move the previously implanted device from the closed configuration to the open configuration, and a second actuation element for engaging the lock of the previously implanted device to move the coupler from the locked position to the unlocked position.

In some embodiments, a method of retrieving a previously implanted valve repair device from a native valve (e.g., a native valve of a live patient or a simulated patient, etc.) with a retrieval device comprises securing the retrieval device to the previously implanted valve repair device. The method includes engaging the previously implanted valve repair device with an actuation element or actuation member of the retrieval device to move the previously implanted valve repair device from a closed configuration or attachment configuration (e.g., where the previously implanted device is attached/secured to the native valve) to an open configuration or release configuration (e.g., where the previously implanted device is released from or in a configuration where it can be released from the native valve). The method further includes removing the retrieval device and the previously implanted valve repair device away from the native valve.

In some embodiments, the method further comprises engaging a pair of gripping clasps of the previously implanted valve repair device with one or more capturing members of the retrieval device to remove the pair of gripping clasps from the native valve. In some embodiments, a first gripping clasp of the pair of gripping clasps is engaged with a first capturing member of the one or more capturing members, and a second gripping clasp of the pair of gripping clasps is engaged with a second capturing member of the one or more capturing members.

In some embodiments, the method further comprises positioning the retrieval device relative to the previously implanted valve repair device at the native valve such that the retrieval device is capable of engaging the previously implanted valve repair device.

In some embodiments, the method further comprises securing the retrieval device to the previously implanted valve repair device with a securing member.

In some embodiments, the method further comprises engaging a lock of the previously implanted valve repair device with a second actuation element to move the previously implanted valve repair device from a locked position to an unlocked position such that the previously implanted valve repair device can be move from the closed configuration to the open configuration.

In some embodiments, a retrieval device for retrieving a previously implanted device from a native valve of a patient's heart includes a catheter and a retrieval shaft that holds one or more retrieval components. The retrieval shaft can be disposed within and configured to be extended from the catheter. The retrieval components include at least one capturing member and a securing member. The securing member is configured to attach the retrieval device to the previously implanted device. The capturing members engage one or more gripping clasps of the previously implanted device to remove the previously implanted device from the native valve.

An example retrieval device for retrieving a previously implanted device from a native valve of a patient's heart includes a catheter and a retrieval shaft that holds one or more retrieval components. The retrieval shaft is disposed within and configured to be extended from the catheter. In some embodiments, the retrieval components include an actuation member or actuation element, a securing member, and at least one capturing member. In some embodiments, the actuation member engages a pair of paddles of the previously implanted device to move the pair of paddles from a closed position to an open position. In some embodiments, the securing member is configured to attach the retrieval device to the previously implanted device, and the at least one capturing member engages a pair of gripping clasps of the previously implanted device to remove the gripping clasps from the native valve.

In some embodiments, an example retrieval device for retrieving a previously implanted device from a native valve of a patient's heart includes a catheter and a retrieval shaft that holds one or more retrieval components. The retrieval shaft is disposed within and configured to be extended from the catheter. The one or more retrieval components include an actuation member or actuation element, a securing member, and first and second capturing members. In some embodiments, the actuation member engages a pair of paddles of the previously implanted device to move the paddles from a closed position to an open position. In some embodiments, the securing member is configured to attach the retrieval device to a collar of the previously implanted device. In some embodiments, the first capturing member engages a first gripping clasp of the previously implanted device to remove the first gripping clasp from the native valve, and the second capturing member engages a second gripping member of the previously implanted device to remove the second gripping clasp from the native valve.

In some embodiments, an example retrieval device for retrieving a previously implanted device from a native valve of a patient's heart includes a catheter and a retrieval shaft that holds one or more retrieval components. The retrieval shaft is disposed within and configured to be extended from the catheter. In some embodiments, the one or more retrieval components include first and second securing members, first and second actuation members or elements, and first and second capturing members. In some embodiments, the first securing member is configured to attach the retrieval device to a collar of the previously implanted device, and the second securing member is configured to attach the retrieval device to a shaft of the previously implanted device. In some embodiments, the first actuation member engages a coupler of the previously implanted device to move a pair of paddles of the previously implanted device from a closed position to an open position, and the second actuation member engages a lock of the previously implanted device to move the coupler of the previously implanted device from a locked position to an unlocked position. In some embodiments, the first capturing member engages a first gripping clasp of the previously implanted device to remove the first gripping clasp from the native valve, and the second capturing member engages a second gripping member of the previously implanted device to remove the second gripping clasp from the native valve.

An example method of retrieving a previously implanted valve repair device from a native valve of a patient with a retrieval device includes securing the retrieval device to the collar of the previously implanted valve repair device. In some embodiments, the method also includes engaging the previously implanted valve repair device with an actuation member or actuation element of the retrieval device to move a pair of paddles of the previously implanted valve repair device from a closed position to an open position. In some embodiments, the method includes engaging a pair of gripping clasps of the previously implanted valve repair device with one or more capturing members of the retrieval device to remove the gripping clasps from the native valve. In some embodiments, the method also includes removing the retrieval device and the previously implanted valve repair device from the patient. This method can be performed on a living animal or on a simulation, such as on a cadaver, cadaver heart, simulator (e.g. with the body parts, heart, tissue, etc. being simulated), etc.

In some embodiments, an example retrieval device for retrieving a previously implanted device from a native valve of a patient's heart includes a catheter and a retrieval shaft that holds one or more retrieval components. In some embodiments, the retrieval shaft is disposed within and configured to be extended from the catheter. In some embodiments, the retrieval components include a securing member, a first capturing member, and a second capturing member. In some embodiments, the securing member is configured to attach the retrieval device to the previously implanted device, and the first and second capturing members have a barb for engaging and attaching to a pair of gripping clasps of the previously implanted device to remove the gripping clasps from the native valve.

In some embodiments, an example method of retrieving a previously implanted valve repair device from a native valve of a patient with a retrieval device includes securing the retrieval device to the collar of the previously implanted valve repair device. In some embodiments, the method also includes engaging a pair of gripping clasps of the previously implanted valve repair device with at least one capturing member of the retrieval device to remove the pair of gripping clasps from the native valve of the patient. In some embodiments, the method includes removing the retrieval device and the previously implanted valve repair device from the patient. This method can be performed on a living animal or on a simulation, such as on a cadaver, cadaver heart, simulator (e.g. with the body parts, heart, tissue, etc. being simulated), etc.

In some embodiments, an example method of retrieving a previously implanted valve repair device from a native valve of a patient with a retrieval device includes securing the retrieval device to the collar of the previously implanted valve repair device. In some embodiments, the method also includes engaging the previously implanted valve repair device with an actuation member or actuation element of the retrieval device to move a pair of paddles of the previously implanted device from a closed position to an open position. In some embodiments, the method includes rapidly moving the previously implanted device after the pair of paddles are moved from the closed position to the open position such that a pair of gripping clasps of the previously implanted valve repair device are removed from the native valve of the patient. In some embodiments, the method also includes removing the retrieval device and the previously implanted valve repair device from the patient. This method can be performed on a living animal or on a simulation, such as on a cadaver, cadaver heart, simulator (e.g. with the body parts, heart, tissue, etc. being simulated), etc.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

The following description refers to the accompanying drawings, which illustrate specific embodiments of the present disclosure. Other embodiments having different structures and operation do not depart from the scope of the present disclosure.

Example embodiments of the present disclosure are directed to devices and methods for repairing a defective heart valve. It should be noted that various embodiments of native valve repair devices, systems for delivery of native valve repair devices, and systems for removal of implanted native valve repair devices are disclosed herein, and any combination of these options can be made unless specifically excluded. In other words, individual components of the disclosed devices and systems can be combined unless mutually exclusive or otherwise physically impossible. The methods and steps shown and/or discussed can be performed on a living animal or on a simulation, such as on a cadaver, cadaver heart, simulator (e.g. with the body parts, heart, tissue, etc. being simulated), etc.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

Figure 1:
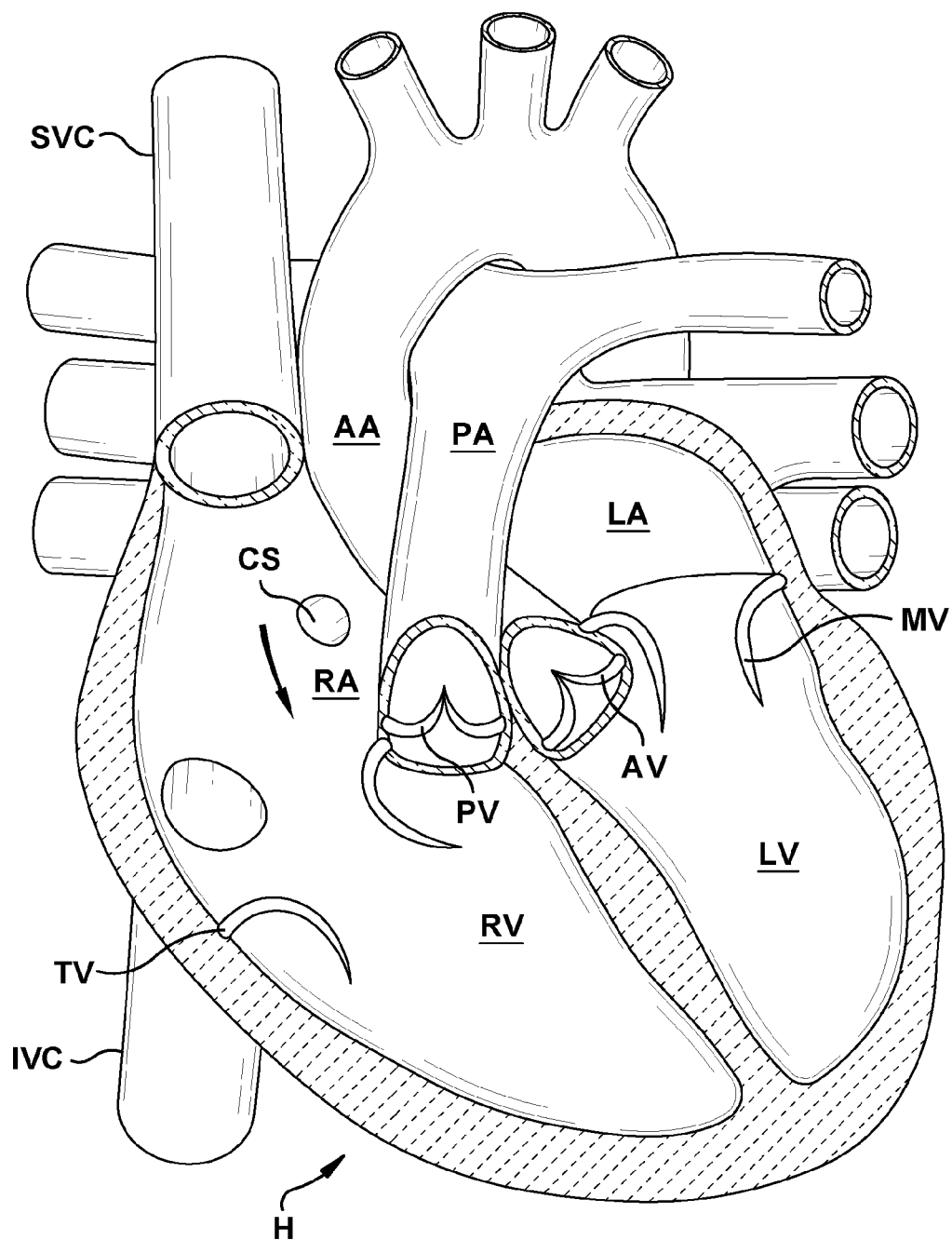
FIG. 1 illustrates a cutaway view of the human heart in a diastolic phase.
Figure 2:
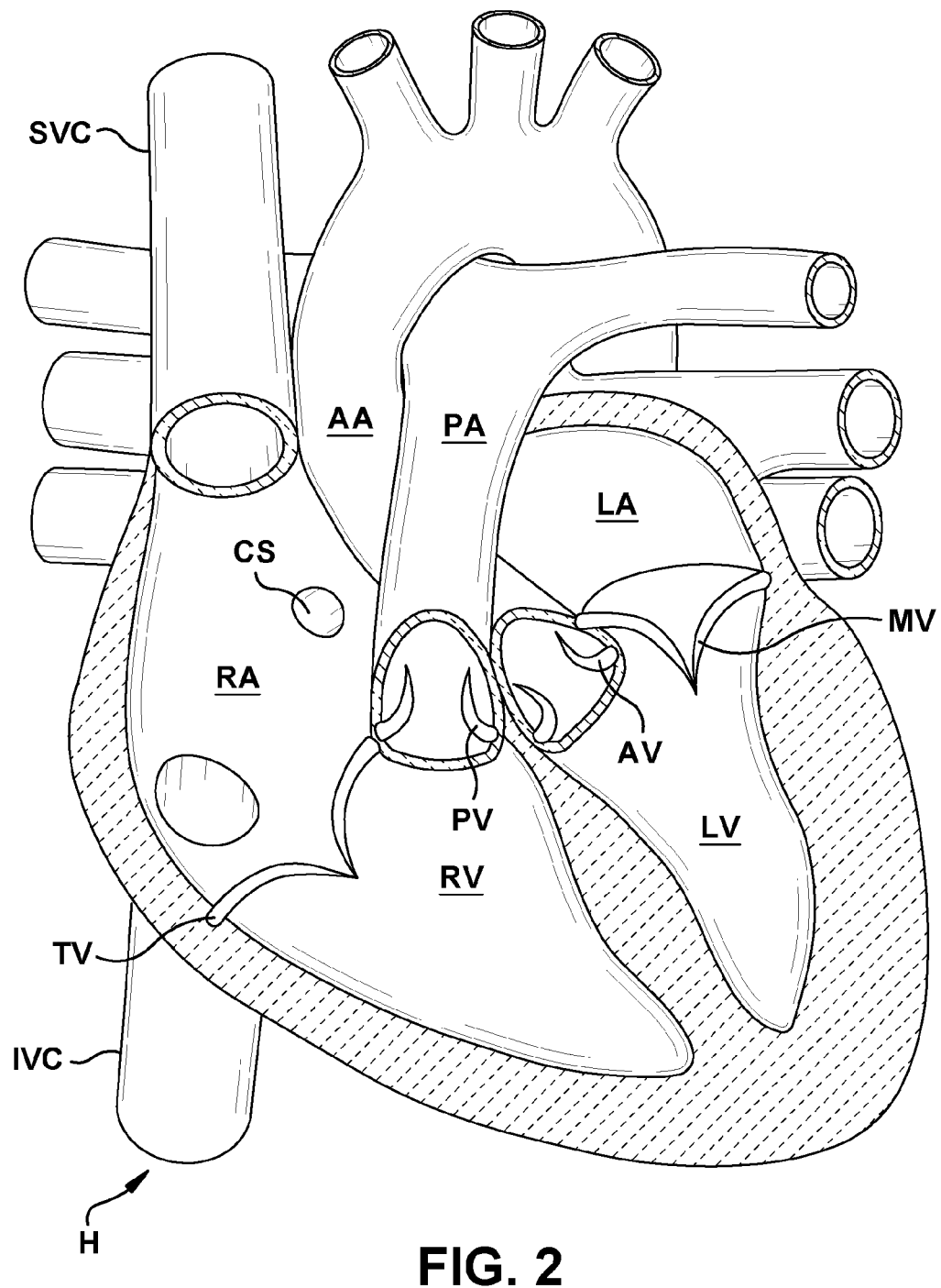
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flowstream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one example embodiment, the devices described by the present application are used to repair the function of a defective mitral valve MV. That is, the devices are configured to help close the leaflets of the mitral valve to prevent blood from regurgitating from the left ventricle LV and back into the left atrium LA.

Figure 3:
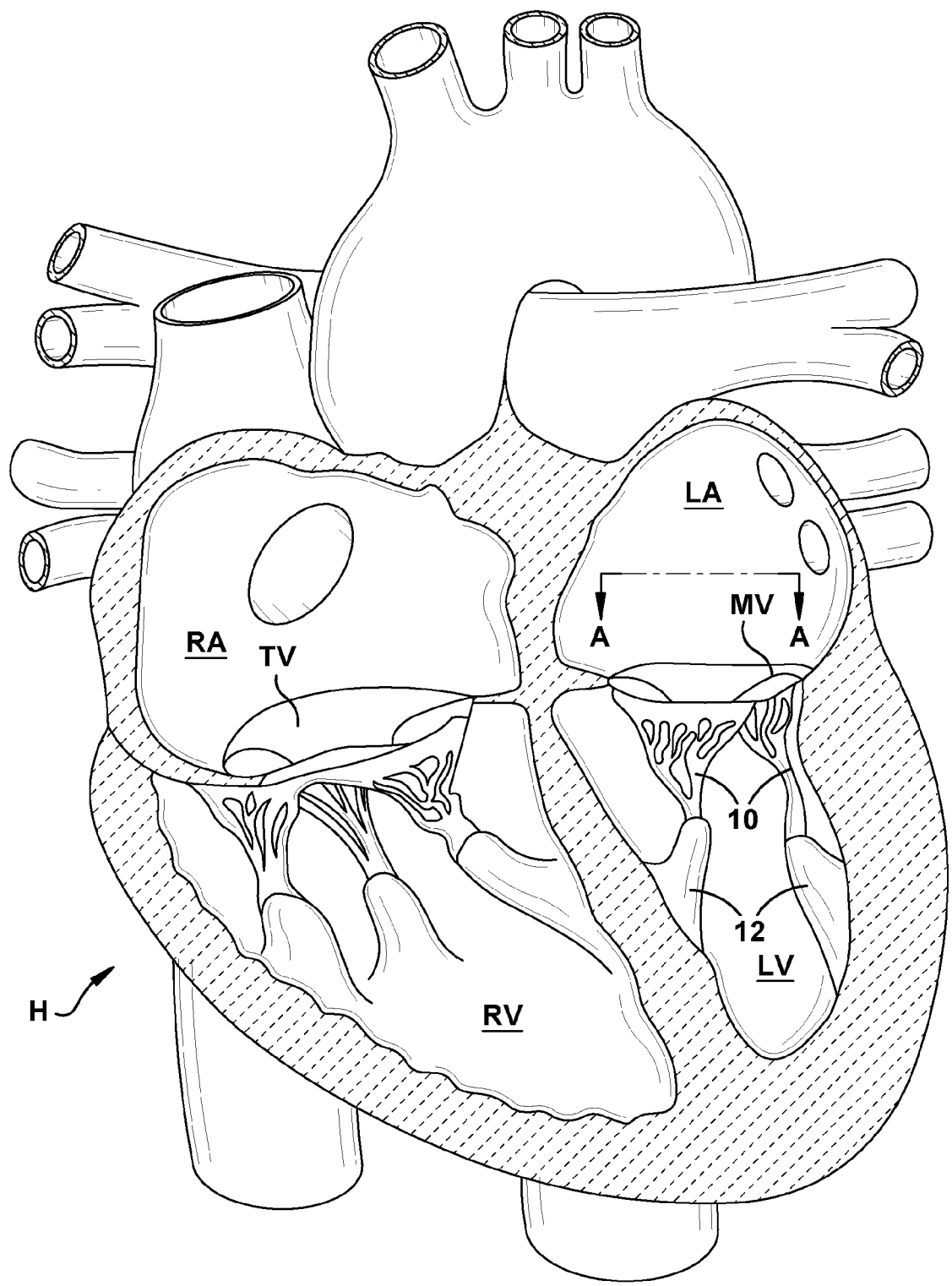
FIG. 3 illustrates a cutaway view of the human heart in a diastolic phase, in which the chordae tendineae are shown attaching the leaflets of the mitral and tricuspid valves to ventricle walls.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordac tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three main mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (IIIb).

Figure 4:
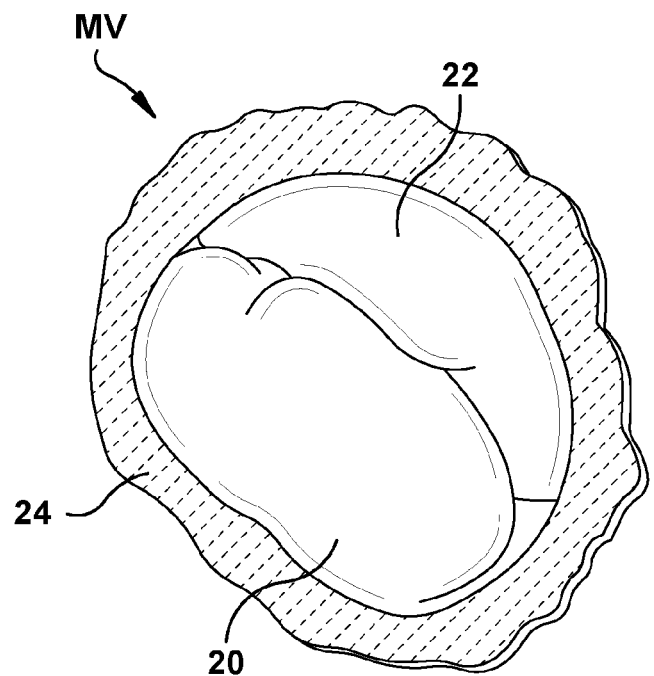
FIG. 4 illustrates a healthy mitral valve with the leaflets closed as viewed from an atrial side of the mitral valve.
Figure 5:
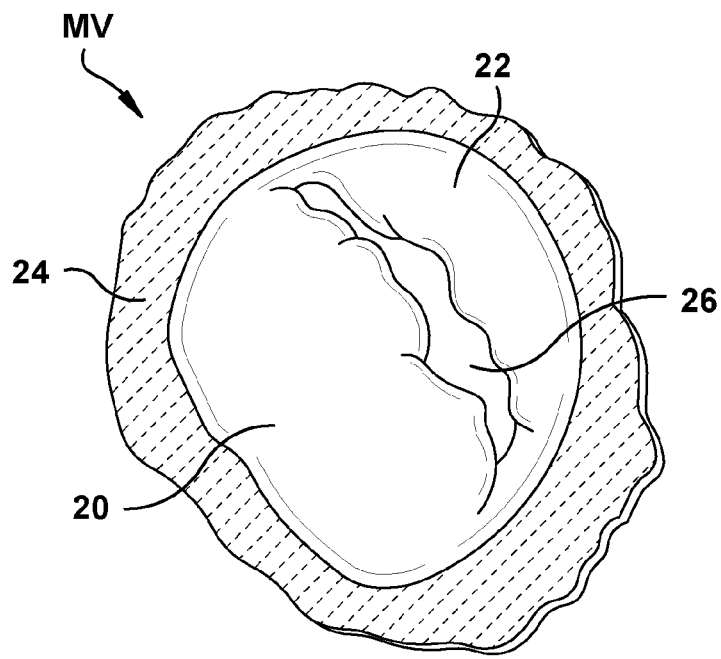
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
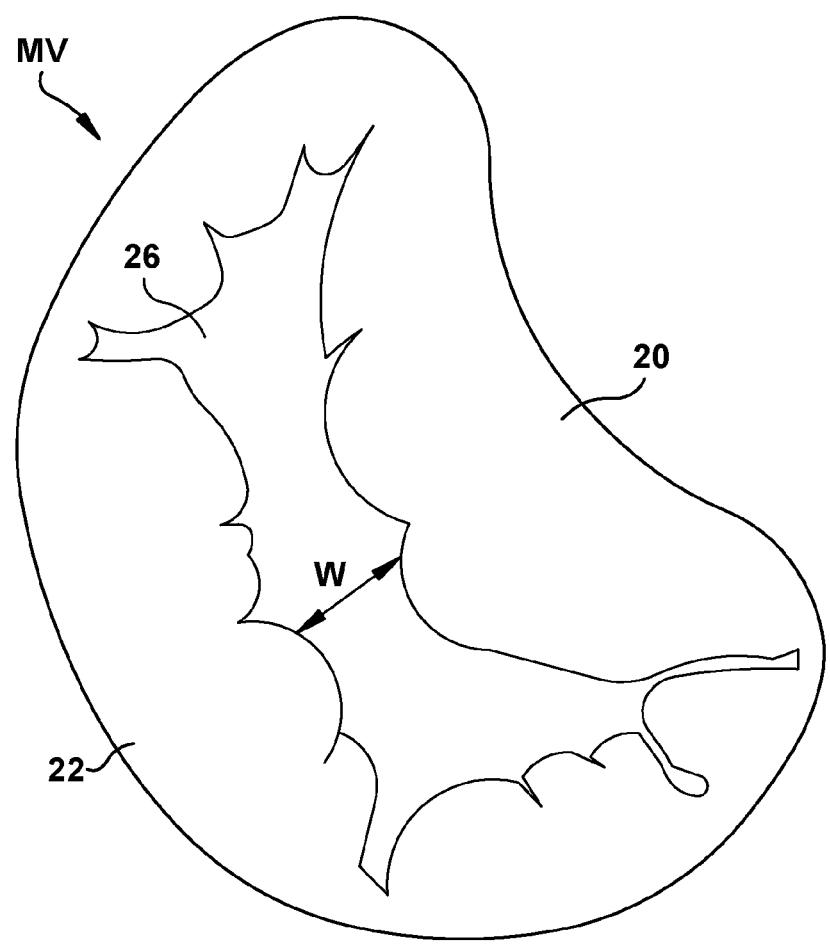
FIG. 6 illustrates a mitral valve having a wide gap between the posterior leaflet and the anterior leaflet.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordac tendineae 10 becoming dysfunctional (e.g., the chordae tendineae may stretch or rupture), which allows the anterior leaflet 20 and the posterior leaflet 22 to be reverted such that blood is regurgitated into the left atrium LA. The problems occurring due to dysfunctional chordac tendineae can be repaired by repairing the chordae tendineae or the structure of the mitral valve (e.g., by securing the leaflets 20, 22 at the affected portion of the mitral valve).

Figure 7:
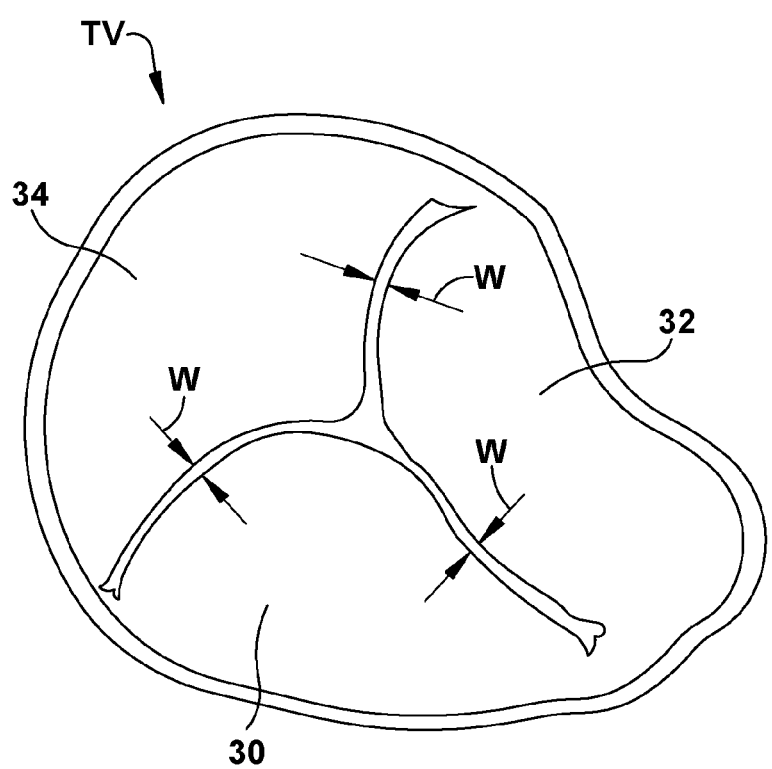
FIG. 7 illustrates a tricuspid valve viewed from an atrial side of the tricuspid valve.

The devices and procedures disclosed herein make reference to repairing the structure of a mitral valve or removing an implanted repair device from the mitral valve. However, it should be understood that the devices and concepts provided herein can be used to repair any native valve or any component of a native valve or can be used to remove an implanted repair device from any native valve. Referring now to FIG. 7, any of the devices and concepts provided herein can be used to repair the tricuspid valve TV or remove an implanted repair device from the tricuspid valve. For example, the devices and concepts provided herein can be used between any two of the anterior leaflet 30, septal leaflet 32, and posterior leaflet 34 to prevent regurgitation of blood from the right ventricle into the right atrium, and the devices and concepts can be used to remove an implanted repair device from between any two of the anterior leaflet 30, septal leaflet 32, and posterior leaflet 34. In addition, any of the devices and concepts provided herein can be used on all three of the leaflets 30, 32, 34 together to prevent regurgitation of blood from the right ventricle to the right atrium, or to remove a repair device from between all three leaflets 30, 32, 34 of the tricuspid valve. That is, the valve repair devices provided herein can be centrally located between the three leaflets 30, 32, 34.

An example implantable prosthetic device can have a coaption element or coaptation element and at least one anchor. The coaption element is configured to be positioned within the native heart valve orifice to help fill the space and form a more effective seal, thereby reducing or preventing regurgitation described above. The coaption element can have a structure that is impervious to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element can have various shapes. In some embodiments, the coaption element can have an elongated cylindrical shape having a round cross-sectional shape. In other embodiments, the coaption element can have an oval cross-sectional shape, a crescent cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native mitral leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native valve leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular portion of the coaption element. In some embodiments, the anchor can attach to an actuation element (e.g., a shaft, actuation wire, rod, tether, suture, line, etc.), to which the coaption element is also attached. In some embodiments, the anchor and the coaption element can be positioned independently with respect to each other by separately moving each of the anchor and the coaption element along the longitudinal axis of the actuation element. In some embodiments, the anchor and the coaption element can be positioned simultaneously by moving the anchor and the coaption element together along the longitudinal axis of the actuation element. The anchor can be configured to be positioned behind a native leaflet when implanted such that the leaflet is grasped by the anchor.

The prosthetic device can be configured to be implanted via a delivery sheath. The coaption element and the anchor can be compressible to a radially compressed state and can be self-expandable to a radially expanded state when compressive pressure is released. The device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are optionally configured to self-expand. The implantation methods for various embodiments can be different and are more fully discussed below with respect to each embodiment. Additional information regarding these and other delivery methods can be found in U.S. Pat. No. 8,449,599 and U.S. Patent Application Publication Nos. 2014/0222136, 2014/0067052, 2016/0331523, each of which is incorporated herein by reference in its entirety. The methods and steps shown and/or discussed can be performed on a living animal or on a simulation, such as on a cadaver, cadaver heart, simulator (e.g. with the body parts, heart, tissue, etc. being simulated), etc.

The disclosed prosthetic devices can be configured such that the anchor is connected to a leaflet, taking advantage of the tension from native chordae tendineae to resist high systolic pressure urging the device toward the left atrium. During diastole, the devices can rely on the compressive and retention forces exerted on the leaflet that is grasped by the anchor.

Referring now to FIGS. 8-14, a schematically illustrated implantable prosthetic device 100 is shown in various stages of deployment. The prosthetic device 100 and associated systems, methods, etc. are described in more detail in International Application Nos. PCT/US2018/028189 and PCT/US2019/055320, which are incorporated herein by reference in its entirety. The device 100 can include any other features for an implantable prosthetic device discussed in the present application, and the device 100 can be positioned to engage valve tissue (e.g., leaflets 20, 22) as part of any suitable valve repair system (e.g., any valve repair system disclosed in the present application).

The device 100 is deployed from a delivery sheath 102 and includes a coaption portion 104 and an anchor portion 106. The coaption portion 104 of the device 100 includes a coaption element 110 that is adapted to be implanted between the leaflets of the native valve (e.g., native mitral valve, native tricuspid valve, etc.) and is slidably attached to an actuation member or actuation element 112 (e.g., a wire, shaft, rod, line, suture, tether, etc.). The anchor portion 106 is actuatable between open and closed conditions and can take a wide variety of forms, such as, for example, paddles, gripping elements, or the like. Actuation of the actuation element 112 opens and closes the anchor portion 106 of the device 100 to grasp the native valve leaflets during implantation. The actuation element 112 may take a wide variety of different forms. For example, the actuation element may be threaded such that rotation of the actuation element moves the anchor portion 106 relative to the coaption portion 104. Or, the actuation element may be unthreaded, such that pushing or pulling the actuation element 112 moves the anchor portion 106 relative to the coaption portion 104.

The anchor portion 106 of the device 100 includes outer paddles 120 and inner paddles 122 that are connected between a cap 114 and the coaption element 110 by portions 124, 126, 128. The portions 124, 126, 128 can be jointed and/or flexible to move between all of the positions described below. The interconnection of the outer paddles 120, the inner paddles 122, the coaption element 110, and the cap 114 by the portions 124, 126, and 128 can constrain the device to the positions and movements illustrated herein.

The actuation member or actuation element 112 extends through the delivery sheath and the coaption element 110 to the cap 114 at the distal connection of the anchor portion 106. Extending and retracting the actuation element 112 increases and decreases the spacing between the coaption element 110 and the cap 114, respectively. A collar 115 removably attaches the coaption element 110 to the delivery sheath 102 so that the actuation element 112 slides through the collar 115 and coaption element 110 during actuation to open and close the paddles 120, 122 of the anchor portion 106. After the device 100 is connected to valve tissue, if the device 100 needs to be removed from the valve tissue, a retrieval device 2200 (see FIGS. 24-34 and 36-38) can be used to connect to the collar 115 such that the actuation element can extend through the collar 115 and the coaption element 110 to engage the anchor portion 106 to open the paddles 120, 122 and remove the device 100 from the valve tissue (as discussed herein with reference to FIGS. 24-34 and 36-38).

Figure 11:
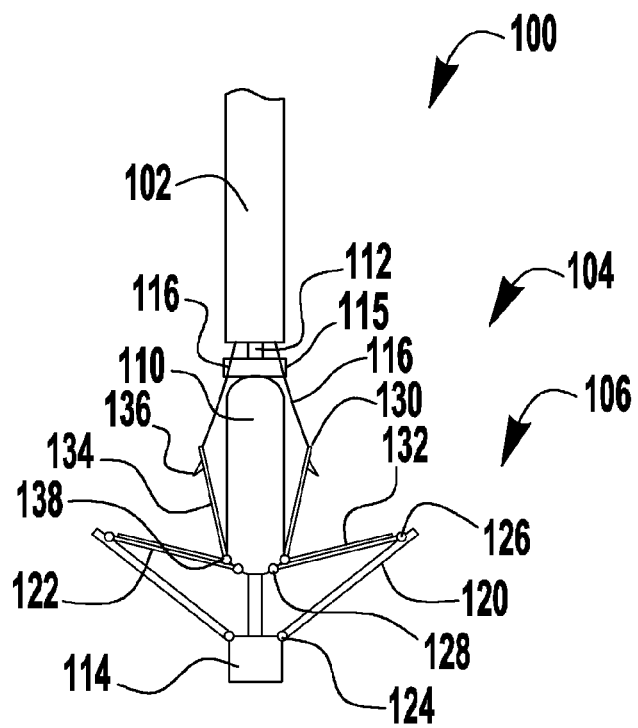

Referring now to FIG. 11, the anchor portion 106 includes attachment portions or gripping members (e.g., clasps, grippers, paddles, clamps, clips, fasteners, staples, etc.). The illustrated gripping members are barbed clasps 130 that include a base or fixed arm 132, a moveable arm 134, barbs 136, and a joint portion 138. The fixed arms 132 are attached to the inner paddles 122, with the joint portion 138 disposed proximate the coaption element 110. The barbed clasps have flat surfaces and do not fit in a recess of the paddle. Rather, the flat portions of the barbed clasps 130 are disposed against the surface of the inner paddle 122. The joint portion 138 provides a spring force between the fixed and moveable arms 132, 134 of the barbed clasp 130. The joint portion 138 can be any suitable joint, such as a flexible joint, a spring joint, a pivot joint, or the like. In certain embodiments, the joint portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the barbed clasps 130 and expose the barbs 136. The barbed clasps 130 are opened by applying tension to actuation lines 116 attached to the moveable arms 134, thereby causing the moveable arms 134 to pivot on the joint portions 138.

During implantation, the paddles 120, 122 are opened and closed to grasp the native valve leaflets between the paddles 120, 122 and the coaption element 110. The barbed clasps 130 further secure the native leaflets by engaging the leaflets with barbs 136 and pinching the leaflets between the moveable and fixed arms 134, 132. The barbs 136 of the barbed clasps 130 increase friction with the leaflets or may partially or completely puncture the leaflets. The actuation lines 116 can be actuated separately so that each barbed clasp 130 can be opened and closed separately. Separate operation allows one leaflet to be grasped at a time, or for the repositioning of a clasp 130 on a leaflet that was insufficiently grasped, without altering a successful grasp on the other leaflet. The barbed clasps 130 can be opened and closed relative to the position of the inner paddle 122 (as long as the inner paddle is in an open position), thereby allowing leaflets to be grasped in a variety of positions as the particular situation requires.

The barbed clasps 130 can be opened separately by pulling on an attached actuation line 116 that extends through the delivery sheath 102 to the barbed clasp 130. The actuation line 116 can take a wide variety of forms, such as, for example, a line, a suture, a wire, a tether, a rod, a catheter, or the like. The barbed clasps 130 can be spring loaded so that in the closed position the barbed clasps 130 continue to provide a pinching force on the grasped native leaflet. This pinching force can remain constant or positive regardless of the position of the inner paddles 122. Barbs 136 of the barbed clasps 130 can pierce the native leaflets to further secure the native leaflets.

Figure 8:
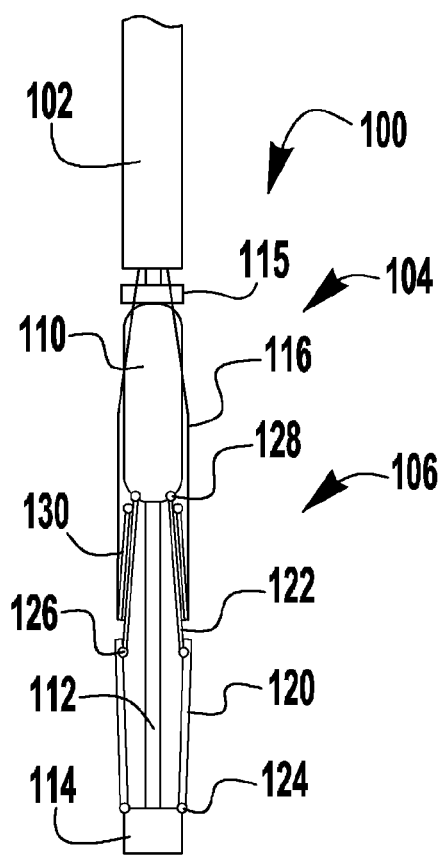
FIGS. 8-14 show an example embodiment of an implantable prosthetic device, in various stages of deployment.

Referring now to FIG. 8, the device 100 is shown in an elongated or fully open condition for deployment from the delivery sheath. The device 100 is loaded in the delivery sheath in the fully open position, because the fully open position takes up the least space and allows the smallest catheter to be used (or the largest implantable device 100 to be used for a given catheter size). In the elongated condition the cap 114 is spaced apart from the coaption element 110 such that the paddles 120, 122 of the anchor portion 106 are fully extended. In some embodiments, an angle formed between the interior of the outer and inner paddles 120, 122 is approximately 180 degrees. The barbed clasps 130 are kept in a closed condition during deployment through the delivery sheath 102 so that the barbs 136 (FIG. 11) do not catch or damage the sheath or tissue in the patient's heart.

Figure 9:
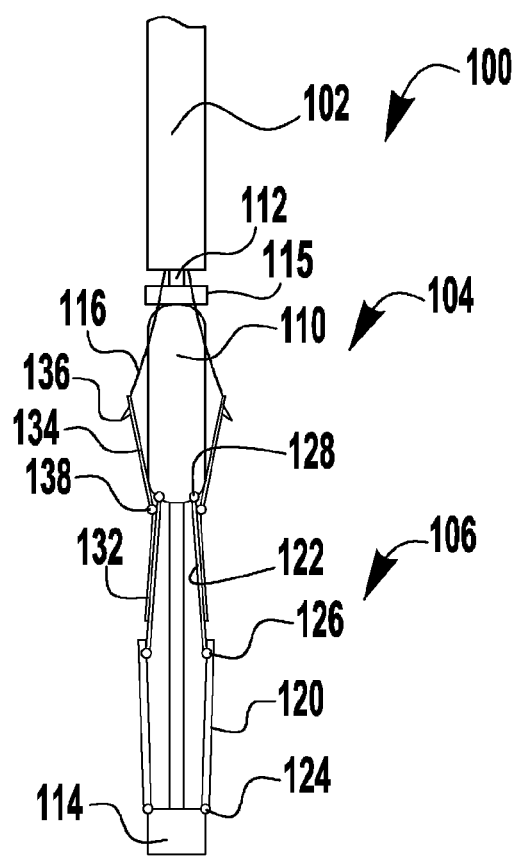

Referring now to FIG. 9, the device 100 is shown in an elongated detangling condition, similar to FIG. 8, but with the barbed clasps 130 in a fully open position, ranging from about 140 degrees to about 200 degrees, to about 170 degrees to about 190 degrees, or about 180 degrees between fixed and moveable portions of the barbed clasps 130. Fully opening the paddles 120, 122 and the clasps 130 has been found to improve ease of detanglement from anatomy of the patient during implantation of the device 100.

Figure 10:
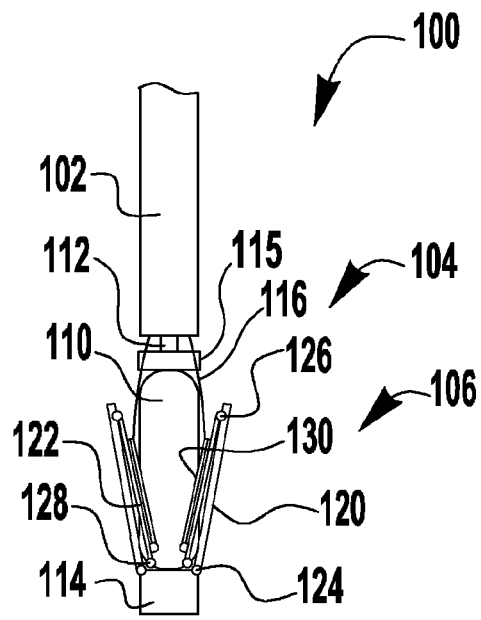

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the actuation member or actuation element 112 is retracted to pull the cap 114 towards the coaption element 110. The joints or flexible connections 126 between the outer paddle 120 and inner paddle 122 are constrained in movement such that compression forces acting on the outer paddle 120 from the cap 114 being retracted towards the coaption element 110 cause the paddles 120, 122 or gripping elements to move radially outward. During movement from the open to closed position, the outer paddles 120 maintain an acute angle with the actuation element 112. The outer paddles 120 can optionally be biased toward a closed position. The inner paddles 122 during the same motion move through a considerably larger angle as they are oriented away from the coaption element 110 in the open condition and collapse along the sides of the coaption element 110 in the closed condition. In some embodiments, the inner paddles 122 are thinner and/or narrower than the outer paddles 120, and the joint or flexible portions 126, 128 connected to the inner paddles 122 can be thinner and/or more flexible. For example, this increased flexibility can allow more movement than the joint or flexible portion 124 connecting the outer paddle 124 to the cap 114. In some embodiments, the outer paddles 120 are narrower than the inner paddles 122. The joint or flexible portions 126, 128 connected to the inner paddles 122 can be more flexible, for example, to allow more movement than the joint or flexible portion 124 connecting the outer paddle 124 to the cap 114. In some embodiments, the inner paddles 122 can be the same or substantially the same width as the outer paddles.

Figure 12:
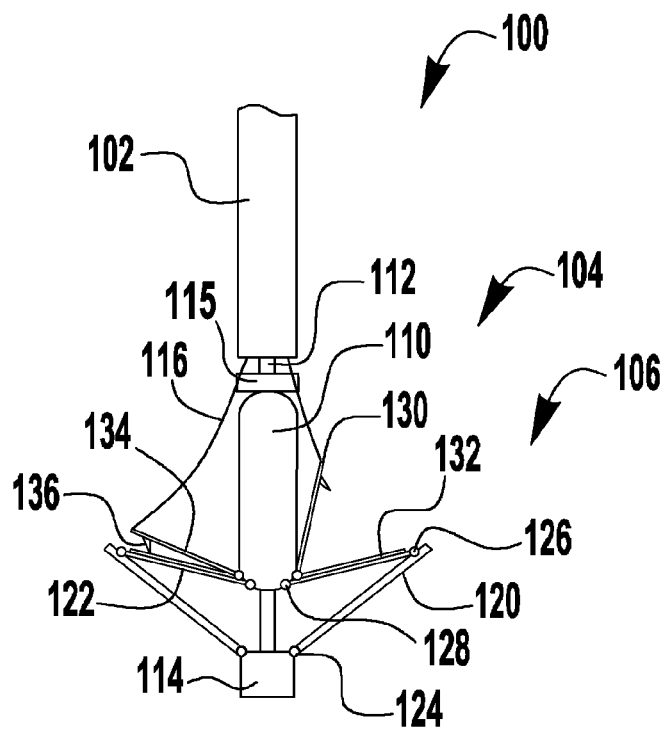
Figure 13:
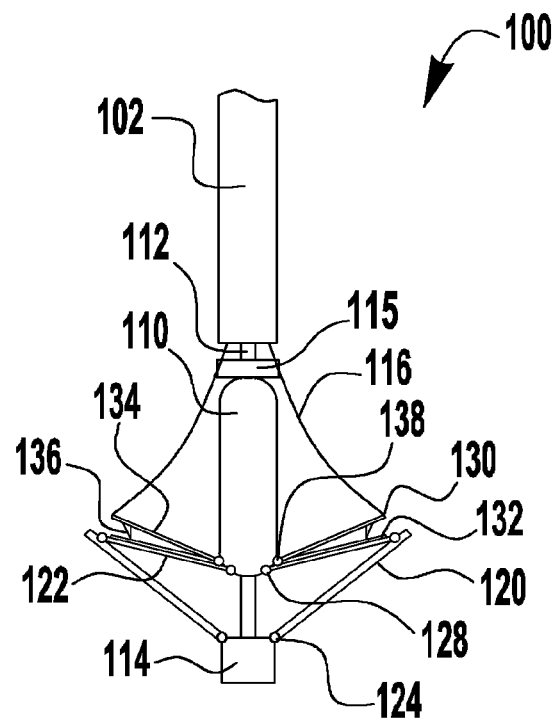

Referring now to FIGS. 11-13, the device 100 is shown in a partially open, grasp-ready condition. To transition from the fully closed to the partially open condition, the actuation member or actuation element 112 is extended to push the cap 114 away from the coaption element 110, thereby pulling on the outer paddles 120, which in turn pulls on the inner paddles 122, causing the anchor portion 106 to partially unfold. The actuation lines 116 are also retracted to open the clasps 130 so that the leaflets can be grasped. In the example illustrated by FIG. 11, the pair of inner and outer paddles 122, 120 are moved in unison, rather than independently, by a single actuation element 112. Also, the positions of the clasps 130 are dependent on the positions of the paddles 122, 120. For example, referring to FIG. 10 closing the paddles 122, 120 also closes the clasps. In certain embodiments, the paddles 120, 122 can be independently controllable. For example, the device 100 can have two actuation members or actuation elements and two independent caps, such that one independent wire and cap are used to control one paddle, and the other independent wire and cap are used to control the other paddle.

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 may be repeatedly actuated to repeatedly open and close the barbed clasps 130.

Figure 14:
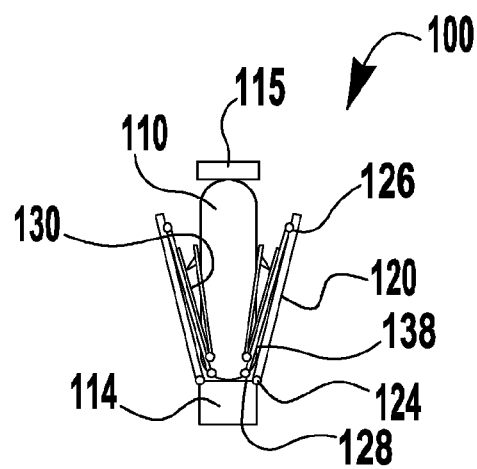

Referring now to FIG. 14, the device 100 is shown in a fully closed and deployed condition. The delivery sheath 102 and actuation member or actuation element 112 are retracted and the paddles 120, 122 and clasps 130 remain in a fully closed position. Once deployed, the device 100 may be maintained in the fully closed position with a mechanical latch or can be biased to remain closed through the use of spring materials, such as steel, other metals, plastics, composites, etc. or shape-memory alloys such as Nitinol. For example, the jointed or flexible portions 124, 126, 128, 138, and/or the inner and outer paddles 122, and/or an additional biasing component can be formed of metals such as steel or shape-memory alloy, such as Nitinol—produced in a wire, sheet, tubing, or laser sintered powder—and are biased to hold the outer paddles 120 closed around the coaption element 110 and the barbed clasps 130 pinched around native leaflets. Similarly, the fixed and moveable arms 132, 134 of the barbed clasps 130 are biased to pinch the leaflets. In certain embodiments, the joint portions 124, 126, 128, 138, and/or the inner and outer paddles 122, and/or an additional biasing component may be formed of any other suitably elastic material, such as a metal or polymer material, to maintain the device in the closed condition after implantation.

Figure 15:
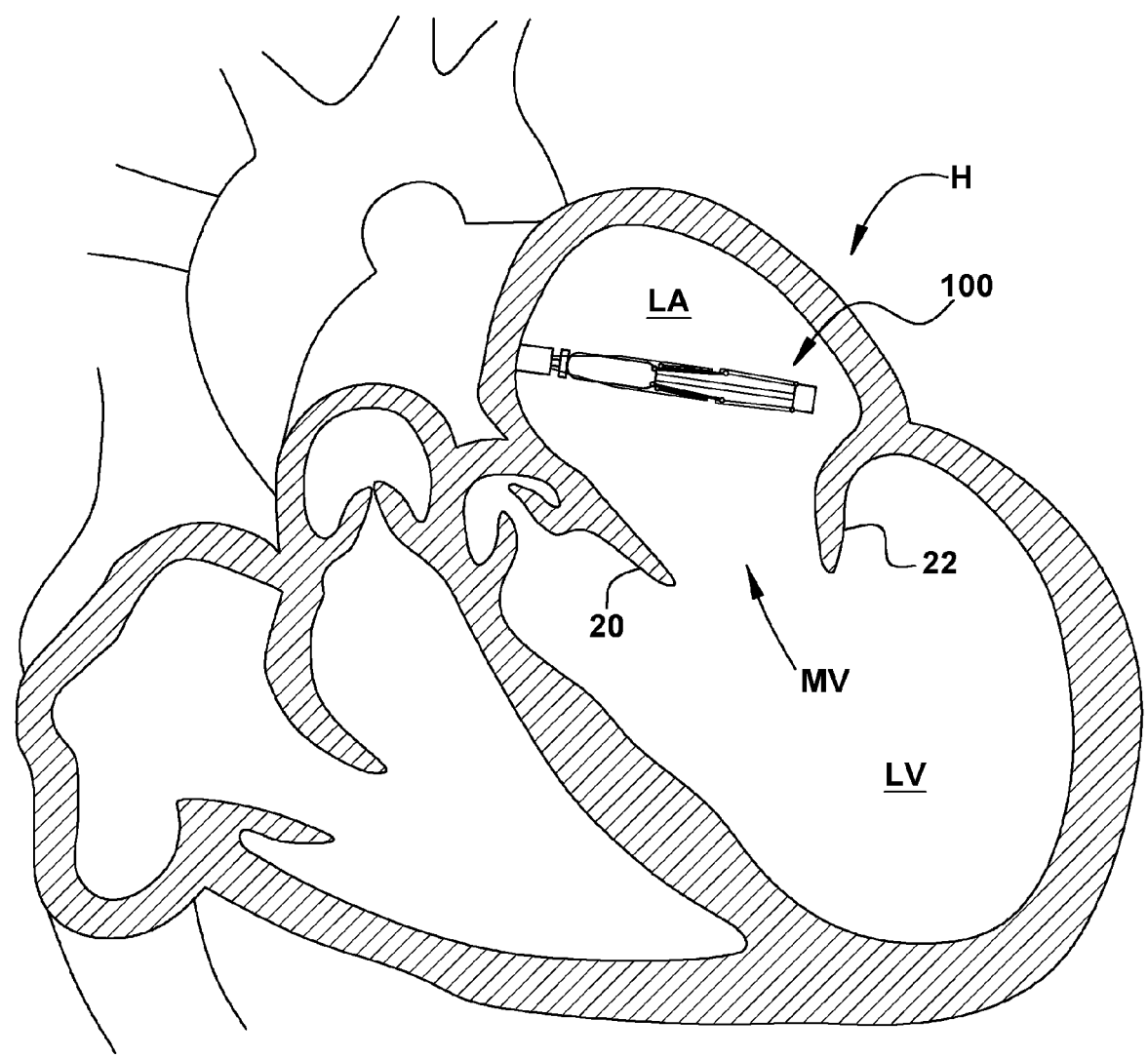
FIGS. 15-20 show the example implantable prosthetic device of FIGS. 8-14 being delivered and implanted within a native mitral valve.
Figure 16:
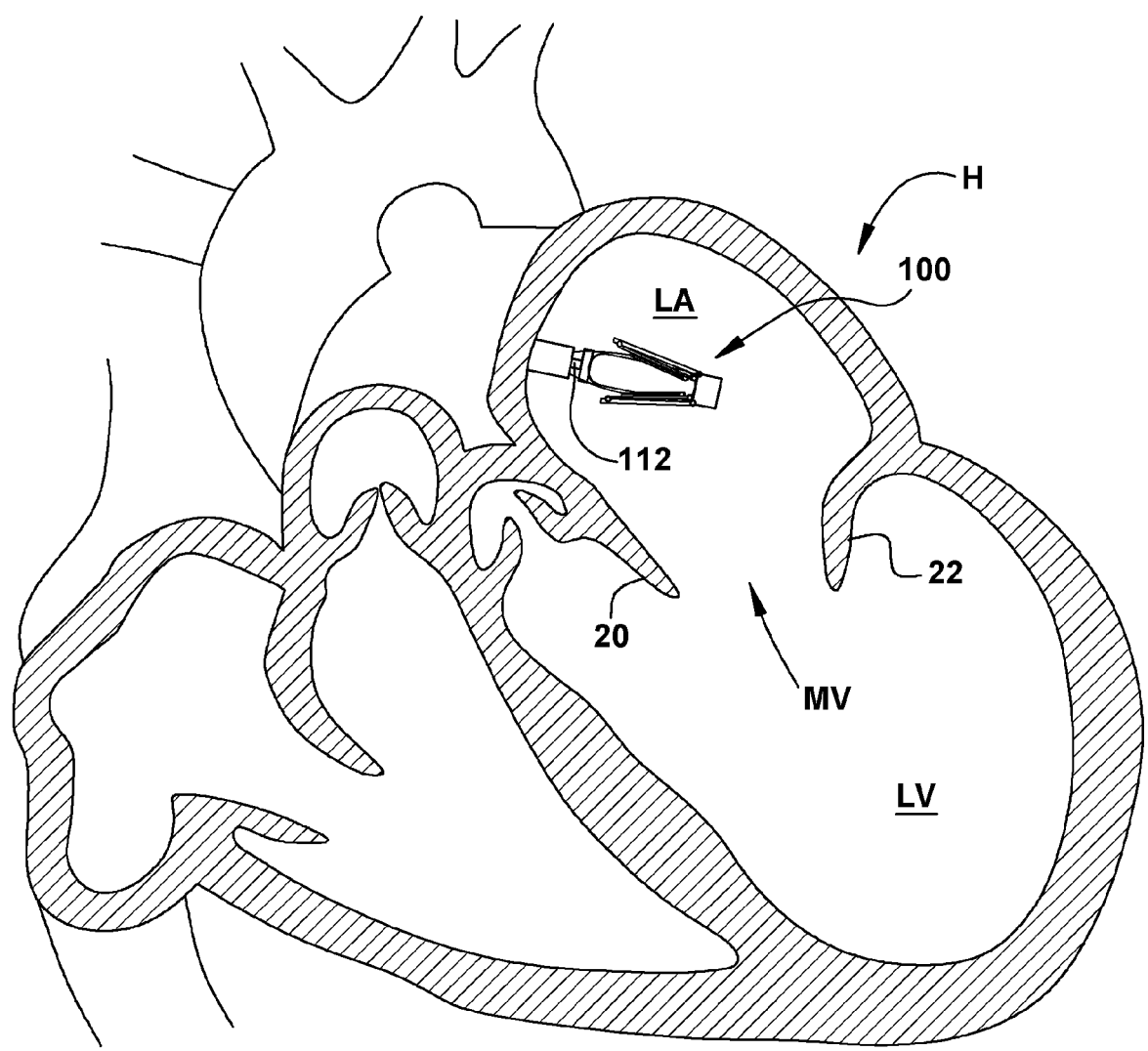
Figure 17:
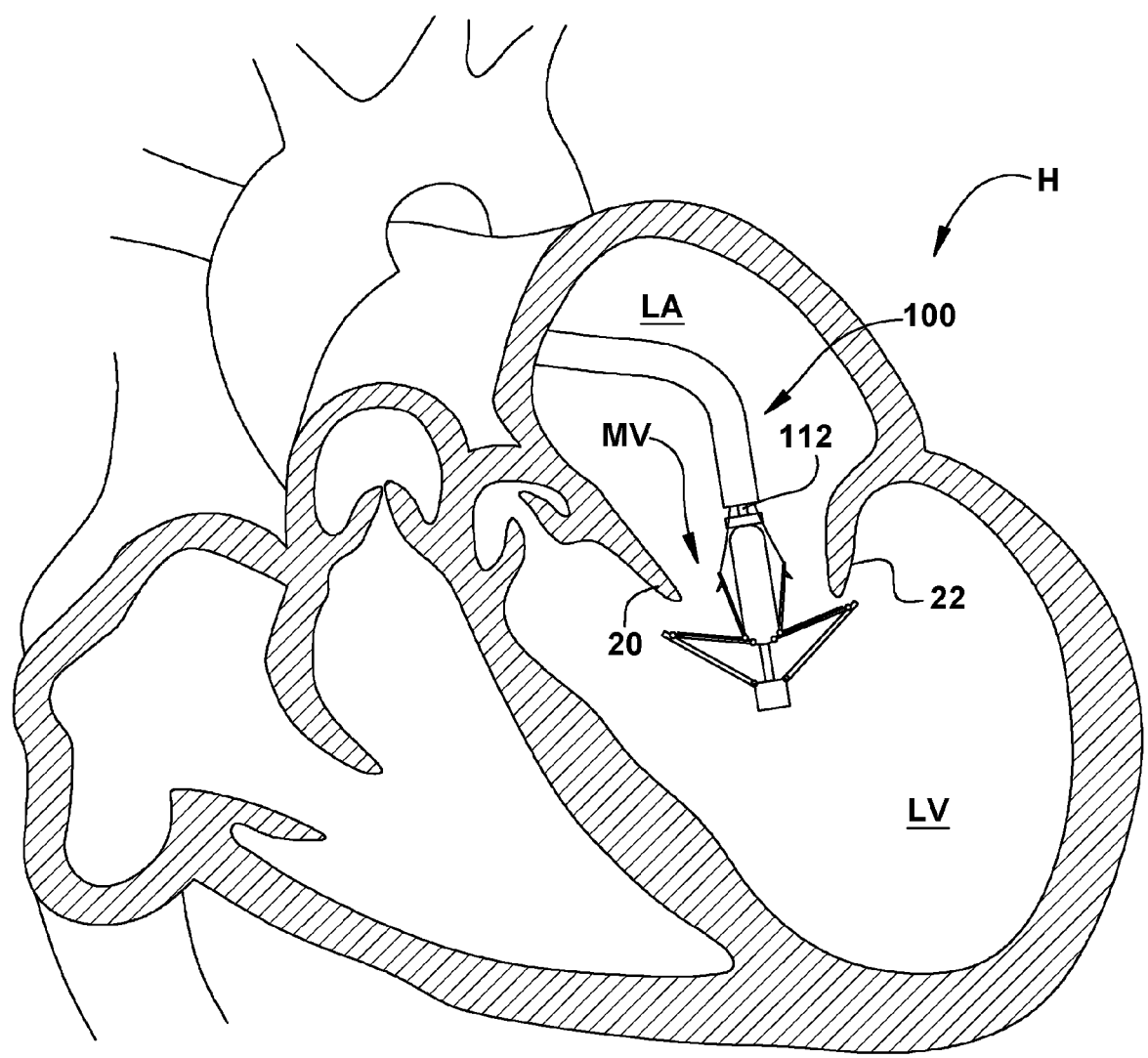
Figure 18:
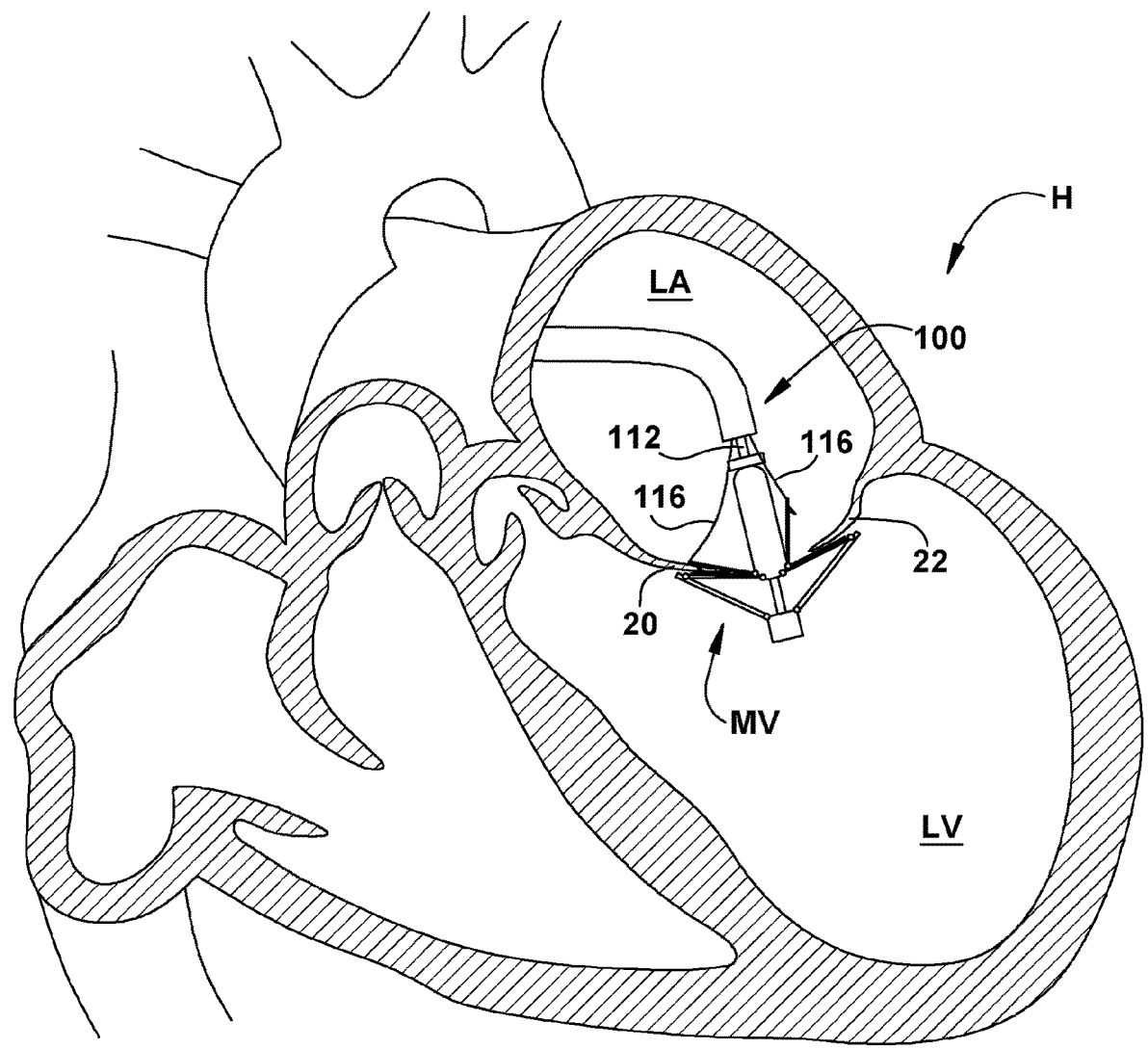
Figure 19:
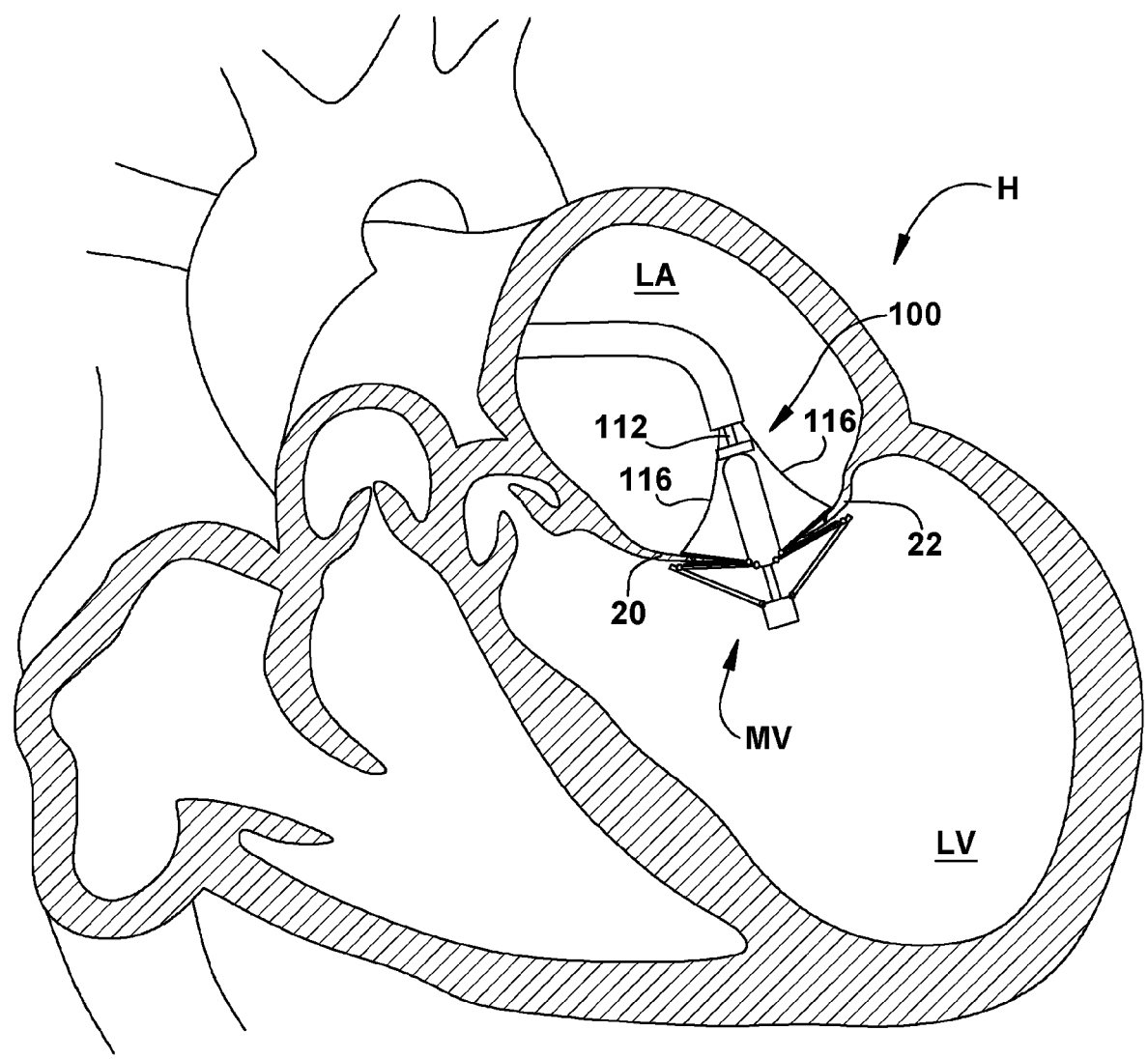
Figure 20:
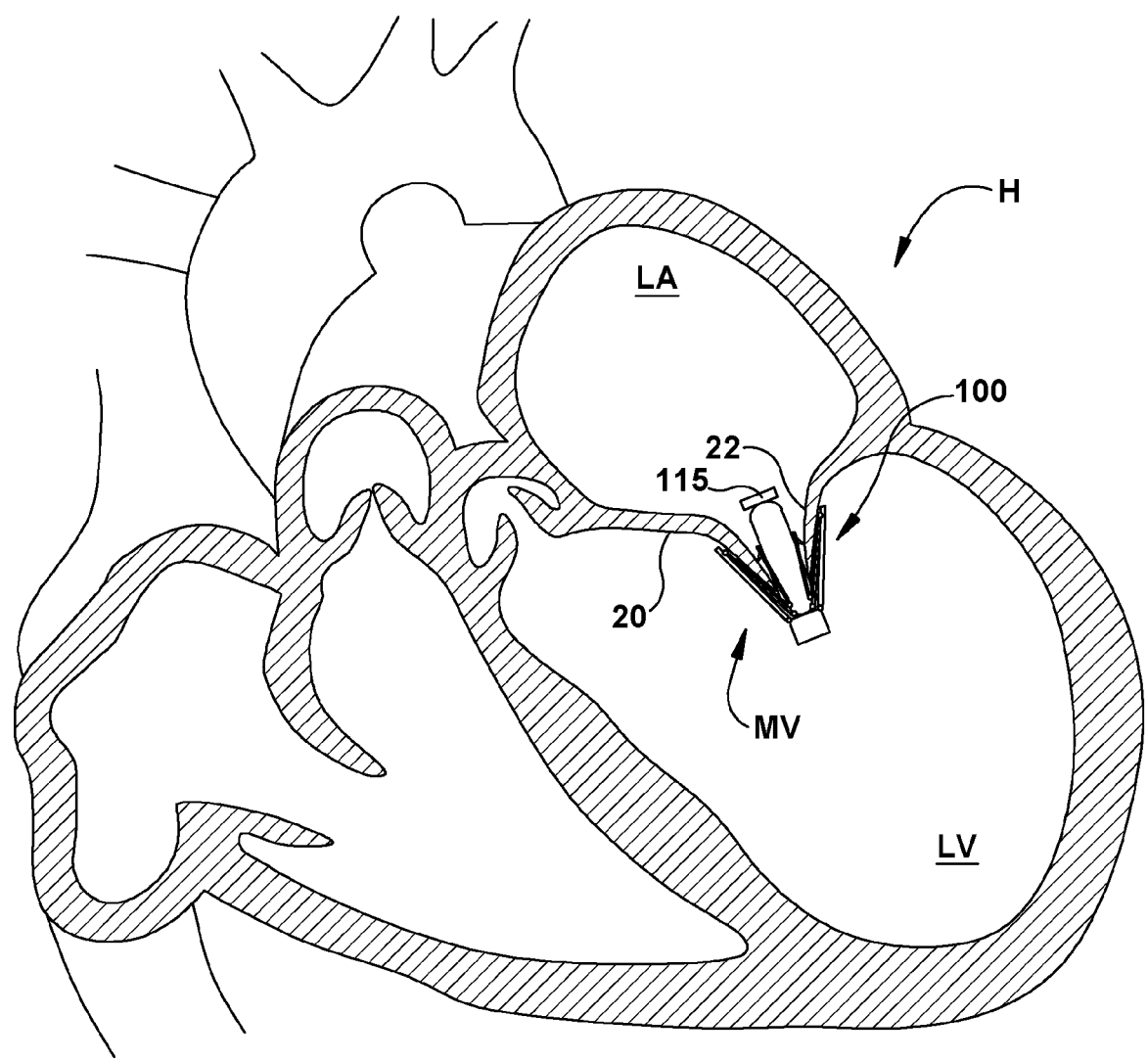

Referring now to FIGS. 15-20, the implantable device 100 of FIGS. 8-14 is shown being delivered and implanted within the native mitral valve MV of the heart H. Referring now to FIG. 15, the delivery sheath is inserted into the left atrium LA through the septum and the device 100 is deployed from the delivery sheath in the fully open condition. The actuation element 112 is then retracted to move the device 100 into the fully closed condition shown in FIG. 16. As can be seen in FIG. 17, the device 100 is moved into position within the mitral valve MV into the ventricle LV and partially opened so that the leaflets 20, 22 can be grasped. Referring now to FIG. 18, an actuation line 116 is extended to close one of the clasps 130, capturing a leaflet 20. FIG. 19 shows the other actuation line 116 being then extended to close the other clasp 130, capturing the remaining leaflet 22. Lastly, as can be seen in FIG. 20, the delivery sheath 102 and actuation element 112 and actuation lines 116 are then retracted and the device 100 is fully closed and deployed in the native mitral valve MV.

Figure 21:
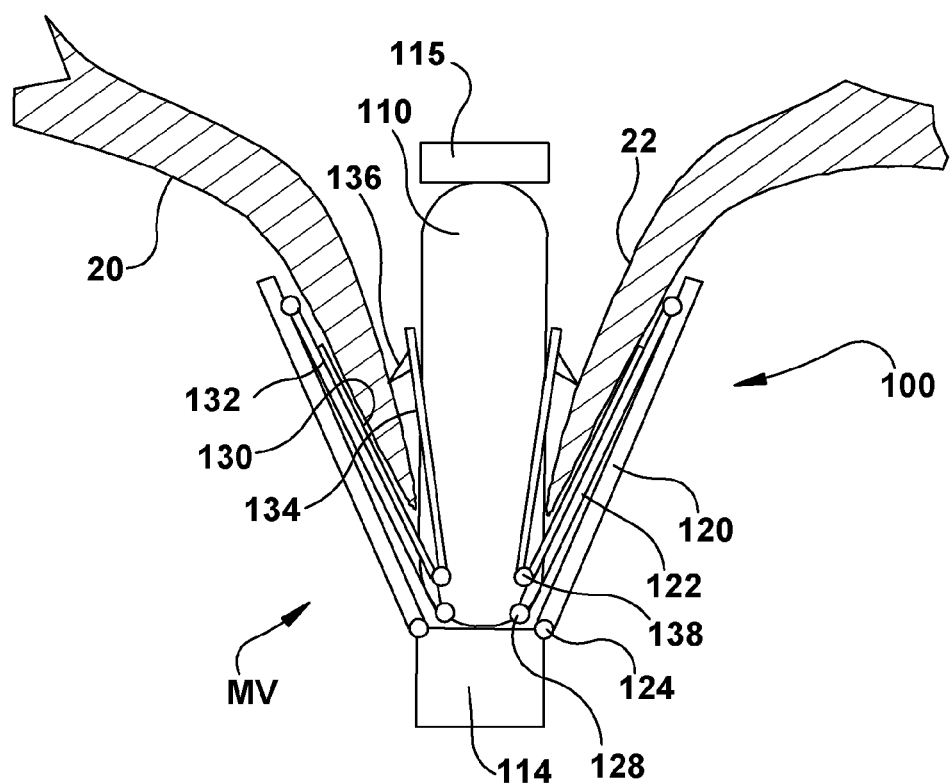
FIG. 21 shows the implantable prosthetic device of FIGS. 8-14 implanted within a native valve.

Referring now to FIG. 21, the device 100 of FIGS. 8-14 is shown implanted within a native valve or native mitral valve MV in the fully closed position. The implanted device 100 has outer paddles 120, inner paddles 122, barbed clasps 130, a coaption element 110, and a cap 114. The outer paddles 120 and the inner paddles 122 are connected between the cap 114 and the coaption element 110 by portions 124, 126, 128 (which can be jointed and/or flexible to move between various positions). The coaption element 110 is adapted to be implanted between the leaflets 20, 22 of the mitral valve MV. The barbed clasps 130 are configured to connect device 100 to the leaflets 20, 22. In certain embodiments, the barbed clasps 130 include a fixed arm that is attached to the inner paddle 122 and a movable arm 134 that has a barb for engaging the leaflets 20, 22 of the mitral valve MV. The device 100 is connected to the mitral valve MV by positioning the device 100 (in an open position) such that the leaflets 20, 22 are between the inner paddle 122 (and the fixed arm 132 of the barbed clasp 130) and the movable arm 134 of the barbed clasp 134). Subsequently, the device 100 is moved to the fully closed position (as shown in the illustrated embodiment) and the movable arms 134 are moved such that the barbs 136 engage the leaflets 20, 22 to secure the device 100 to the mitral valve MV.

Figure 22:
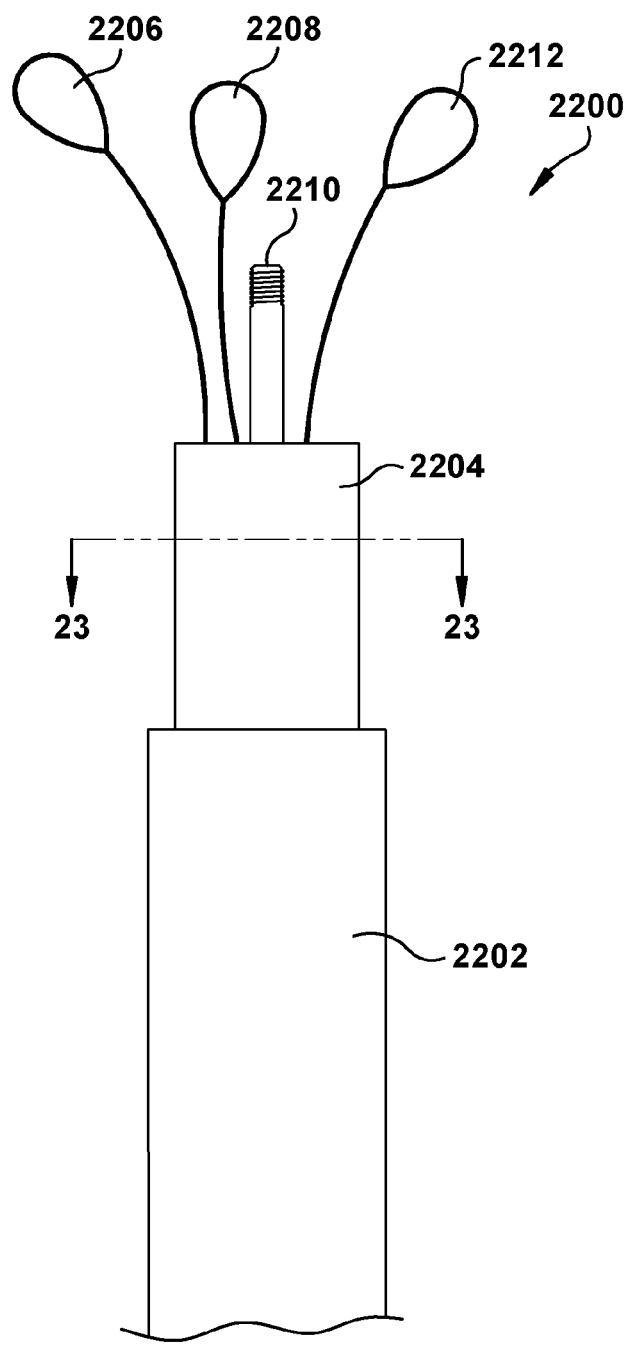
FIG. 22 shows an example embodiment of a retrieval device or system for retrieving an implanted prosthetic device from a native valve.
Figure 23:
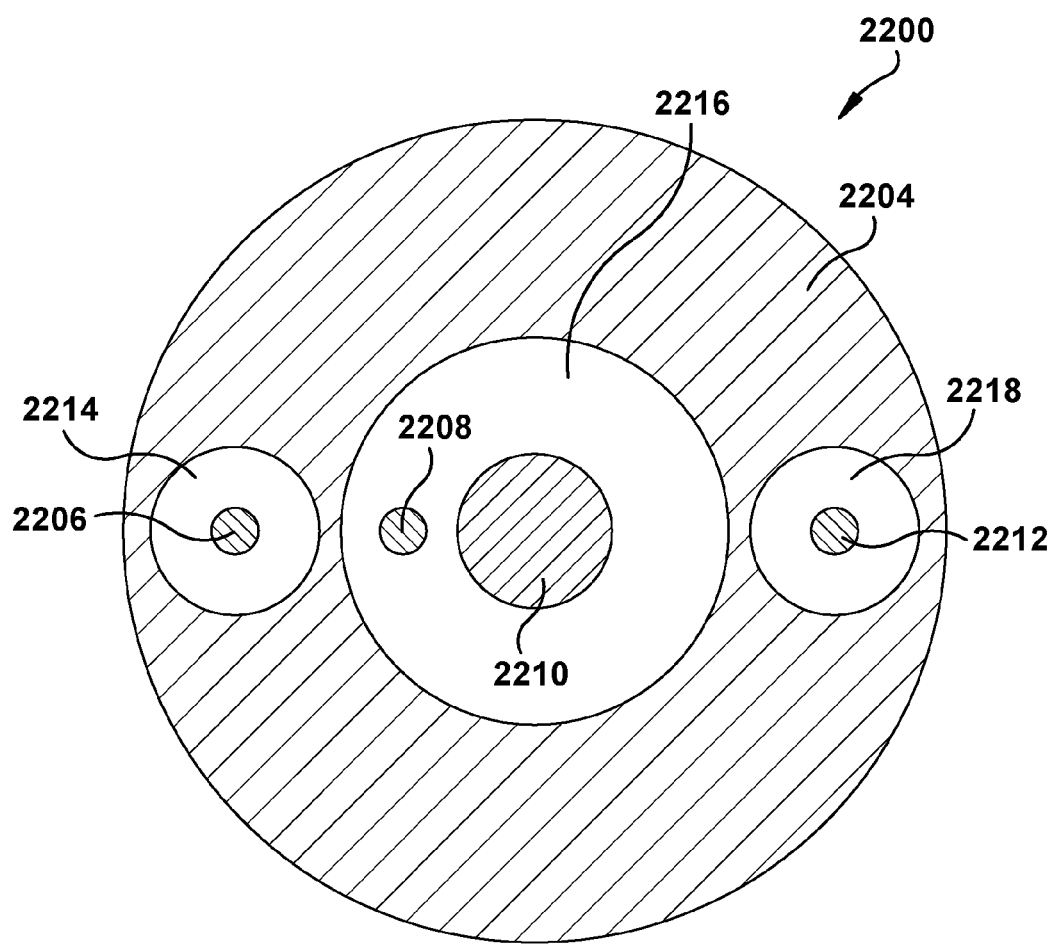
FIG. 23 is a cross-sectional view of the example retrieval device/system of FIG. 22 shown along the lines 23-23 of FIG. 22.

Referring now to FIGS. 22 and 23, an example embodiment of a retrieval device 2200 is shown that is configured to remove and retrieve a device that was previously implanted within a patient's native valve (e.g., implanted device 100 shown in FIGS. 8-14 and 21). The retrieval device 2200 can have less than all of the parts shown in FIGS. 22 and 23. For example, in at least the embodiments illustrated by FIGS. 58-78, the retrieval device 2200 can have fewer than all of the retrieval components illustrated by FIGS. 22 and 23.

The previously implanted device can be retrieved after it has been implanted for various periods of time. In some embodiments, the retrieval device 2200 can be used to retrieve a device 100 that has been implanted within a patient's native valve for one month or less, such as 30 days or less, such as 25 days or less, such as 20 days or less, such as 15 days or less, such as 10 days or less, such as seven days or less, such as six days or less, such as five days or less, such as four days or less, such as three days or less, such as two days or less, such as one day or less, such as 20 hours or less, such as 15 hours or less, such as 10 hours or less, such as five hours or less, such as one hour or less, such as 30 minutes or less, such as 10 minutes or less, such as 5 minutes or less, such as one minute or less. In some embodiments, the retrieval device 2200 can be used to retrieve a device 100 that has been implanted within a patient's native valve for more than one month. While the retrieval device is described as retrieving the implanted device 100, it should be understood that the retrieval device 2200 can be used to retrieve any suitable type of device that is implanted within a native valve of a patient.

The example retrieval device 2200 includes a catheter 2202 that is configured to position the retrieval device 2200 to engage the implanted device 100, a retrieval shaft 2204, and one or more components (2206, 2208, 2210, 2212) housed within the retrieval shaft 2204. The one or more components (2206, 2208, 2210, 2212) are configured to engage the implanted device 100 to remove the implanted device from a native valve. In the illustrated embodiment, the one or more components include actuation member or actuation element 2210, a securing member 2208, and one or more capturing members (2206, 2212). The actuation member/element 2210 can take a variety of forms (e.g., a rod, shaft, bar, wire, line, hook, suture, any other form described with respect to actuation members anywhere herein, a combination of two or more of these, etc.) and be made of one or more of a variety of materials, for example, metal, such as steel, nitinol, etc. The securing member 2208 can also take a variety of forms (e.g., a wire, wire loop, wire with a barb, snare, lasso, hook, tether, line, ring, hoop, any other form described with respect to securing members anywhere herein, a combination of two or more of these, etc.) be made of one or more of a variety of materials, for example, metal, such as steel, nitinol, etc. The one or more capturing members (2206, 2212) can take a variety of forms, for example, a wire, a wire loop, a wire with a barb, a snare, a lasso, a hook, a tether, a line, a ring, a hoop, any other form described with respect to capturing members anywhere herein, any other suitable member that is capable of capturing a portion of an implanted device 100, and/or a combination of two or more of these. The capturing members (2206, 2212) can be made of one or more of a variety of materials, for example, metal, such as steel, nitinol, etc.

Referring to FIG. 23, the retrieval shaft 2204 can have one or more lumens or bores (2214, 2216, 2218) for guiding the one or more components (2206, 2208, 2210, 2212). In the illustrated embodiment, the actuation member 2210 and the securing member 2208 are disposed in a first lumen 2216, a first capturing member 2206 is disposed in a second lumen 2214, and a second capturing member 2212 is disposed in a third lumen 2218. In other embodiments, all of the components (2206, 2208, 2210, 2212) can be disposed in a single lumen, each of the components (2206, 2208, 2210, 2212) can be disposed in a lumen by itself, or any other suitable number of lumens can be used to guide the components.

Figure 24:
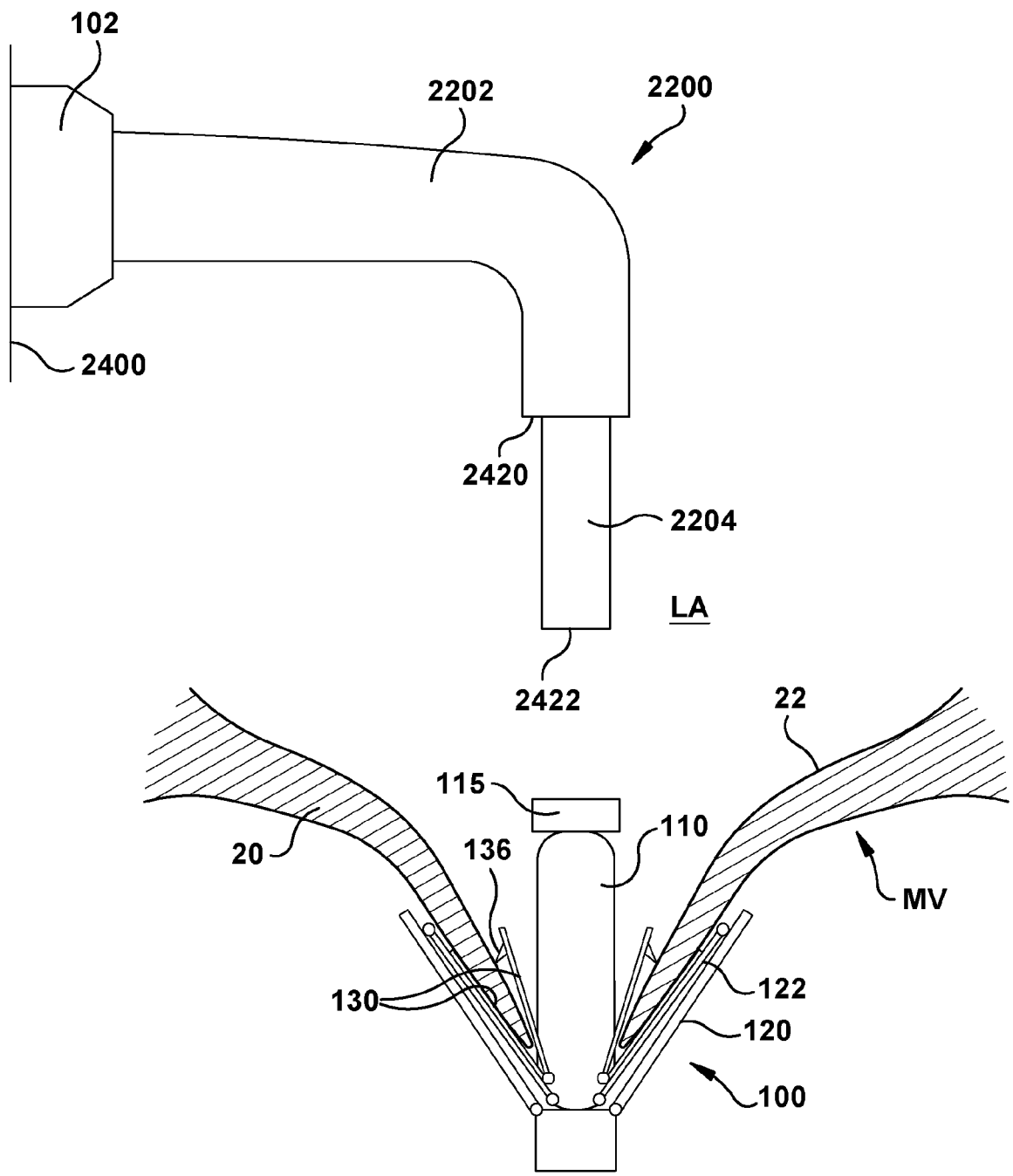
FIGS. 24-34 show the example retrieval device of FIG. 22 being positioned to engage and engaging the example implanted prosthetic device of FIG. 21 to remove the implanted prosthetic device from a native valve, according to a first example method.
Figure 25:
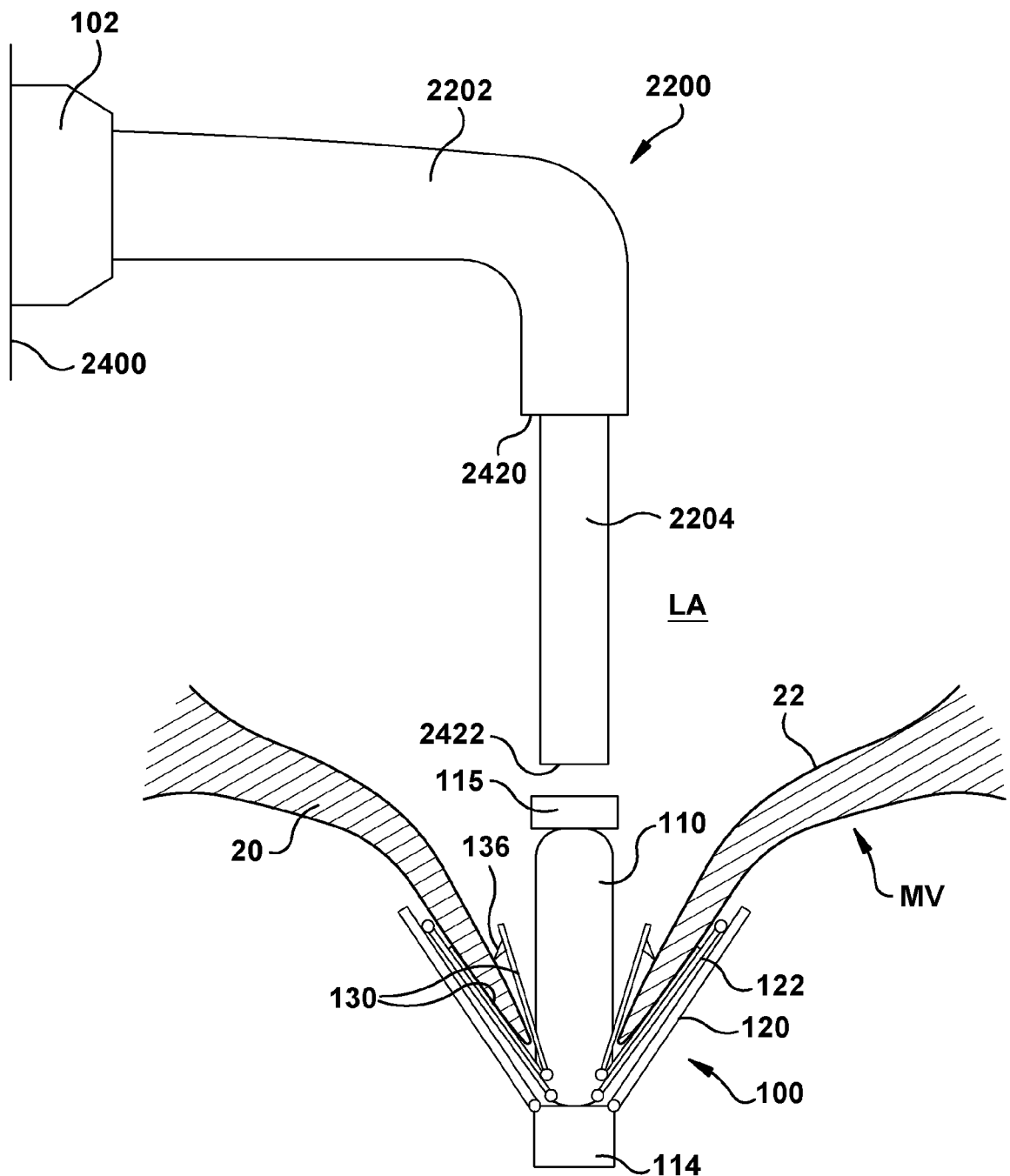

Referring now to FIGS. 24-34, the retrieval device 2200 is shown being positioned to engage an implanted device 100 on the native valve or native mitral valve MV and engaging the implanted device 100 to remove the implanted device from the native valve, according to an example embodiment. As with other examples herein, even though a specific valve, e.g., mitral valve MV, may be shown, similar principles apply to other native valves. Referring to FIGS. 24 and 25, the retrieval device 2200 is shown extending through the septum 2400 of a heart such that the retrieval device 2200 is positioned in the left atrium LA of the heart. In certain embodiments, a delivery sheath 102 is used to deliver the retrieval device 2200 to the heart of a patient. The delivery sheath 102 can deliver the retrieval device to the patient's heart by any suitable means, such as, for example, by any means described in the present application regarding the delivering and implanting of the implantable device 100. After the sheath 102 is positioned in the left atrium LA, the catheter 2202 can be configured to be steerable such that the distal end 2420 can be positioned above the implanted device 100. Referring to FIG. 25, after the distal end 2420 of the catheter 2202 is positioned above the implanted device 100, the retrieval shaft 2204 can be extended out of a distal end 2420 of the catheter 2202 to position the one or more components (2206, 2208, 2210, 2212) to engage and retrieve the implanted device 100. In certain embodiments, the distal end 2422 of the retrieval shaft 2204 is positioned near the collar 115 of the device 100.

Figure 26:
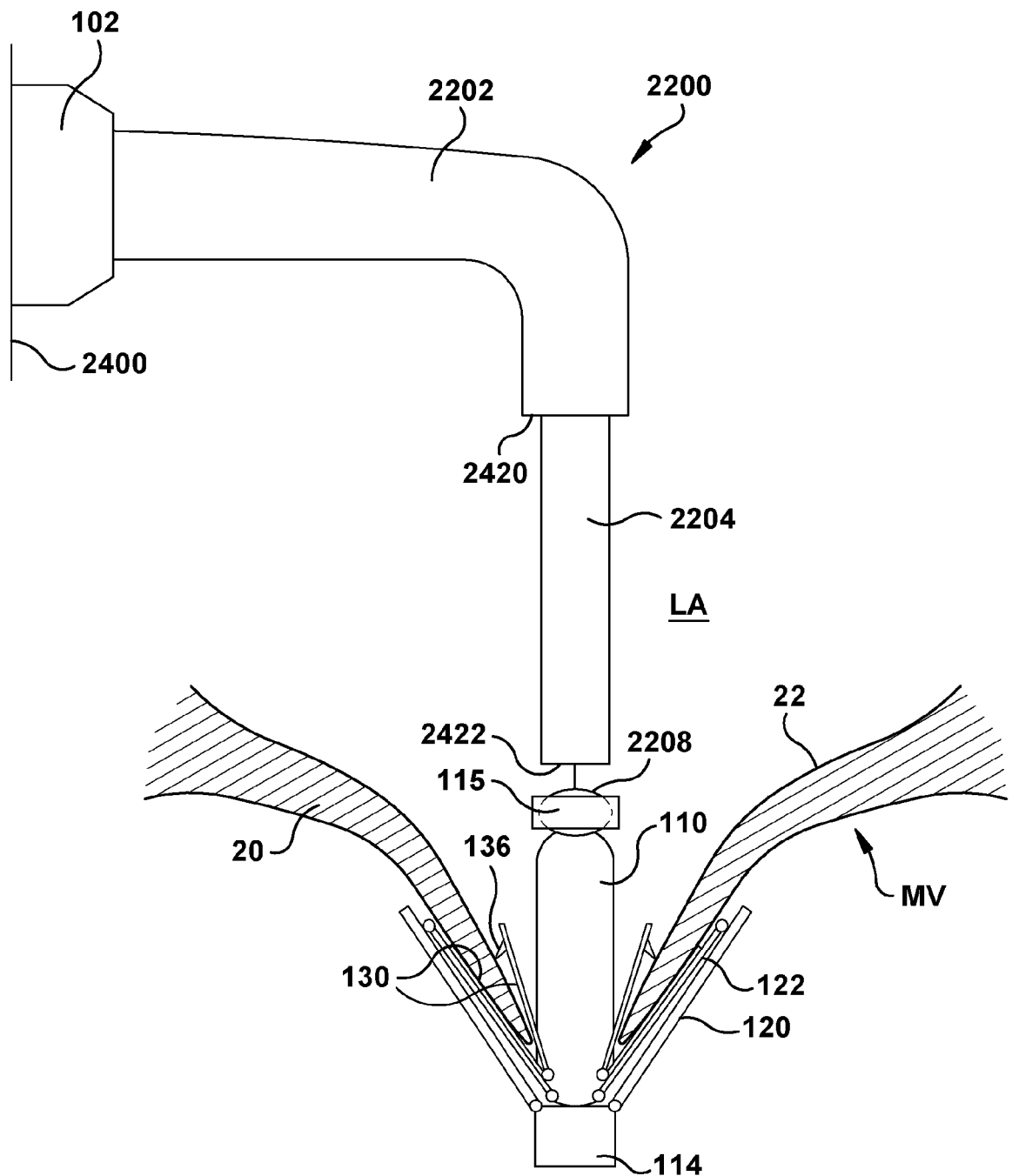

Referring to FIG. 26, once the distal end 2422 of the retrieval shaft 2204 is positioned near or in contact with the collar 115 of the device 100, the securing member 2208 is configured to be extended from the retrieval shaft 2204 and engage the collar 115 to secure the retrieval device 2200 to the implanted device 100. In the illustrated embodiment, the securing member 2208 is a snare having a wire loop, in which the wire loop is configured to extend around the collar 115. The securing member 2208 can, however, take any suitable form, such as, for example, a clip, a magnet, a detent mechanism, a coupler, a hook and loop connection, any frictional connection, a twist to lock type connection, any other form described with respect to securing members anywhere herein, or any other known fastening arrangement.

Figure 27:
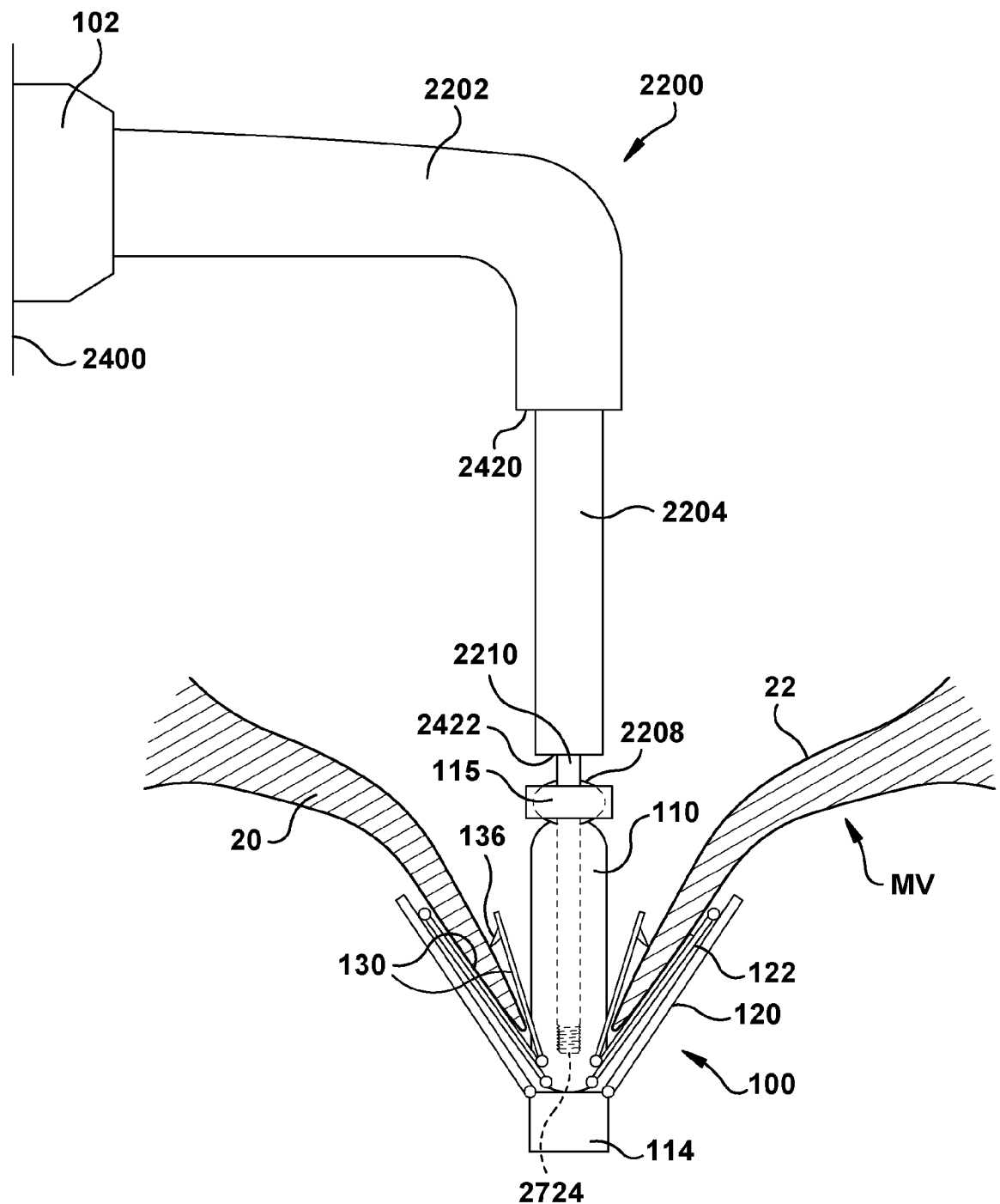
Figure 28:
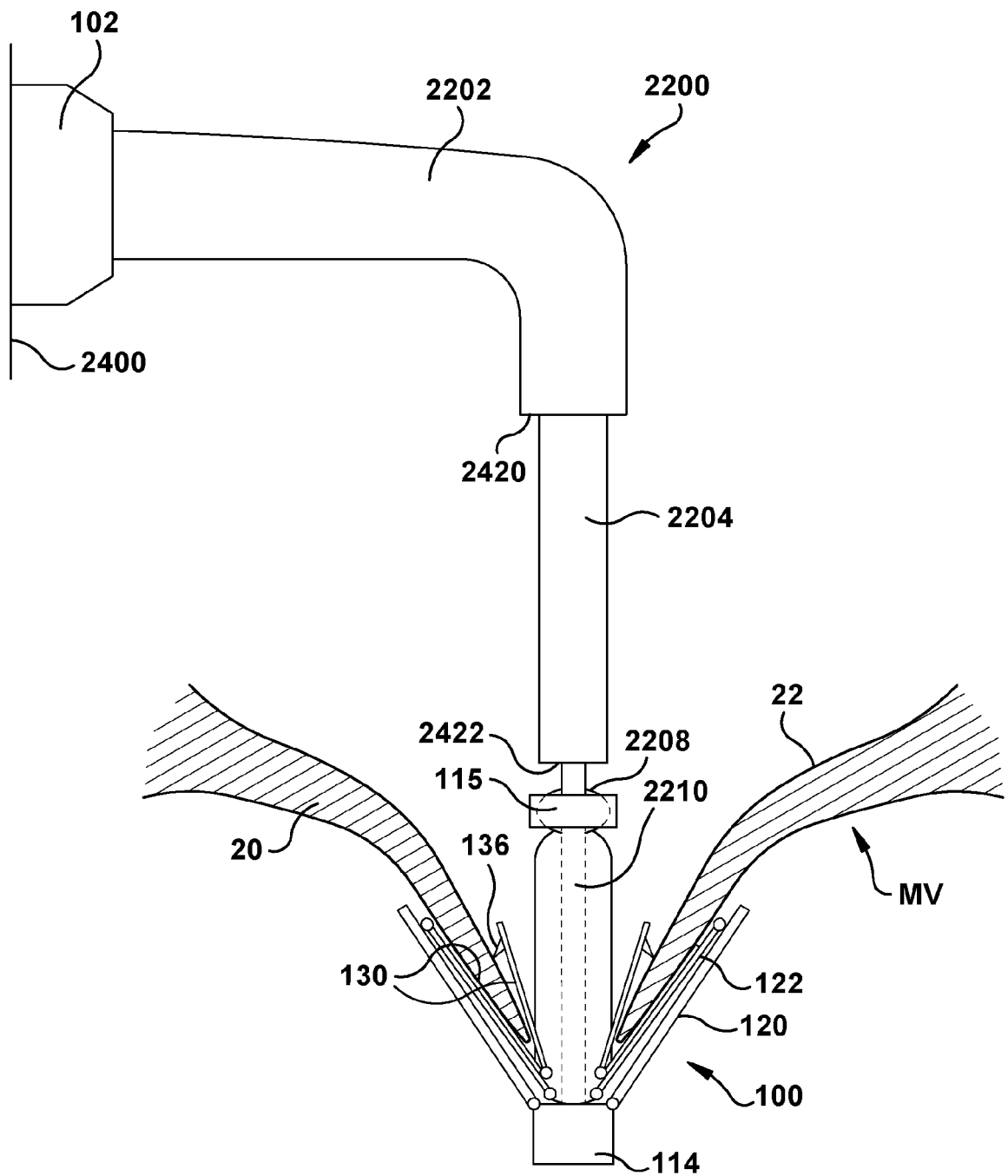

Referring to FIGS. 27 and 28, the actuation member/element 2210 is extended from the distal end 2422 of the retrieval shaft 2204 to engage the implanted device 100. The actuation member 2210 has a distal end 2724 that is configured to engage the cap 114. In certain embodiments, the distal end 2724 of the actuation member 2210 is configured to be attached to the cap 114 (as shown in FIG. 28). For example, the actuation member 2210 and the cap 114 can be connected by a threaded connection, a snap-fit connection, a frictional connection, a magnetic connection, a twist and lock type connection, or any other suitable connection. In the illustrated embodiment, the actuation member 2210 is threaded such that rotation of the actuation member connects the actuation member to the cap 114 of the implanted device 100. The actuation member/element 2210 can, however, take a wide variety of different forms, such as, for example, any form described for actuation element 112 in FIGS. 8-14, and/or any other form described with respect to actuation members or actuation elements anywhere herein.

Figure 29:
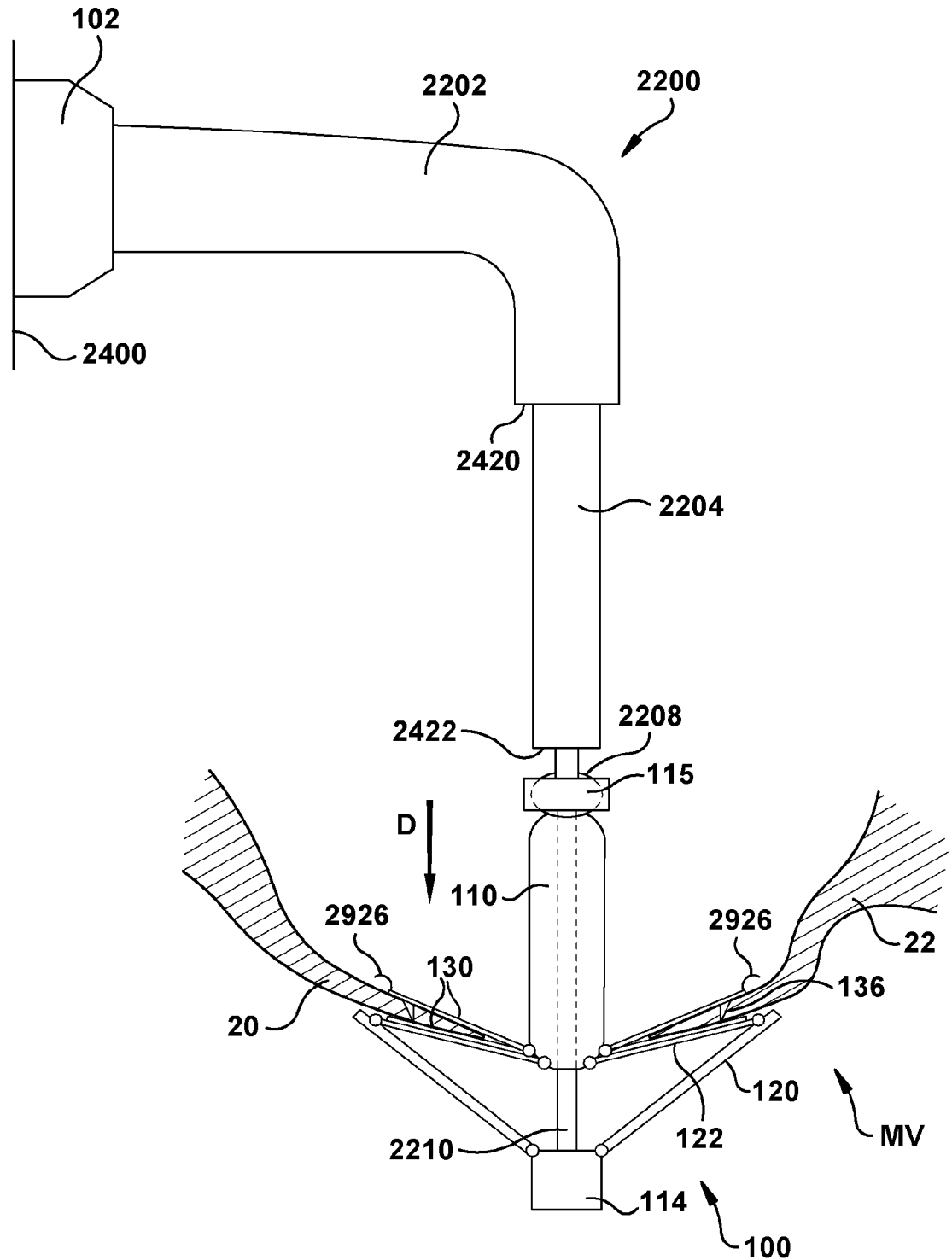

Referring to FIG. 29, the retrieval device 2200 is used to move the implanted device 100 to the partially opened position (as described above with reference to FIGS. 8-14) by moving the actuation member 2210 in the direction D while holding the position of the collar 115 with the securing member 2208 and/or the retrieval shaft 2204. The actuation member 2210 moves the cap 114 in the direction D.

In certain embodiments, the movable arms 134 of the gripping clasps 130 of the implanted device 100 include an optional attachment member 2926 that is configured to be engaged by a capturing member 2206, 2212 of the retrieval device 2200. The optional attachment members 2926 can be, for example, hooks, loops, magnets, hook and loop connection material, barbs, staples, clasps, clips, etc. or any other component or arrangement that facilitates attachment of the capturing members 2206, 2212.

Figure 30:
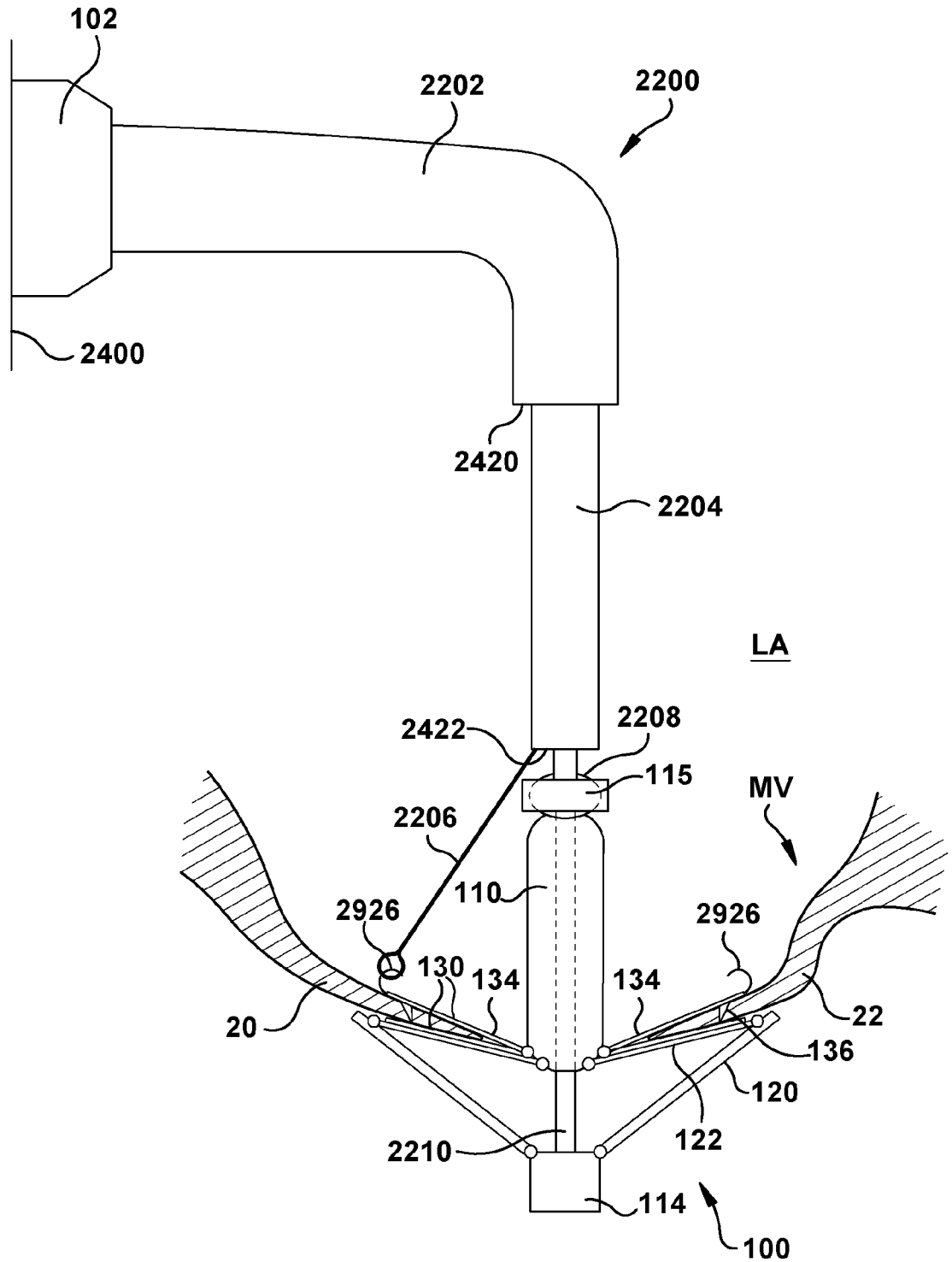
Figure 31:
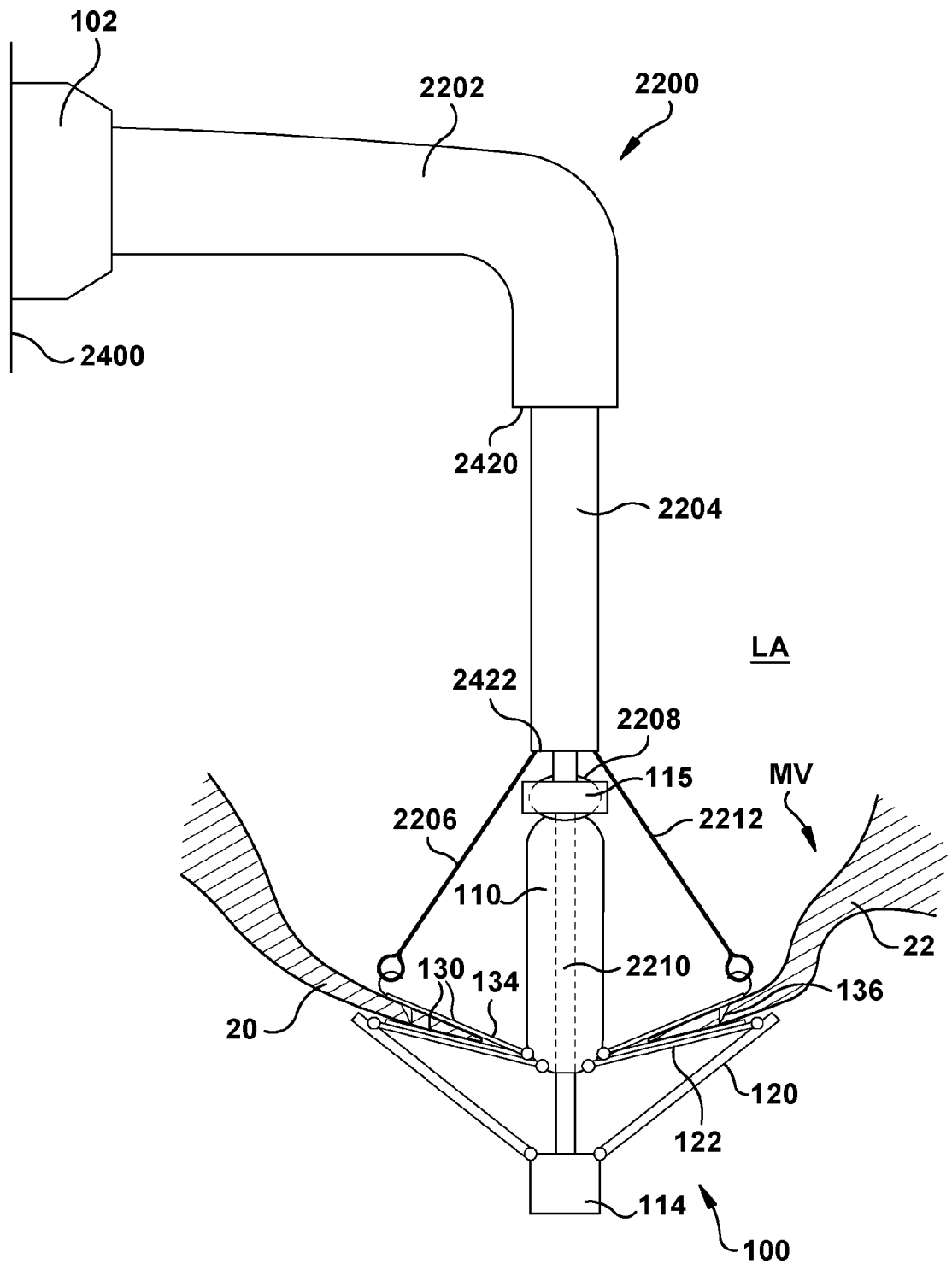

Referring to FIGS. 30 and 31, after the implanted device 100 is in the partially opened position, the first capturing member 2206 is extended from the distal end 2422 of the retrieval shaft 2204 and attached to the attachment member 2926 of one of the gripping clasps 130, and the second capturing member 2212 is extended from the distal end 2422 of the retrieval shaft 2204 and attached to the attachment member 2926 of the other gripping clasp 130. In the illustrated embodiment, the capturing members 2206, 2212 are snares with a wire loop that are configured to attach to attachment members 2926. The capturing members 2206, 2212 can, however, take any suitable form, such as, for example, a clip, a magnet, a detent mechanism, a coupler, a hook and loop connection, any frictional connection, a twist to lock type connection, any other form described with respect to capturing members anywhere herein, or any other known fastening arrangement. In the illustrated embodiment, the first capturing member 2206 is attached to the attachment member 2926 of a first gripping clasp 130 (as shown in FIG. 30), and then the second capturing member 2212 is attached to the attachment member 2926 of the other gripping clasp 130 (as shown in FIG. 31).

Figure 78:
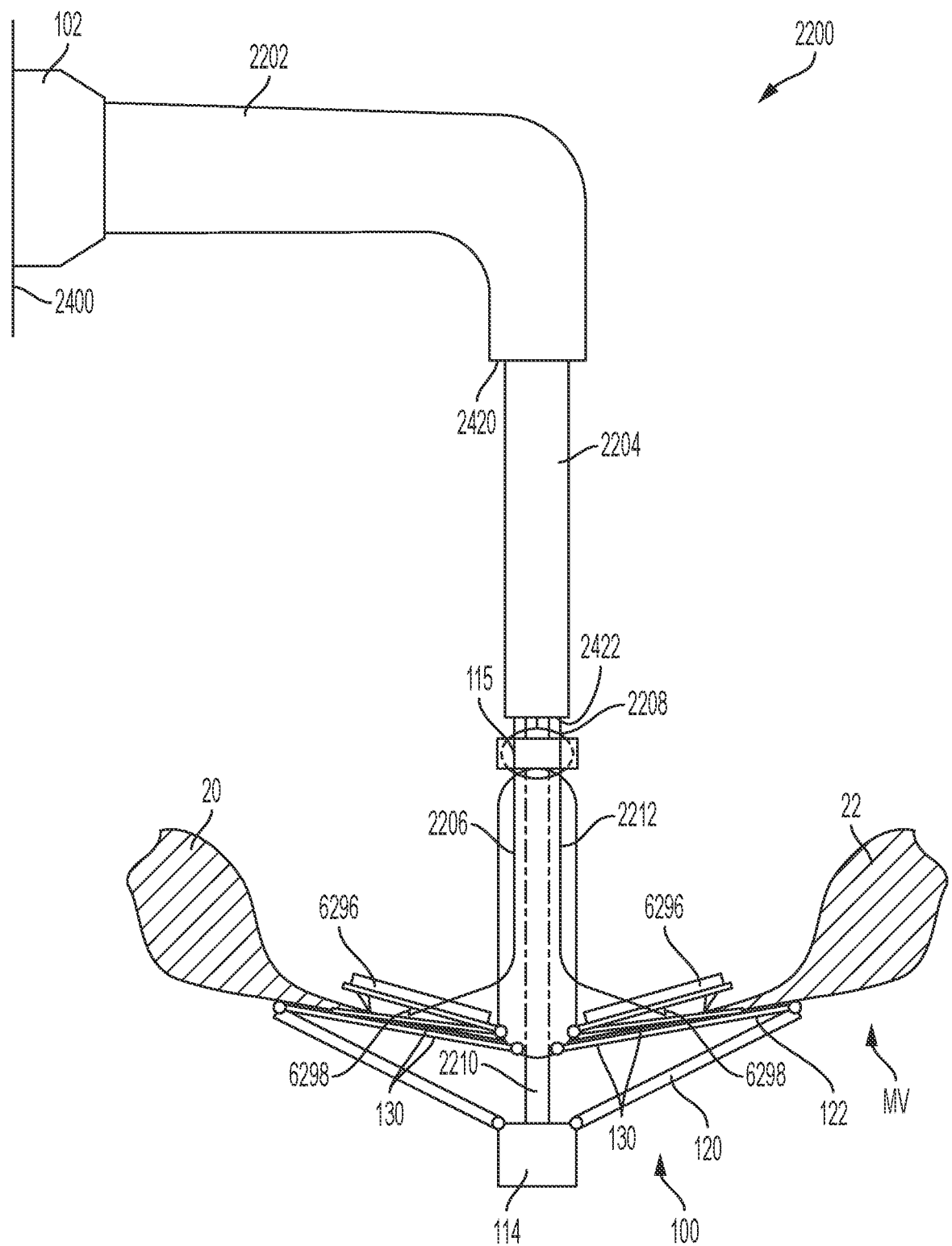
FIG. 78 shows the retrieval device of FIG. 22 engaging the implanted prosthetic device of FIG. 21, in which the retrieval device includes example capturing devices for engaging the clasps of the implanted prosthetic device.

Referring to FIG. 78, in some embodiments, the clasps are at least partially made from and/or are covered by a cloth material 6296. The capturing members 2206, 2212 can be barbed, sharp, or otherwise configured to attach to the cloth material 6296. For example, the capturing members 2206, 2212 can be wires with a barb 6298. In these embodiments, the capturing members 2206, 2212 are attached to the gripping clasps by piercing, becoming entangled with, or otherwise attaching to the cloth material. In one example embodiment, the capturing members 2206, 2212 include barbs 6298 that pierce the cloth material 6296 to capture the clasps.

Figure 32:
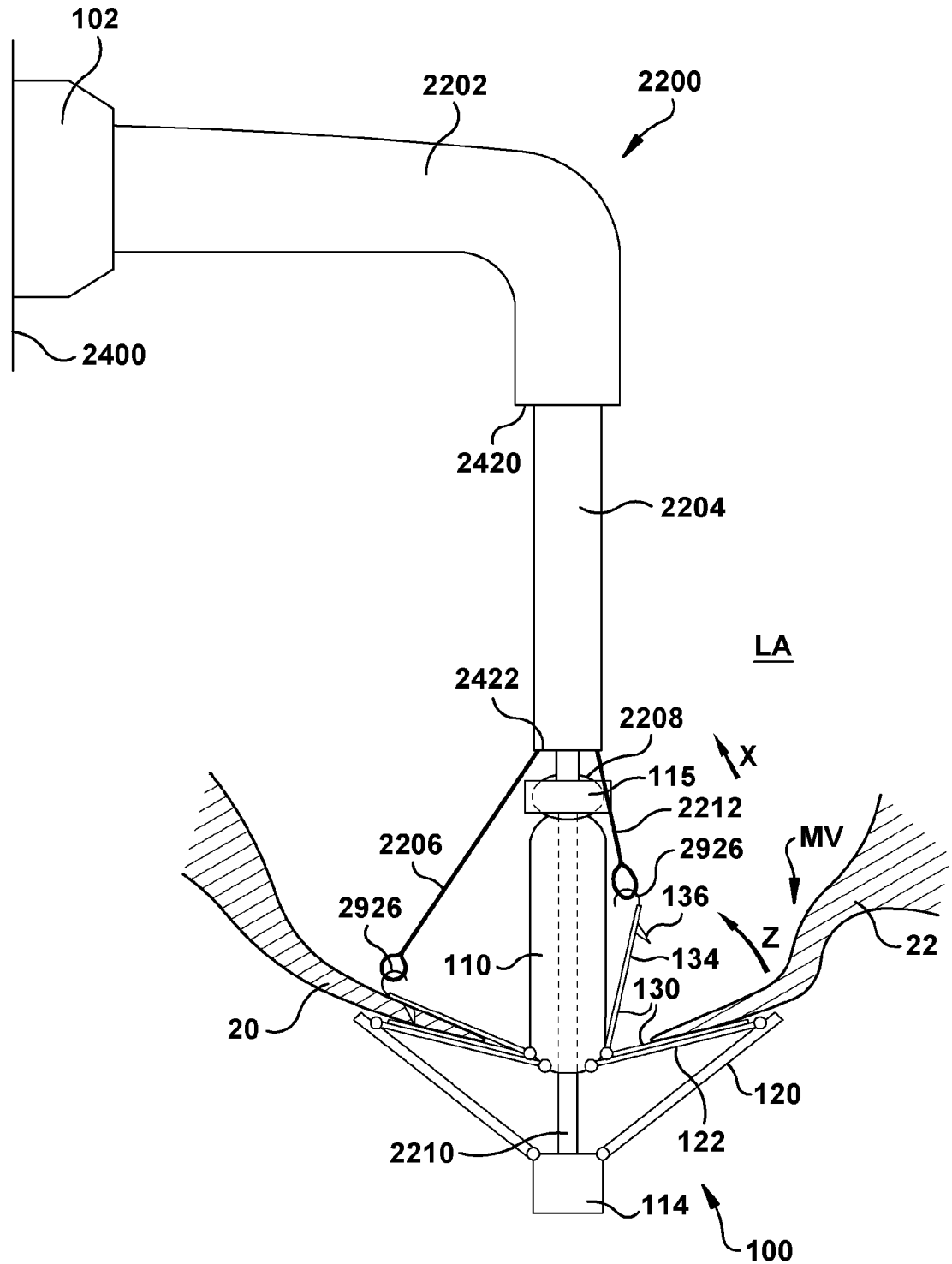

Referring to FIG. 32, after the capturing members 2206, 2212 of the retrieval device 2200 are attached to the connection members 2296 of the implanted device 100 (or otherwise attached to the arms 134), the capturing members 2206, 2212 are configured to provide a tension force to the movable arms 134 of the gripping clasps 130 to release the barbs 136 from the valve tissue of the leaflets 20, 22. For example, the capturing members 2206, 2212 can be pulled toward and/or into the retrieval shaft 2204 to release the barbs 136 from the native valve, e.g., the mitral valve MV in this example.

Still referring to FIG. 32, the capturing member 2212 is shown being moved in the direction X, which causes the movable arm 134 of the device 100 to move in the direction Z. The capturing member 2206 is similarly moved toward and/or into the retrieval shaft 2204 such that the corresponding movable arm 134 moves toward the coaption element 110 of the device 100 to release the barbs from the leaflet 20 of the mitral valve MV.

Figure 33:
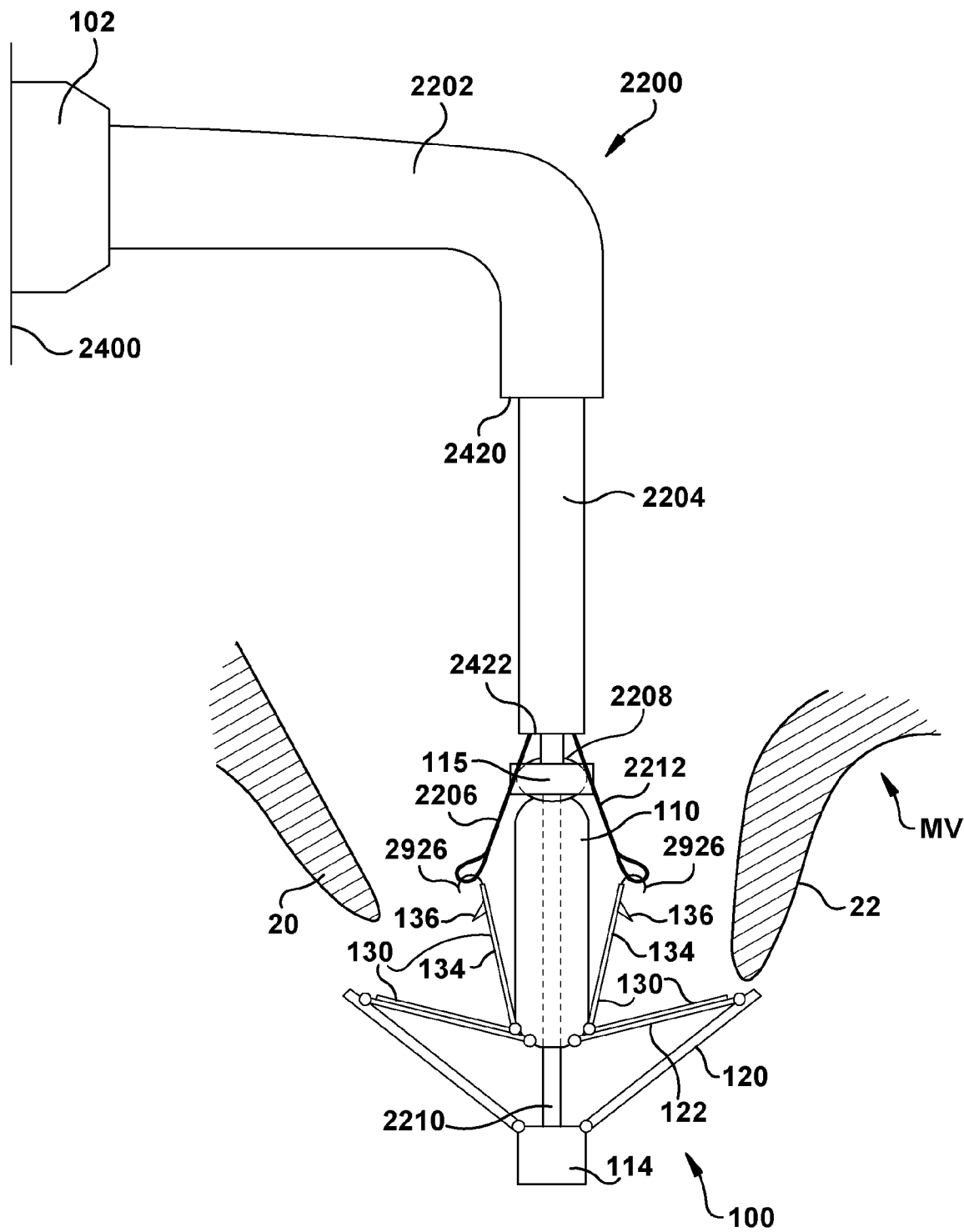
Figure 34:
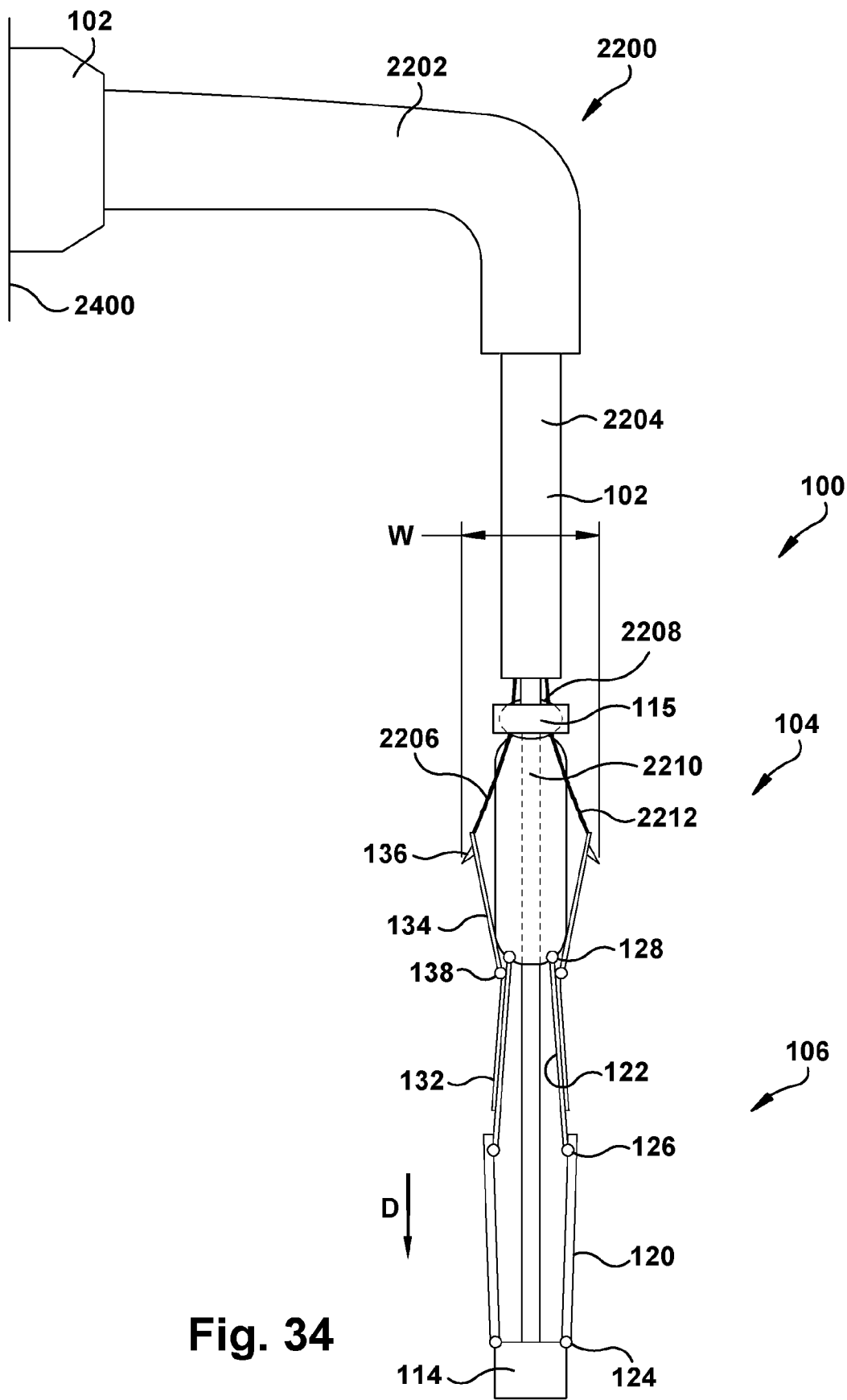

Referring to FIG. 33, after the barbs 136 of the gripping clasps 130 are released from the leaflets 20, 22, the device 100 is no longer engaged with the mitral valve MV. Referring to FIG. 34, after the device 100 is no longer engaged with the mitral valve MV, the device 100 is moved to the elongated and fully open position, which places the device 100 in a position having its smallest width W (to provide for an easier removal of the device 100). The device 100 is moved to the fully open position by further movement of the actuation member 2210 in the direction D, which causes the cap 114 to move in the direction D. This movement of the cap 114 in the direction D until the cap 114 reaches a fully open state causes the device to be in the fully open position (as described herein with reference to FIGS. 8-14).

After the device 100 is in the fully open position the retrieval shaft 2204 and the device 100 are retracted into the sheath. Then, the sheath 102 containing the retrieval device 2200, and the device 100, are removed from the patient's heart.

Figure 58:
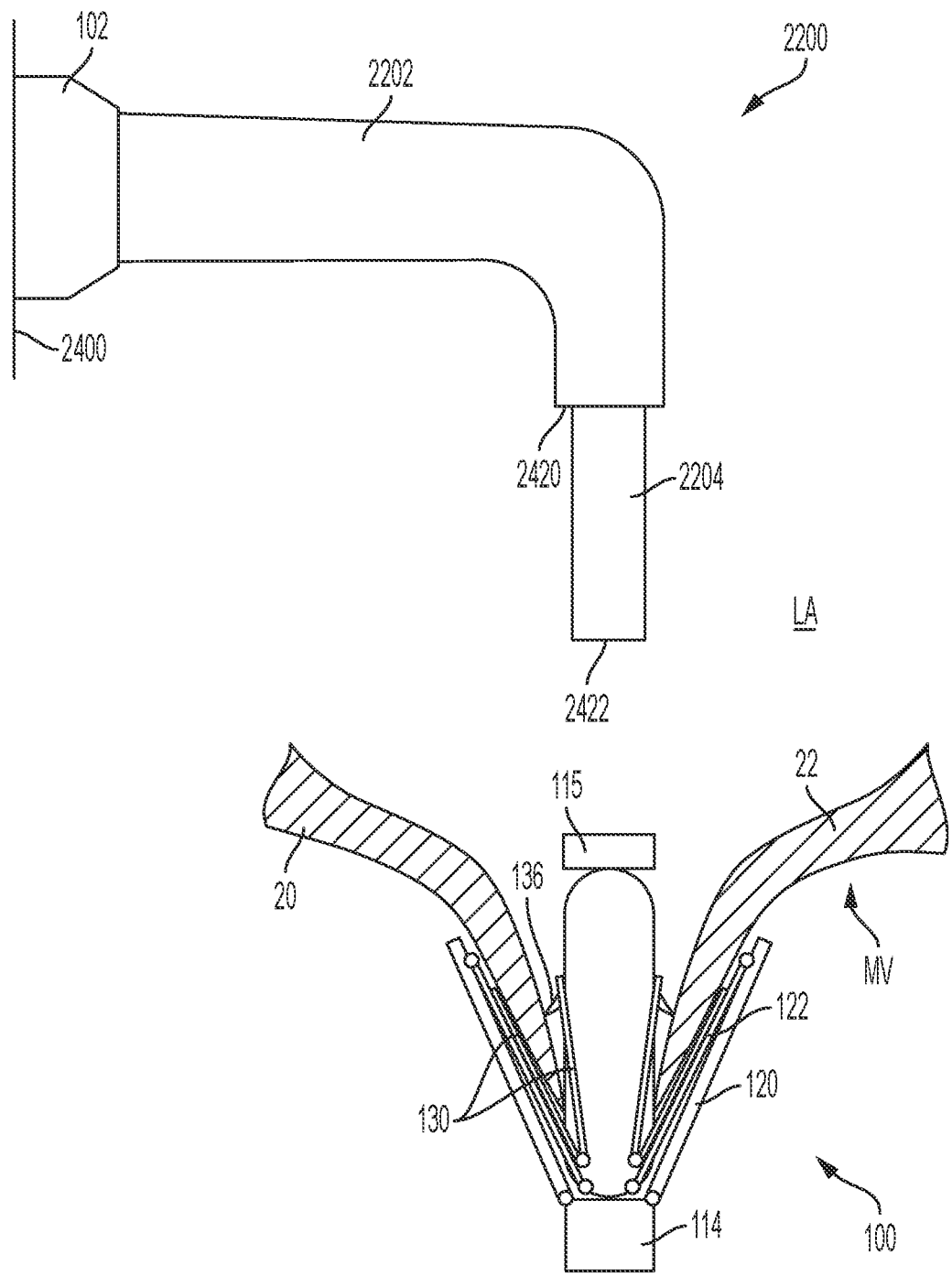
FIGS. 58-66 show the example retrieval device of FIG. 22 being positioned to engage and engaging the implanted prosthetic device of FIG. 21 to remove the implanted prosthetic device from a native valve, according to an example method.
Figure 59:
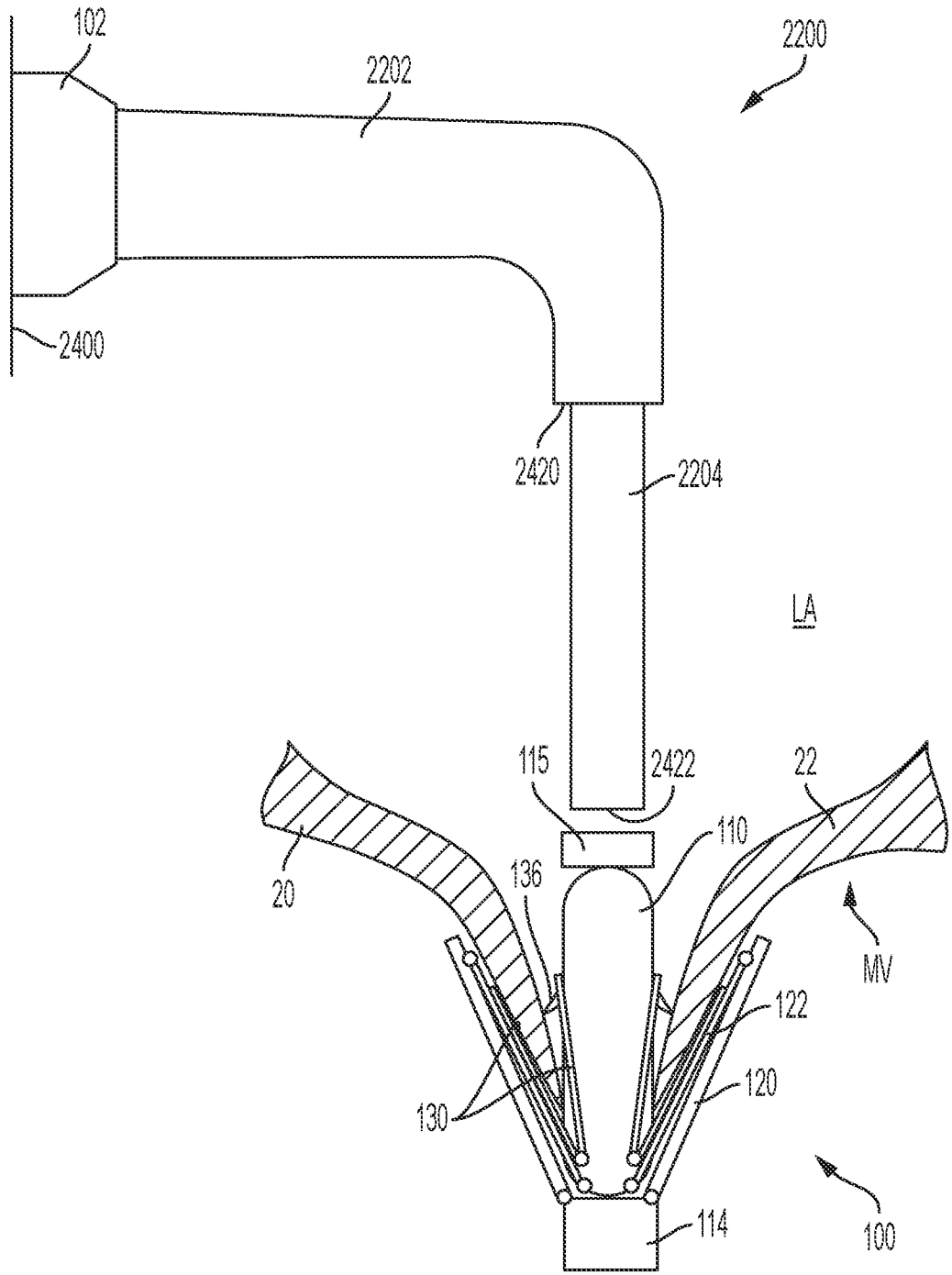

Referring now to FIGS. 58-66, the retrieval device 2200 is shown being positioned to engage an implanted device 100 on a native valve, e.g., the native mitral valve MV in this example, and engaging the implanted device 100 to remove the implanted device from the native valve, according to an example embodiment. Referring to FIGS. 58 and 59, the retrieval device 2200 is shown extending through the septum 2400 of a heart such that the retrieval device 2200 is positioned in the left atrium LA of the heart. In certain embodiments, a delivery sheath 102 is used to deliver the retrieval device 2200 to the heart of a patient. The delivery sheath 102 can deliver the retrieval device to the patient's heart by any suitable means, such as, for example, by any means described in the present application regarding the delivering and implanting of the implantable device 100. After the sheath 102 is positioned in the left atrium LA, the catheter 2202 can be configured to be steerable such that the distal end 2420 can be positioned above the implanted device 100. Referring to FIG. 59, after the distal end 2420 of the catheter 2202 is positioned above the implanted device 100, the retrieval shaft 2204 can be extended out of a distal end 2420 of the catheter 2202 to position the one or more components (2206, 2208, 2210, 2212) to engage and retrieve the implanted device 100. In certain embodiments, the distal end 2422 of the retrieval shaft 2204 is positioned near the collar 115 of the device 100.

Figure 60:
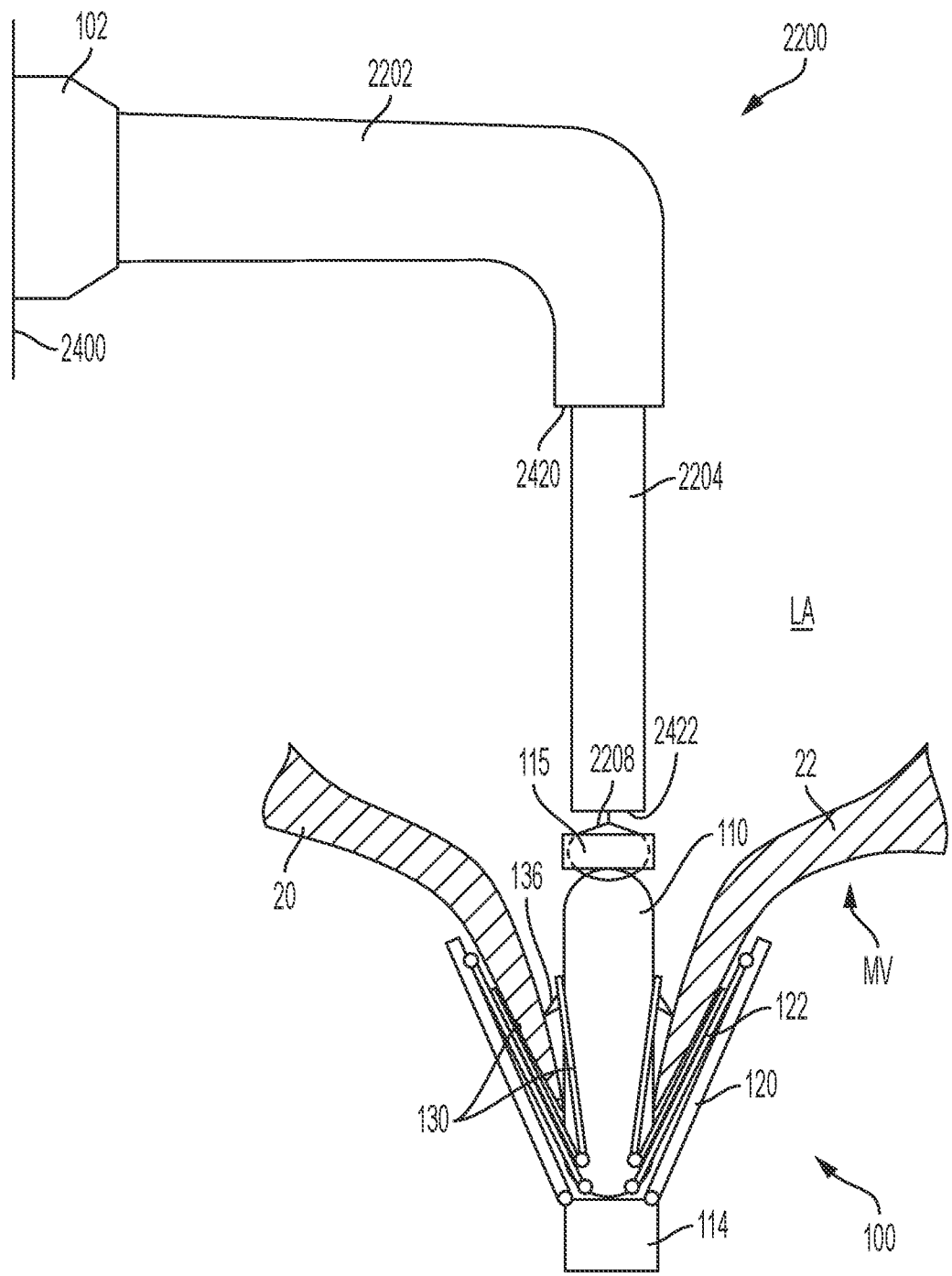

Referring to FIG. 60, once the distal end 2422 of the retrieval shaft 2204 is positioned near or in contact with the collar 115 of the device 100, the securing member 2208 is configured to be extended from the retrieval shaft 2204 and engage the collar 115 to secure the retrieval device 2200 to the implanted device 100. In the illustrated embodiment, the securing member 2208 is a snare having a wire loop, in which the wire loop is configured to extend around the collar 115. The securing member 2208 can, however, take any suitable form, such as, for example, a clip, a magnet, a detent mechanism, a coupler, a hook and loop connection, any frictional connection, a twist to lock type connection, any other form described with respect to securing members anywhere herein, or any other known fastening arrangement.

Figure 61:
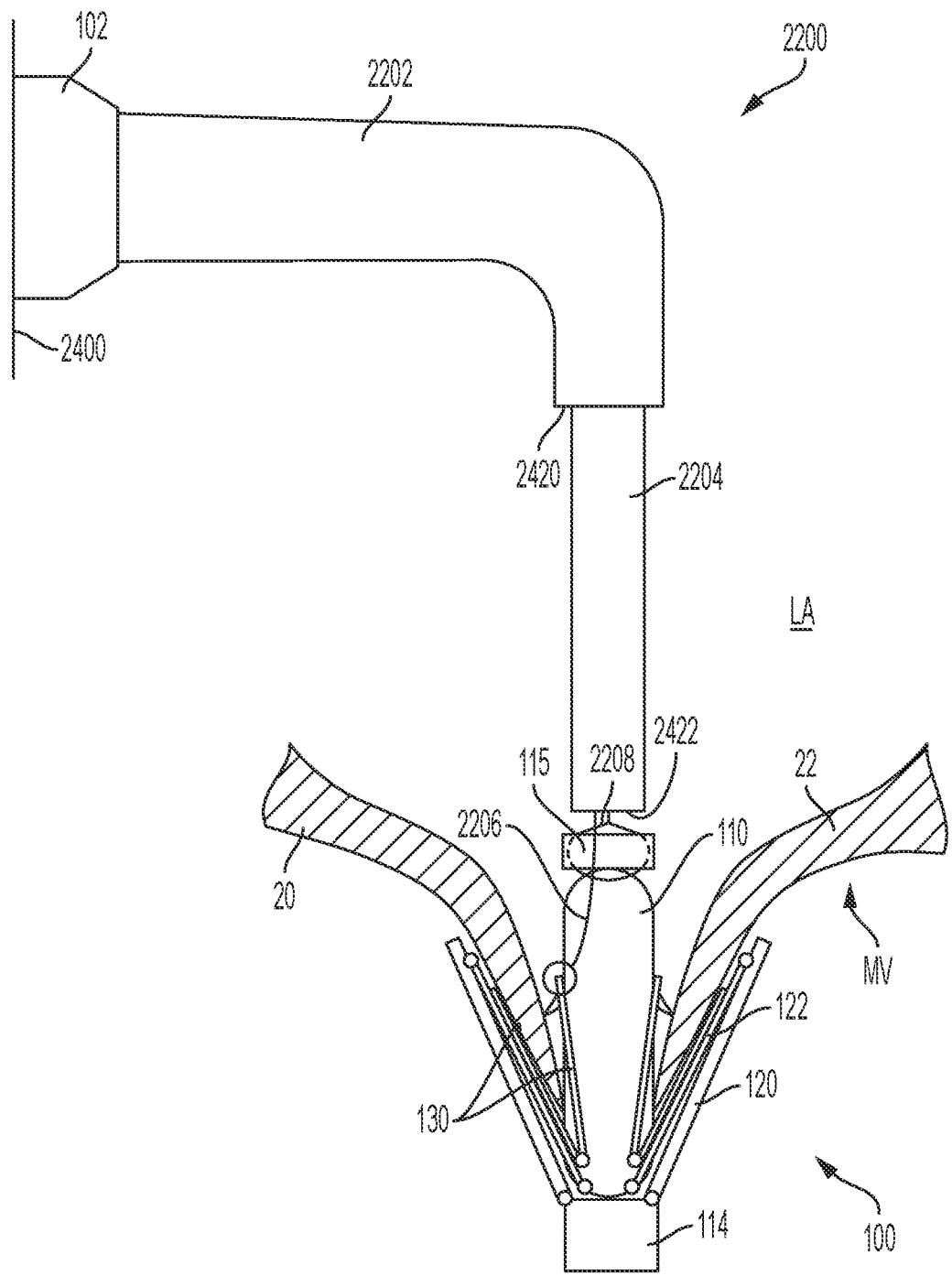
Figure 62:
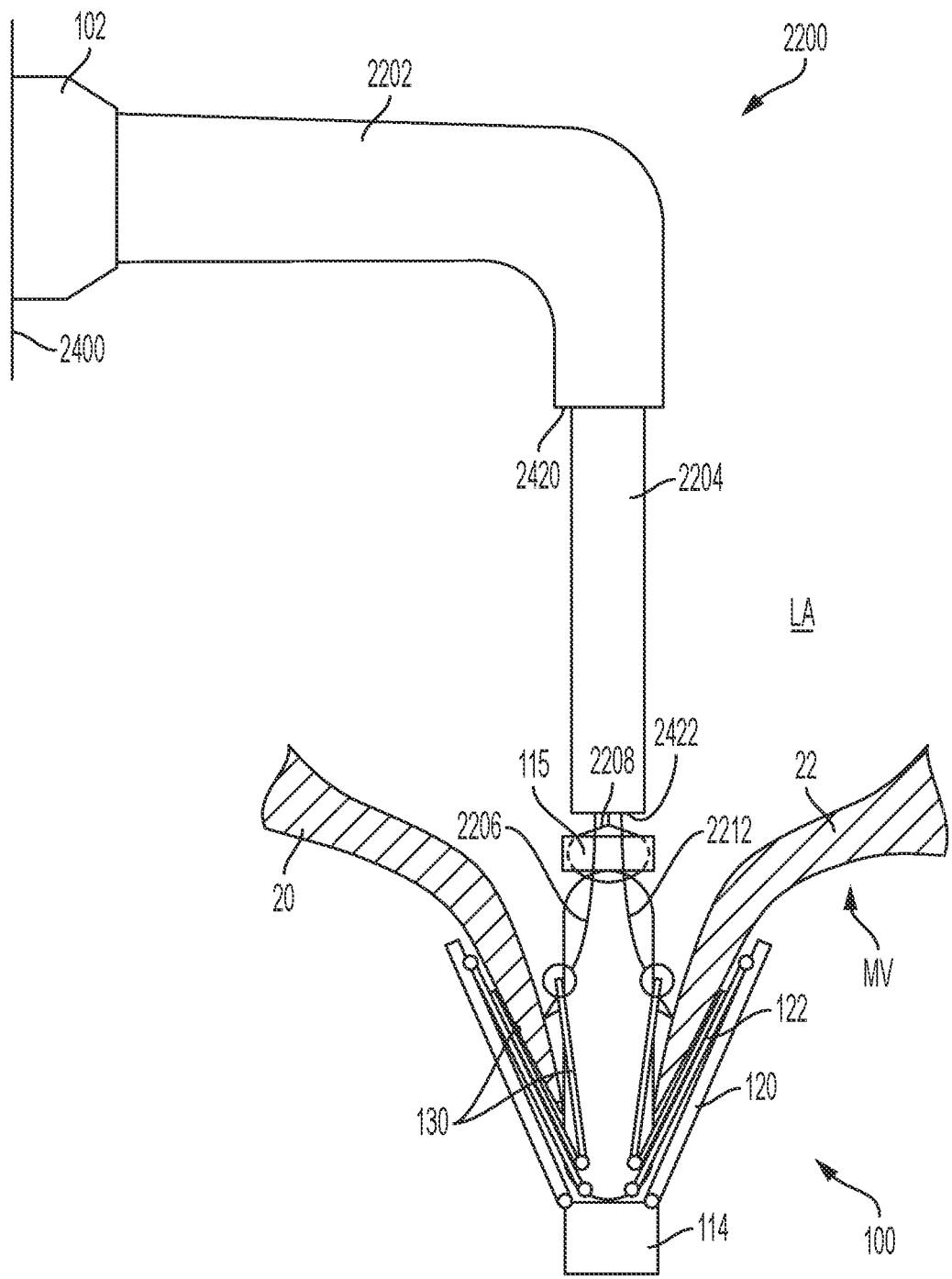

Referring to FIGS. 61 and 62, the first capturing member 2206 is extended from the distal end 2422 of the retrieval shaft 2204 and attached to one of the gripping clasps 130, and the second capturing member 2212 is extended from the distal end 2422 of the retrieval shaft 2204 and attached to the other gripping clasp 130. In the illustrated embodiment, the capturing members 2206, 2212 are snares with a wire loop that are configured to attach the gripping clasps 130 (e.g., by an attachment member, such as attachment member 2926 shown in FIG. 29). The capturing members 2206, 2212 can, however, take any suitable form, such as, for example, a wire with a barb, a clip, a magnet, a detent mechanism, a coupler, a hook and loop connection, any frictional connection, a twist to lock type connection, any other form described with respect to capturing members anywhere herein, or any other known fastening arrangement that is configured to attach to the gripping clasps 130.

Figure 62A:
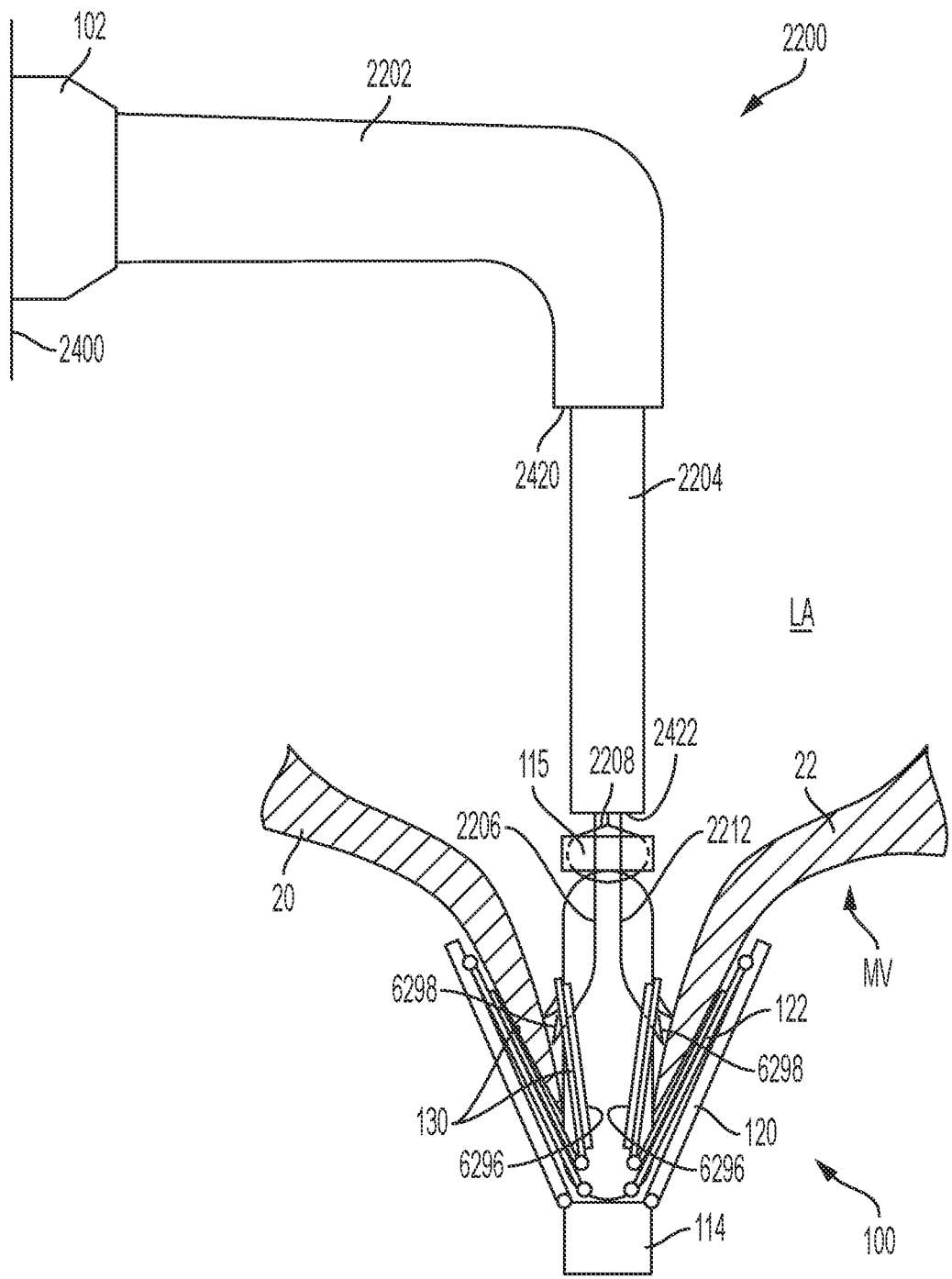
FIG. 62A is a view similar to FIG. 62 illustrating an embodiment where the clasps are at least partially made from or covered with a cloth material 6296 and the capturing members have at least one barb.

Referring to FIG. 62A, in certain embodiments, the clasps are at least partially made from a cloth material 6296, and the capturing members 2206, 2212 are wires with a barb 6298. In these embodiments, the capturing members 2206, 2212 are attached to the gripping clasps by piercing the cloth material with the barb 6298 of the capturing members 2206, 2212.

Figure 63:
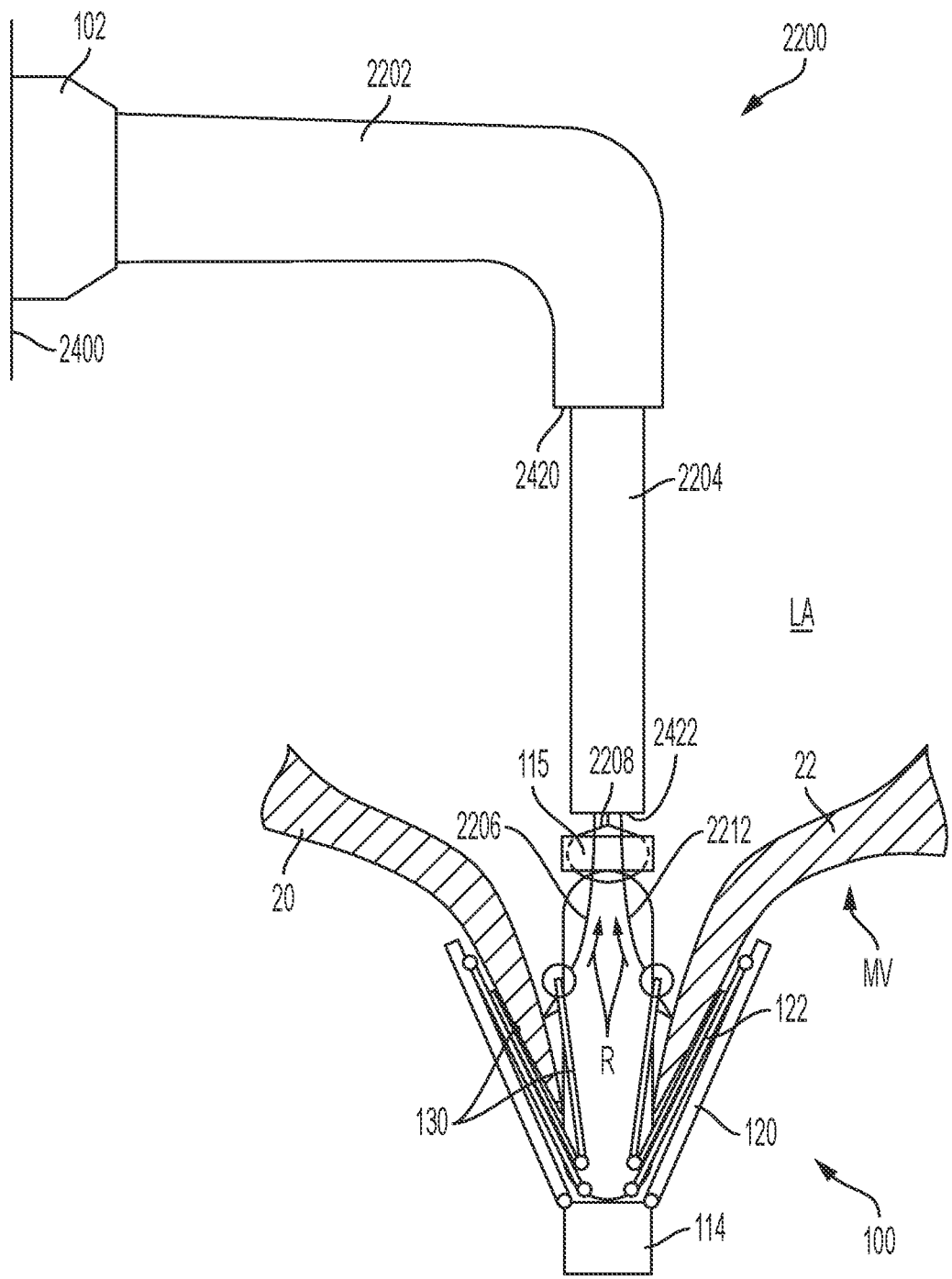
Figure 64:
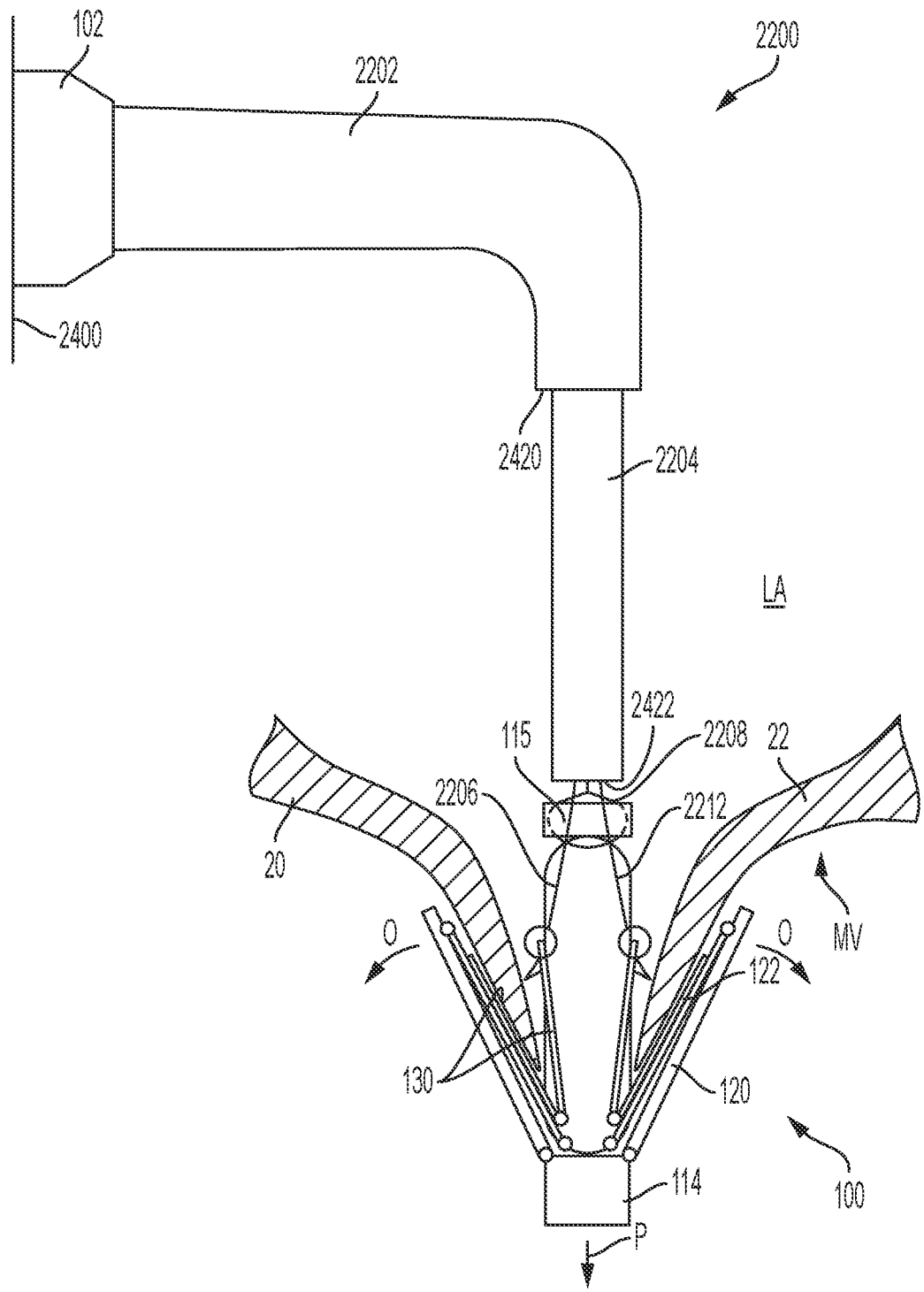
Figure 65:
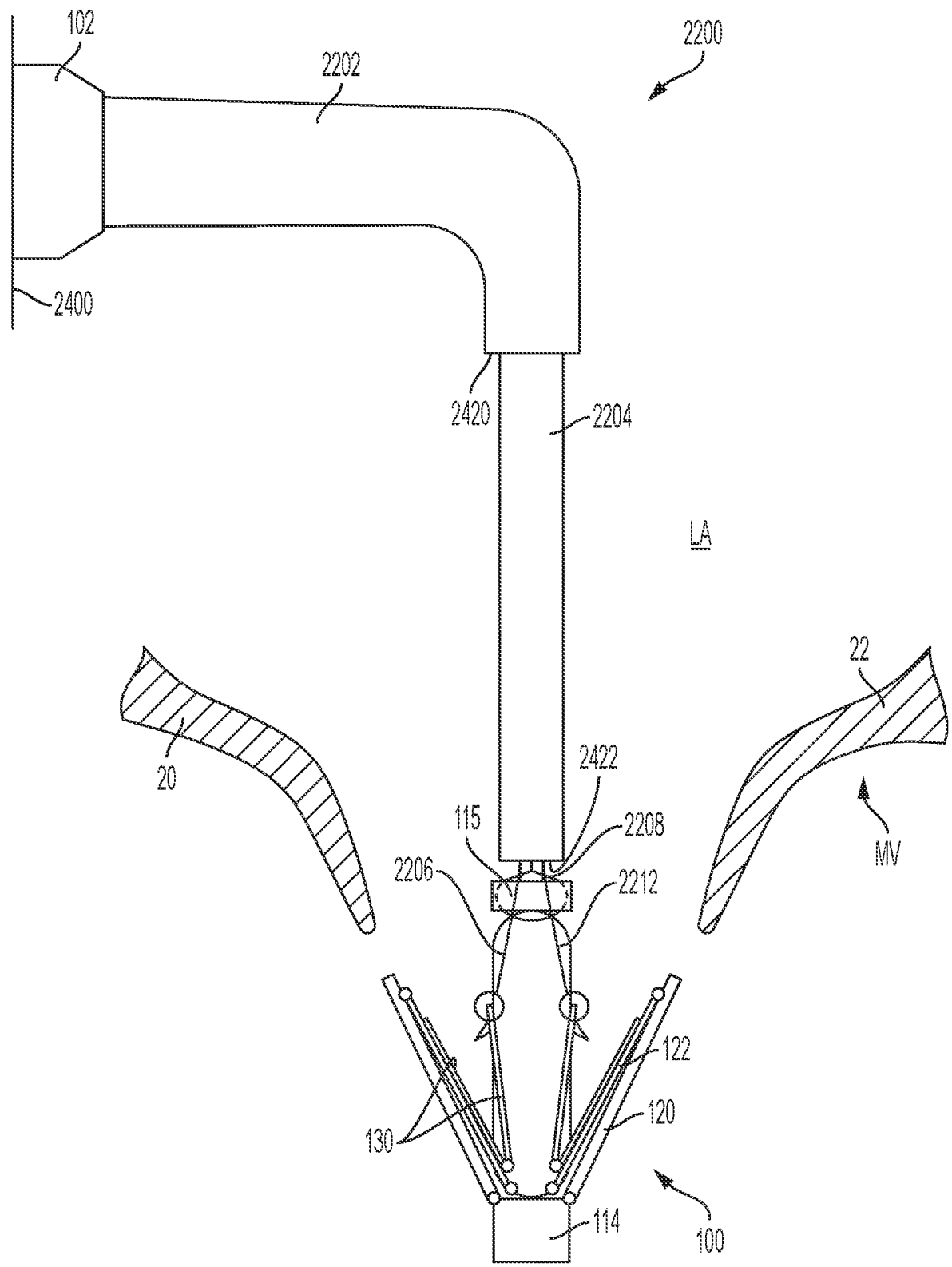

Referring to FIGS. 63 through 65, after the capturing members 2206, 2212 of the retrieval device 2200 are attached to the gripping clasps 130 of the implanted device 100, the capturing members 2206, 2212 are configured to provide a tension force to the movable arms 134 of the gripping clasps 130 to release the barbs 136 from the valve tissue of the leaflets 20, 22. For example, the capturing members 2206, 2212 can be pulled toward and/or into the retrieval shaft 2204 in the direction R (as shown in FIG. 63) to release the barbs 136 from the native valve (as shown in FIG. 64). Referring to FIGS. 63 and 64, in some embodiments, the movement of the capturing members 2206, 2212 in the direction R causes the paddles 120 of the implanted device 100 to move in an outward direction O. After the barbs are removed from the native valve, the implanted device 100 is moved in a downward direction P (as shown in FIG. 64) to a position below the native valve (as shown in FIG. 65) such that the implanted device is completely disengaged from the native valve.

Figure 66:
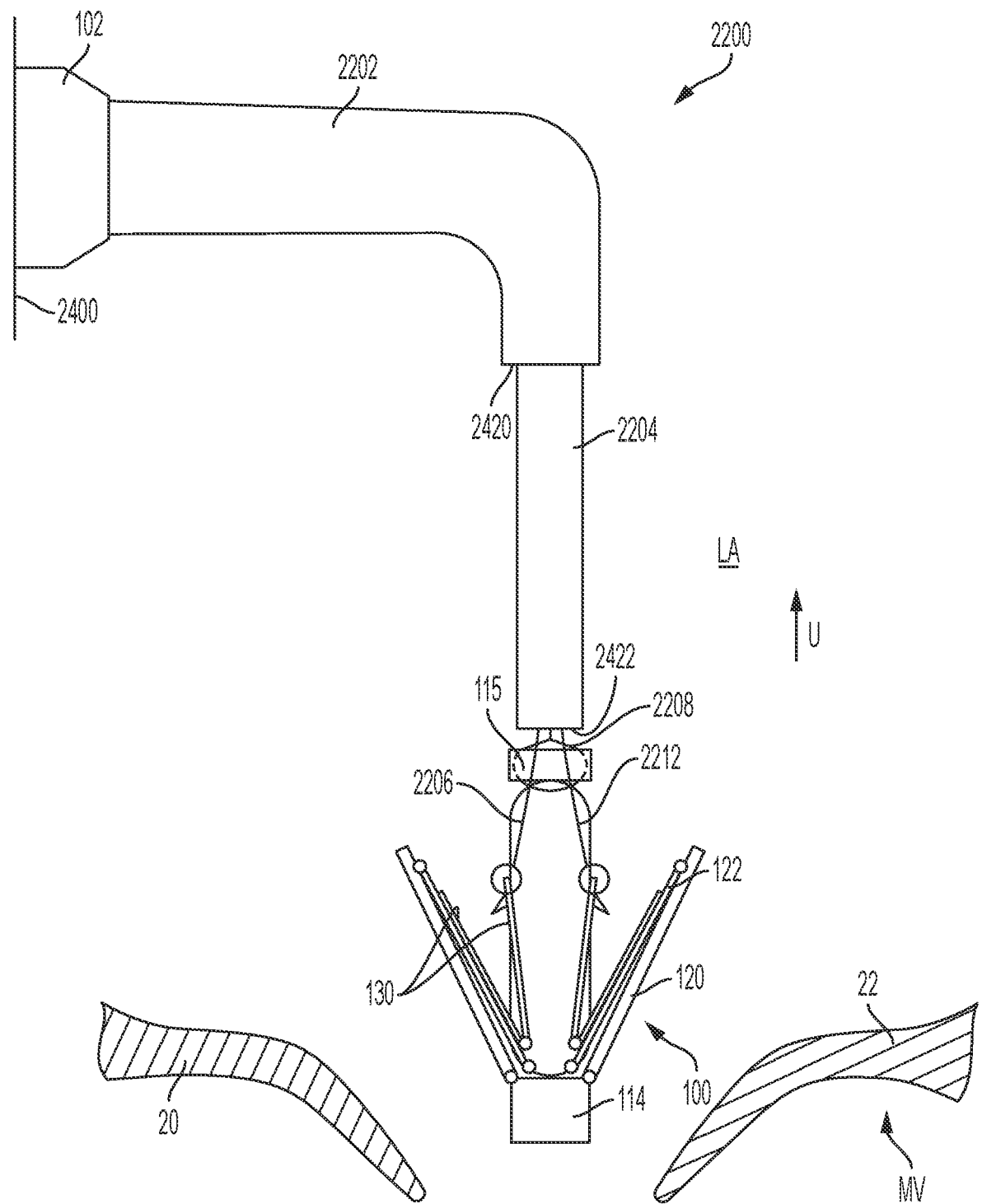

Referring to FIG. 66, after the device is removed from the native valve, the implanted device 100 is moved in the upward direction U to remove the implanted device from the heart of the patient. In certain embodiments, the retrieval device 2200 and the implanted device 100 are retracted into the sheath 102, and the sheath 102 (containing the retrieval device 2200 and the implanted device 100) is removed from the patient's heart.

Figure 67:
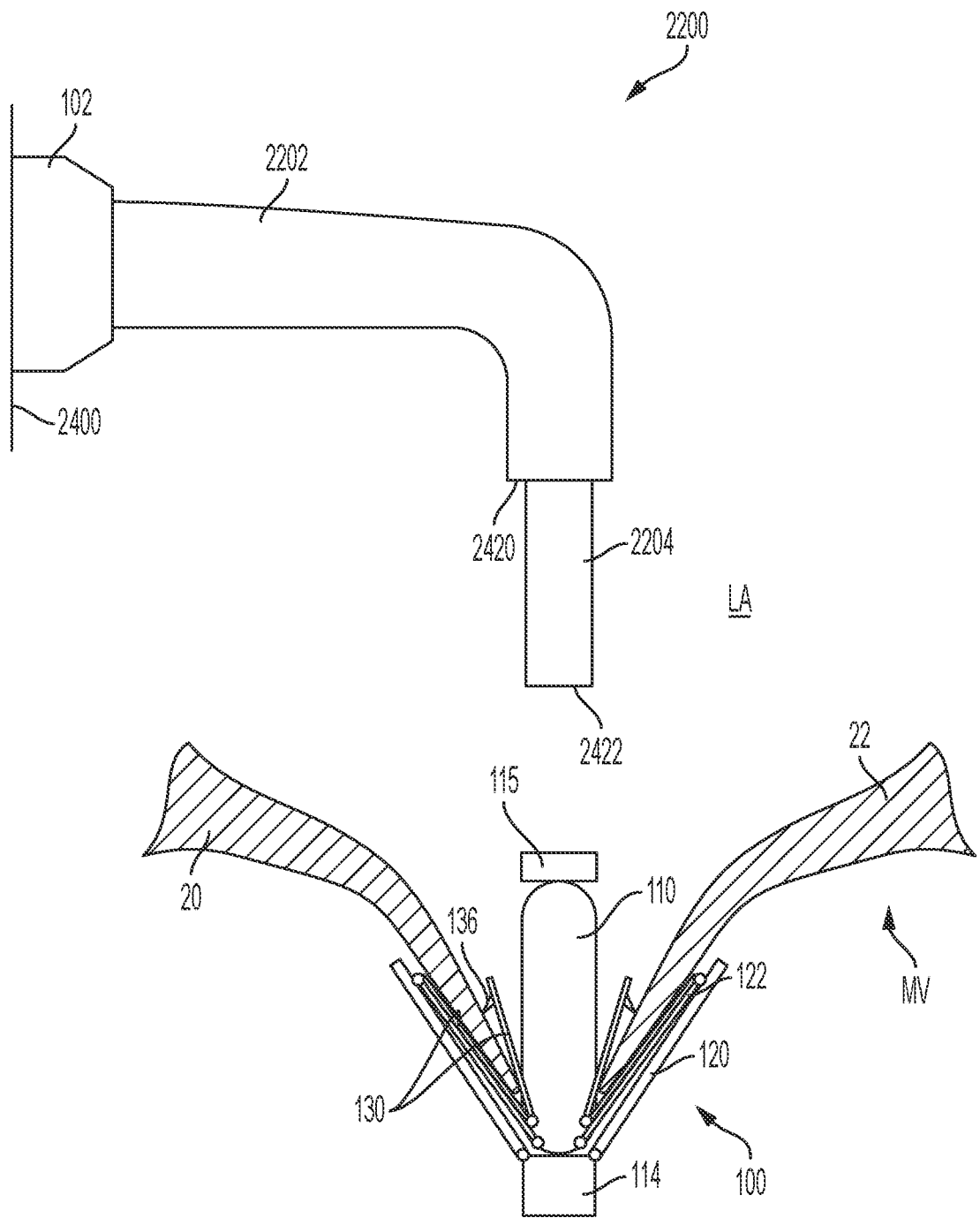
FIGS. 67-77 show the example retrieval device of FIG. 22 being positioned to engage and engaging the implanted prosthetic device of FIG. 21 to remove the implanted prosthetic device from the native valve, according to an example method.
Figure 68:
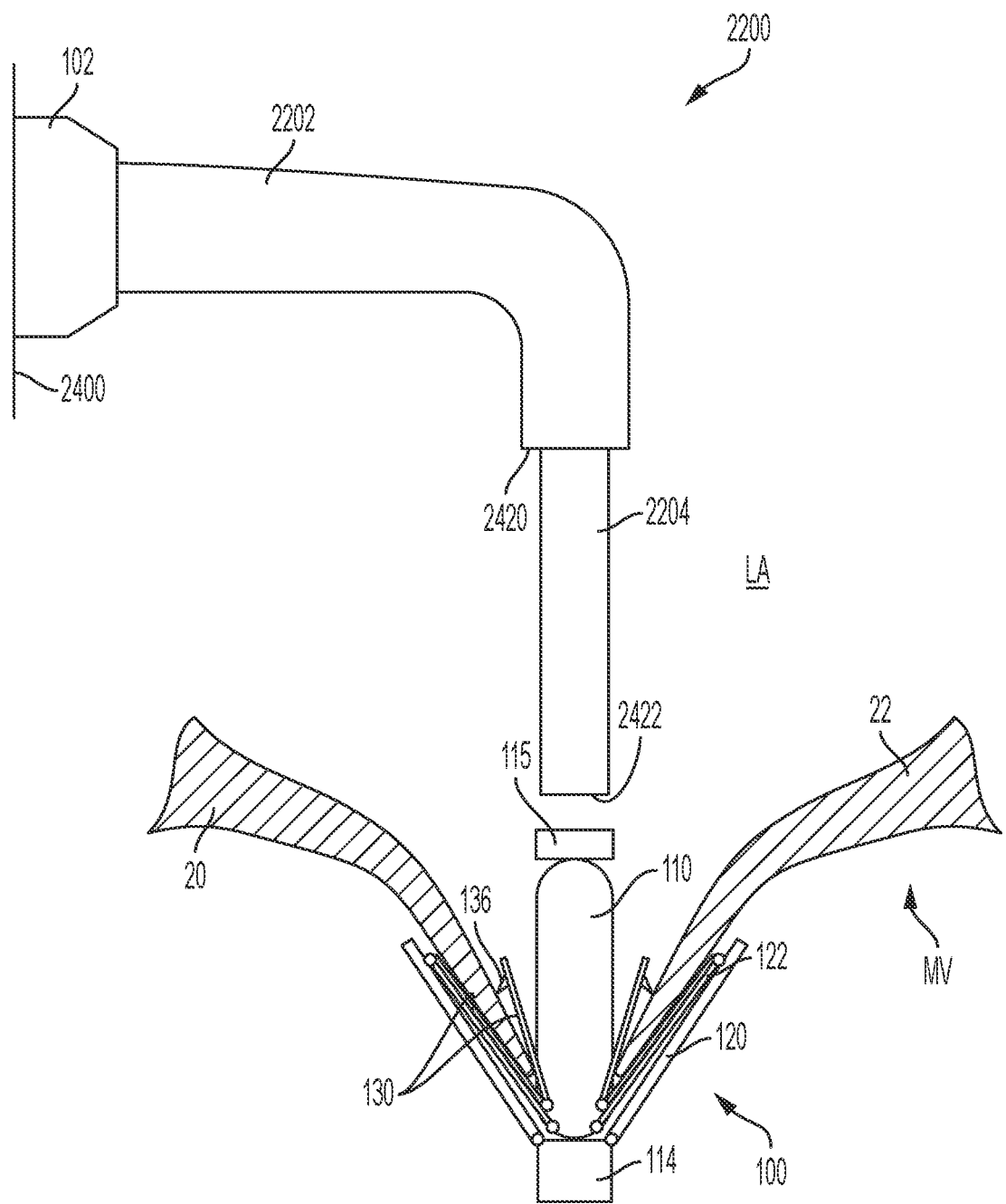

Referring now to FIGS. 67-77, the retrieval device 2200 is shown being positioned to engage an implanted device 100 on the native valve, or mitral valve MV in this example, and engaging the implanted device 100 to remove the implanted device from the native valve, according to an example embodiment. Referring to FIGS. 67 and 68, the retrieval device 2200 is shown extending through the septum 2400 of a heart such that the retrieval device 2200 is positioned in the left atrium LA of the heart. In certain embodiments, a delivery sheath 102 is used to deliver the retrieval device 2200 to the heart of a patient. The delivery sheath 102 can deliver the retrieval device to the patient's heart by any suitable means, such as, for example, by any means described in the present application regarding the delivering and implanting of the implantable device 100. After the sheath 102 is positioned in the left atrium LA, the catheter 2202 can be configured to be steerable such that the distal end 2420 can be positioned above the implanted device 100. Referring to FIG. 68, after the distal end 2420 of the catheter 2202 is positioned above the implanted device 100, the retrieval shaft 2204 can be extended out of a distal end 2420 of the catheter 2202 to position the one or more components (2206, 2208, 2210, 2212) to engage and retrieve the implanted device 100. In certain embodiments, the distal end 2422 of the retrieval shaft 2204 is positioned near the collar 115 of the device 100.

Figure 69:
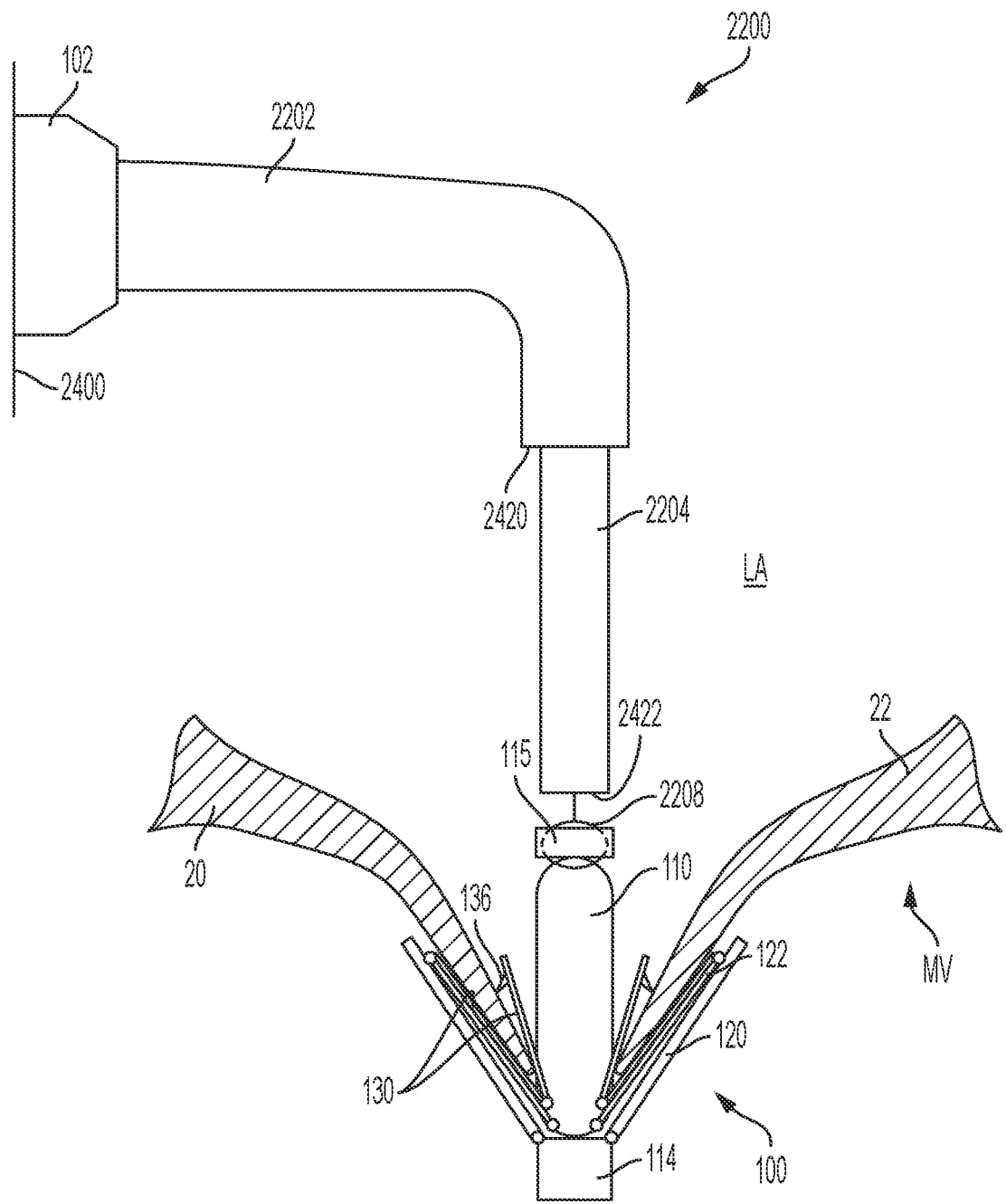

Referring to FIG. 69, once the distal end 2422 of the retrieval shaft 2204 is positioned near or in contact with the collar 115 of the device 100, the securing member 2208 is configured to be extended from the retrieval shaft 2204 and engage the collar 115 to secure the retrieval device 2200 to the implanted device 100. In the illustrated embodiment, the securing member 2208 is a snare having a wire loop, in which the wire loop is configured to extend around the collar 115. The securing member 2208 can, however, take any suitable form, such as, for example, a clip, a magnet, a detent mechanism, a coupler, a hook and loop connection, any frictional connection, a twist to lock type connection, any other form described with respect to securing members anywhere herein, or any other known fastening arrangement.

Figure 70:
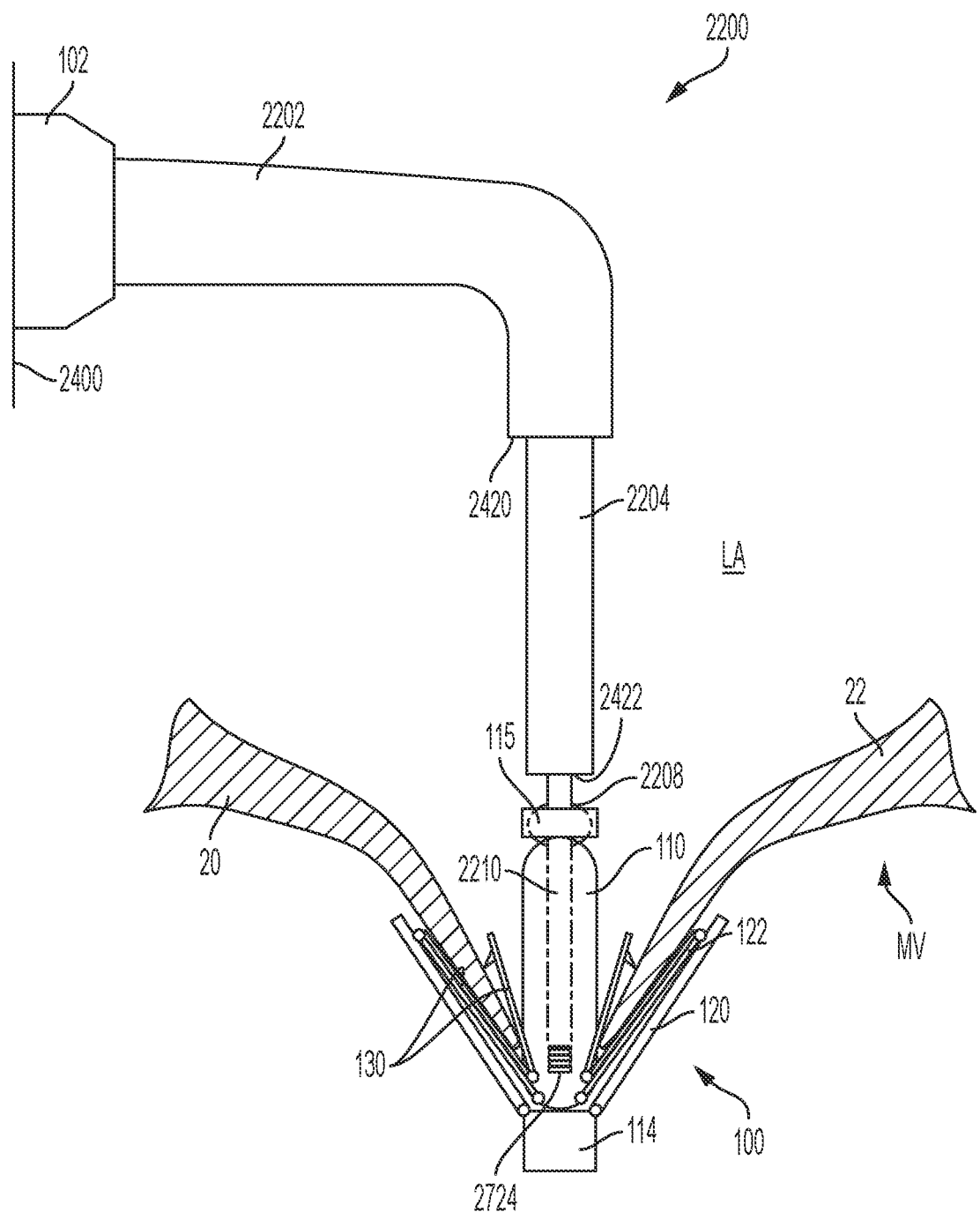
Figure 71:
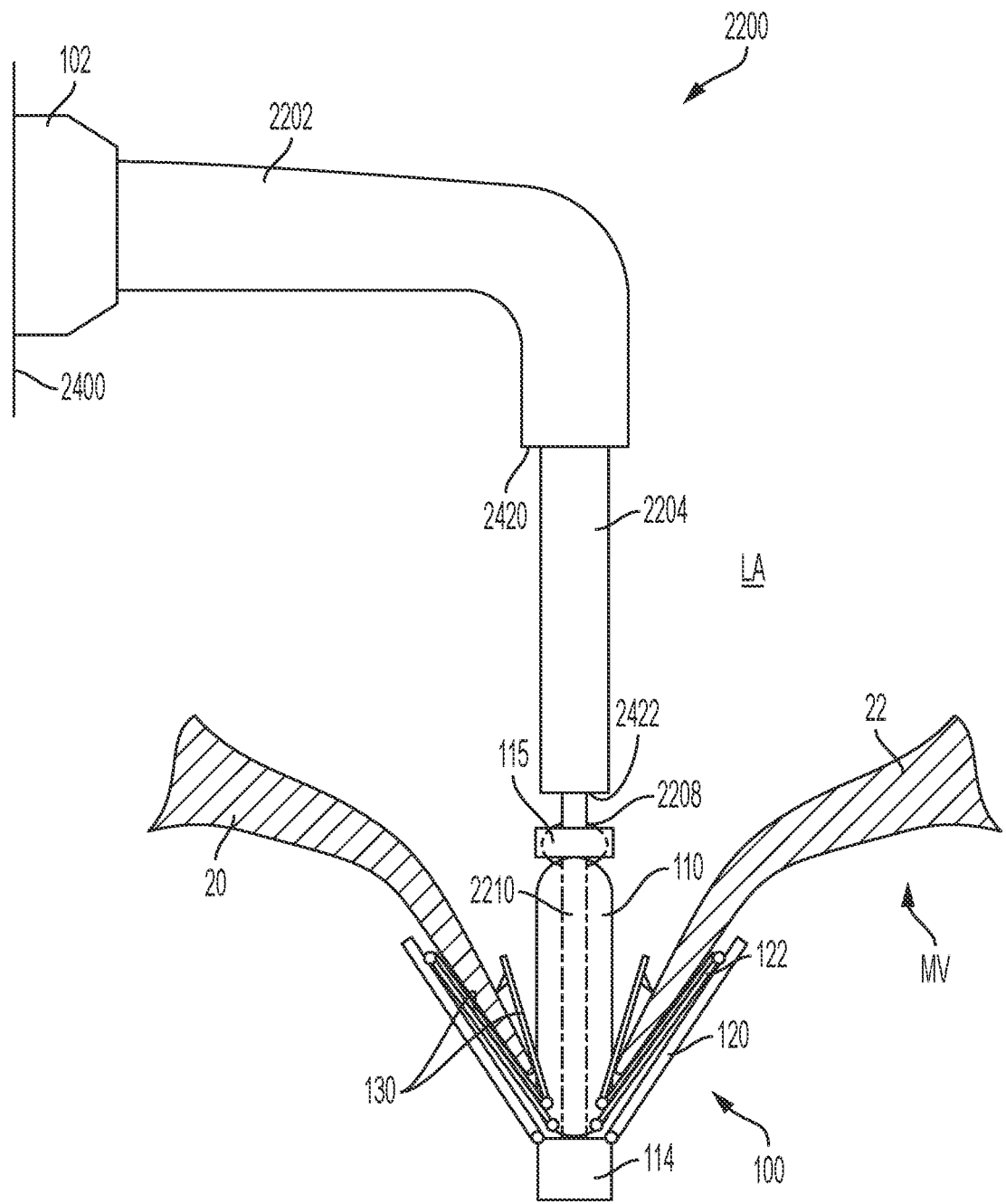

Referring to FIGS. 70 and 71, an actuation member/element 2210 is extended from the distal end 2422 of the retrieval shaft 2204 to engage the implanted device 100. The actuation member 2210 has a distal end 2724 that is configured to engage the cap 114. In some embodiments, the distal end 2724 of the actuation member 2210 is configured to be attached to the cap 114 (as shown in FIG. 71). For example, the actuation member 2210 and the cap 114 can be connected by a threaded connection, a snap-fit connection, a frictional connection, a magnetic connection, a twist and lock type connection, or any other suitable connection. In the illustrated embodiment, the actuation member 2210 is threaded such that rotation of the actuation member connects the actuation member to the cap 114 of the implanted device 100. The actuation member 2210 can, however, take a wide variety of different forms, such as, for example, any form described for actuation element 112 in FIGS. 8-14 or any other form described with respect to actuation members or actuation elements anywhere herein.

Figure 72:
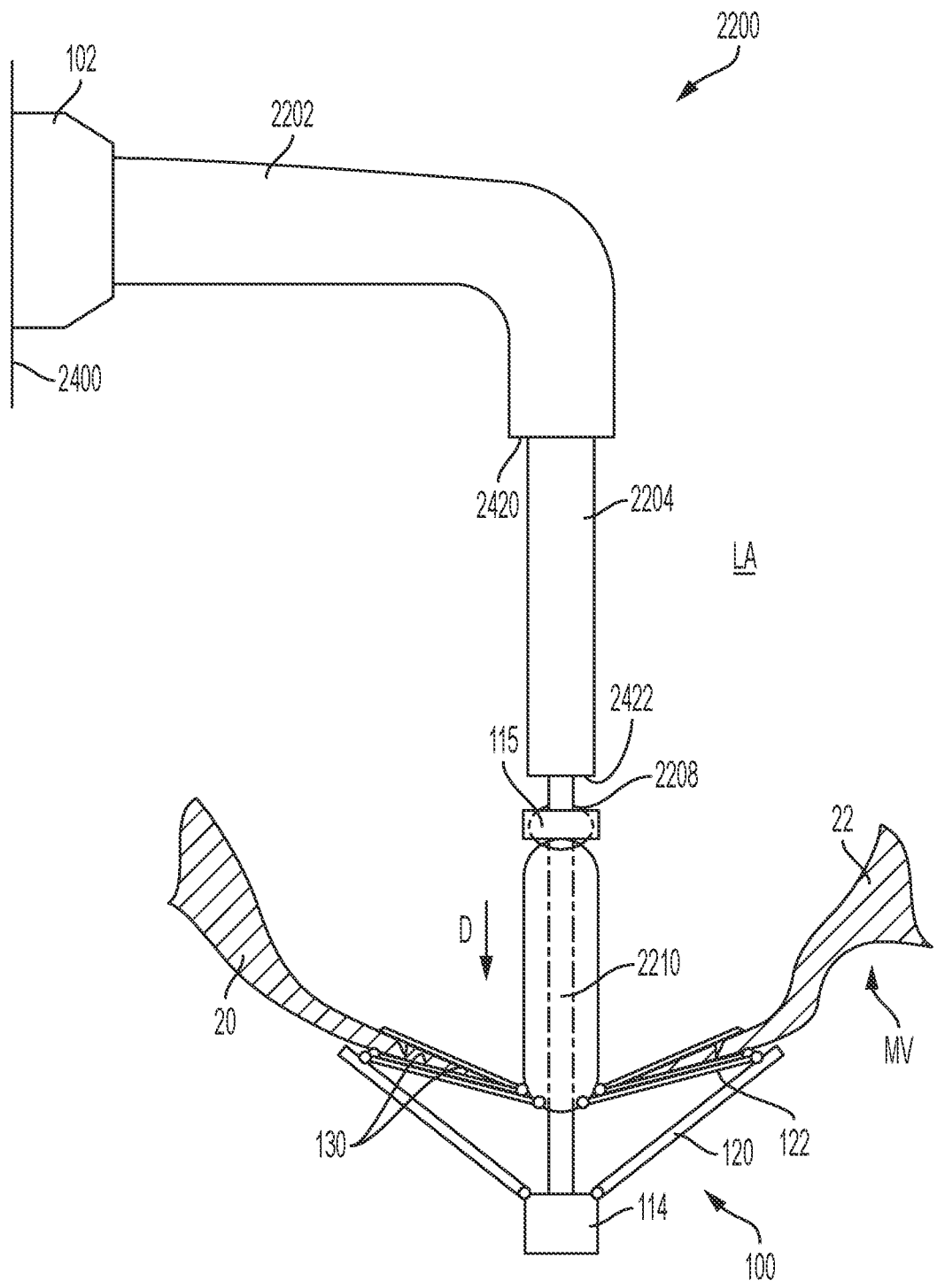

Referring to FIG. 72, the retrieval device 2200 is used to move the implanted device 100 to the partially opened position (as described above with reference to FIGS. 8-14) by moving the actuation member 2210 in the direction D while holding the position of the collar 115 with the securing member 2208 and/or the retrieval shaft 2204. The actuation member 2210 moves the cap 114 in the direction D.

Figure 73:
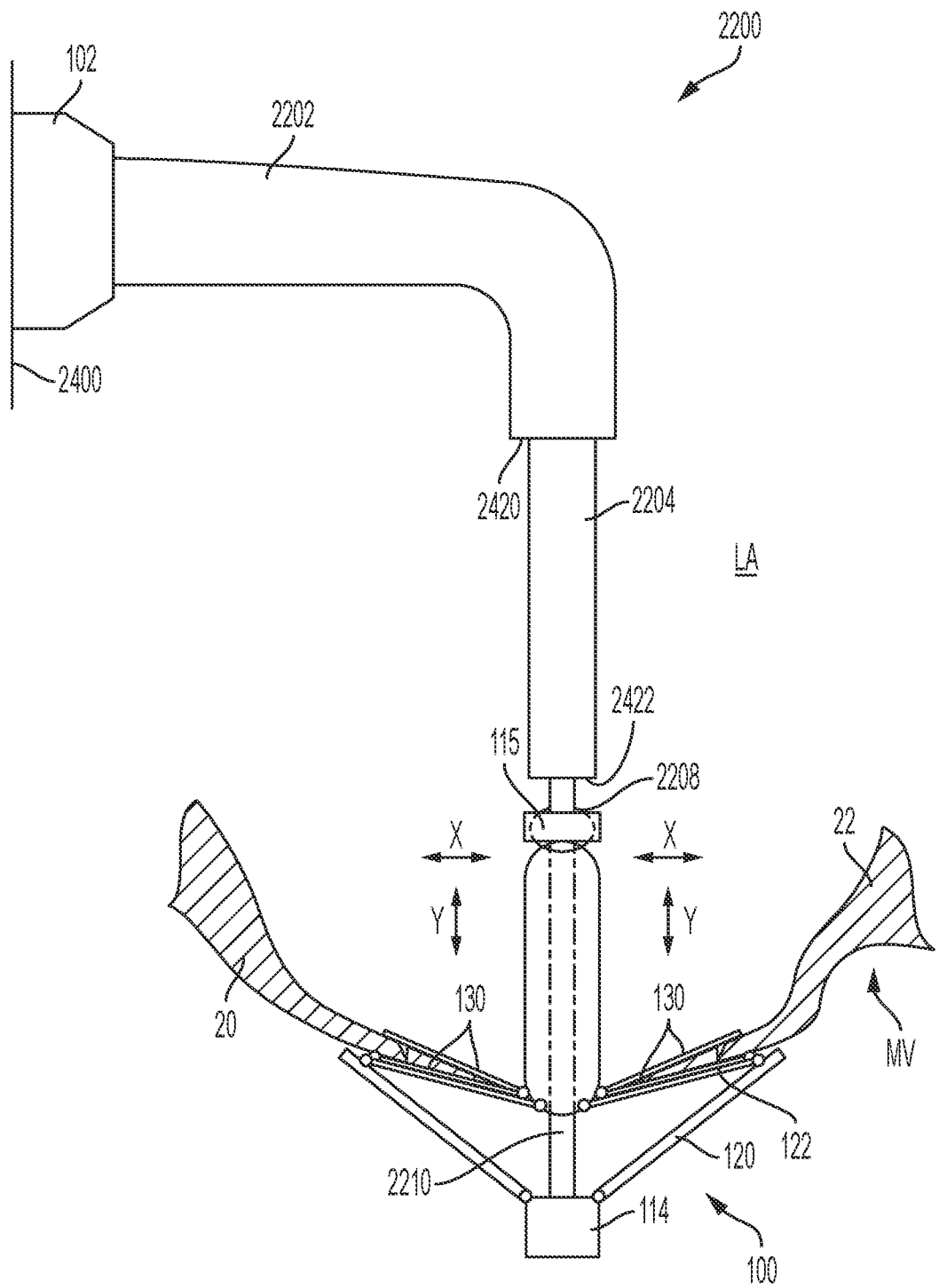
Figure 74:
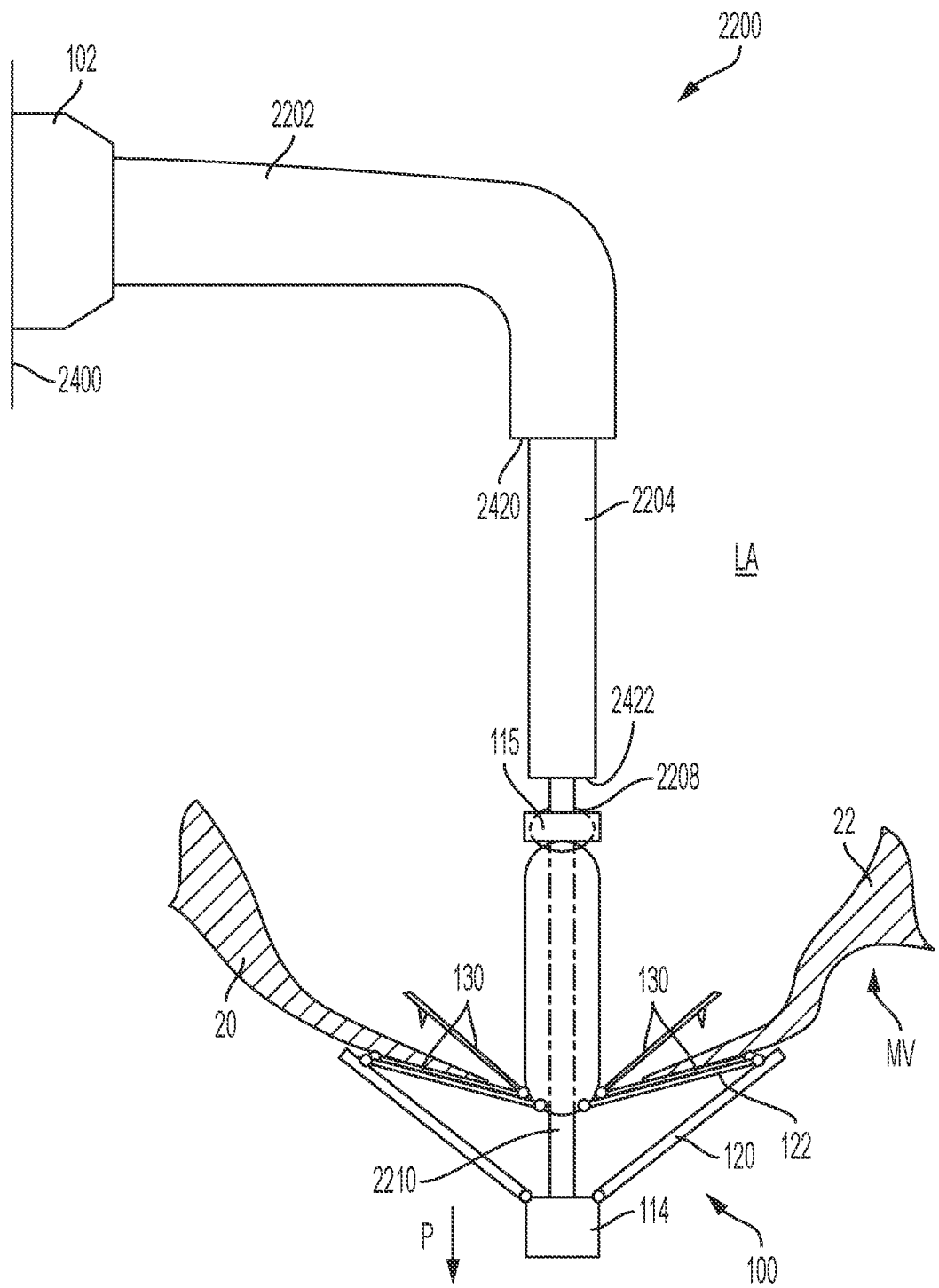
Figure 75:
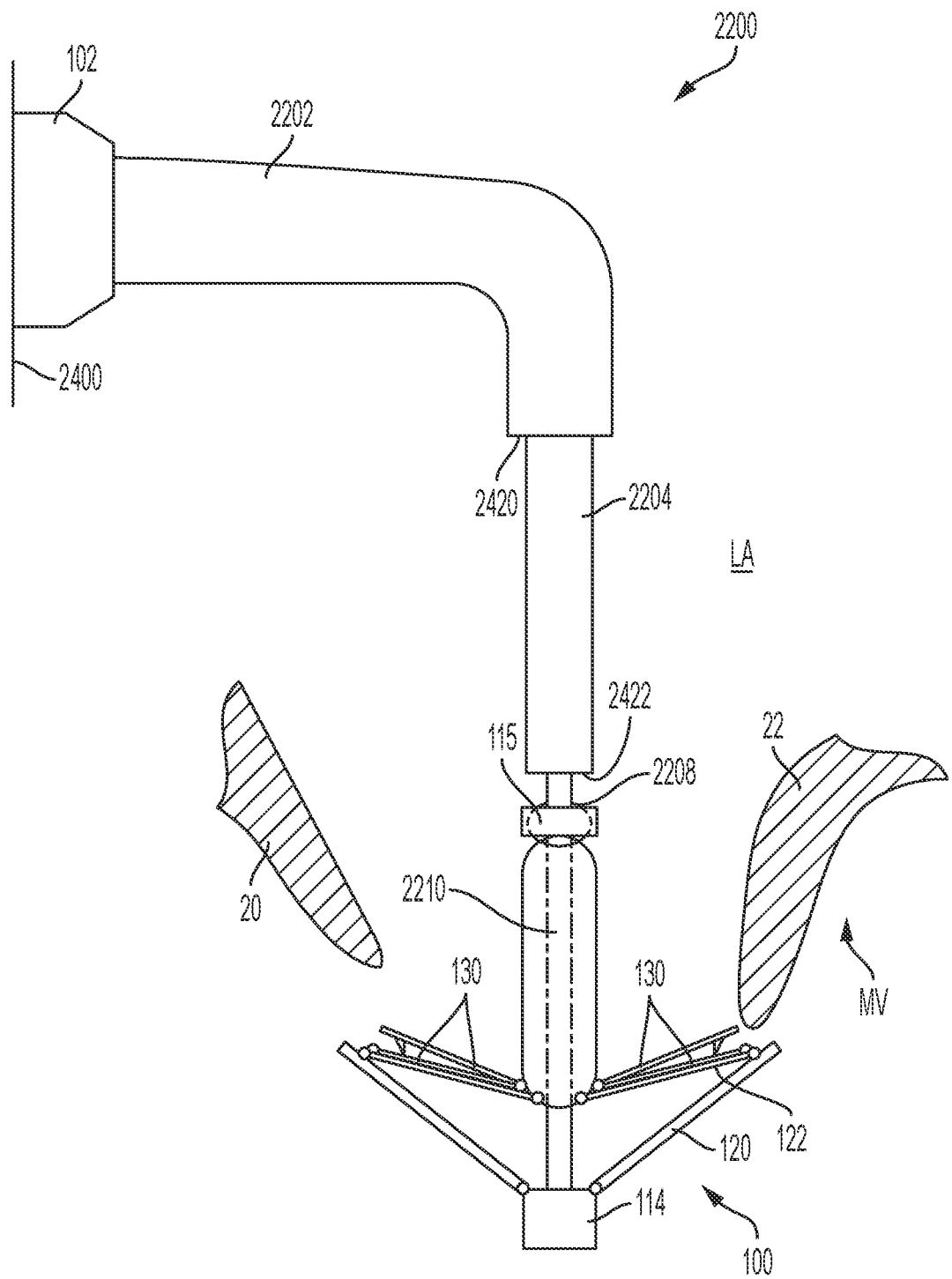

Referring to FIGS. 73 through 75, after the implanted device is moved to the partially opened position, the device 2200 is rapidly moved in the upward and downward directions Y and the side to side directions X (as shown in FIG. 73) to cause the gripping clasps 130 to release from the leaflets 20, 22 of the native valve (e.g., mitral valve MV, etc.). While FIG. 74 illustrates the clasps being partially open to illustrate release the leaflets, the leaflets can be released in a wide variety of different ways. For example, the clasps may simply shake or slide off of the leaflets when the device is opened and moved as illustrated by FIGS. 72 and 73, rather than the clasps being partially opened and spaced apart from the leaflets as illustrated by FIG. 74. After the gripping clasps 130 are removed from the native valve, the implanted device 100 is moved in a downward direction P (as shown in FIG. 74) to a position below the native valve (as shown in FIG. 75) such that the implanted device is completely disengages from the native valve.

Figure 76:
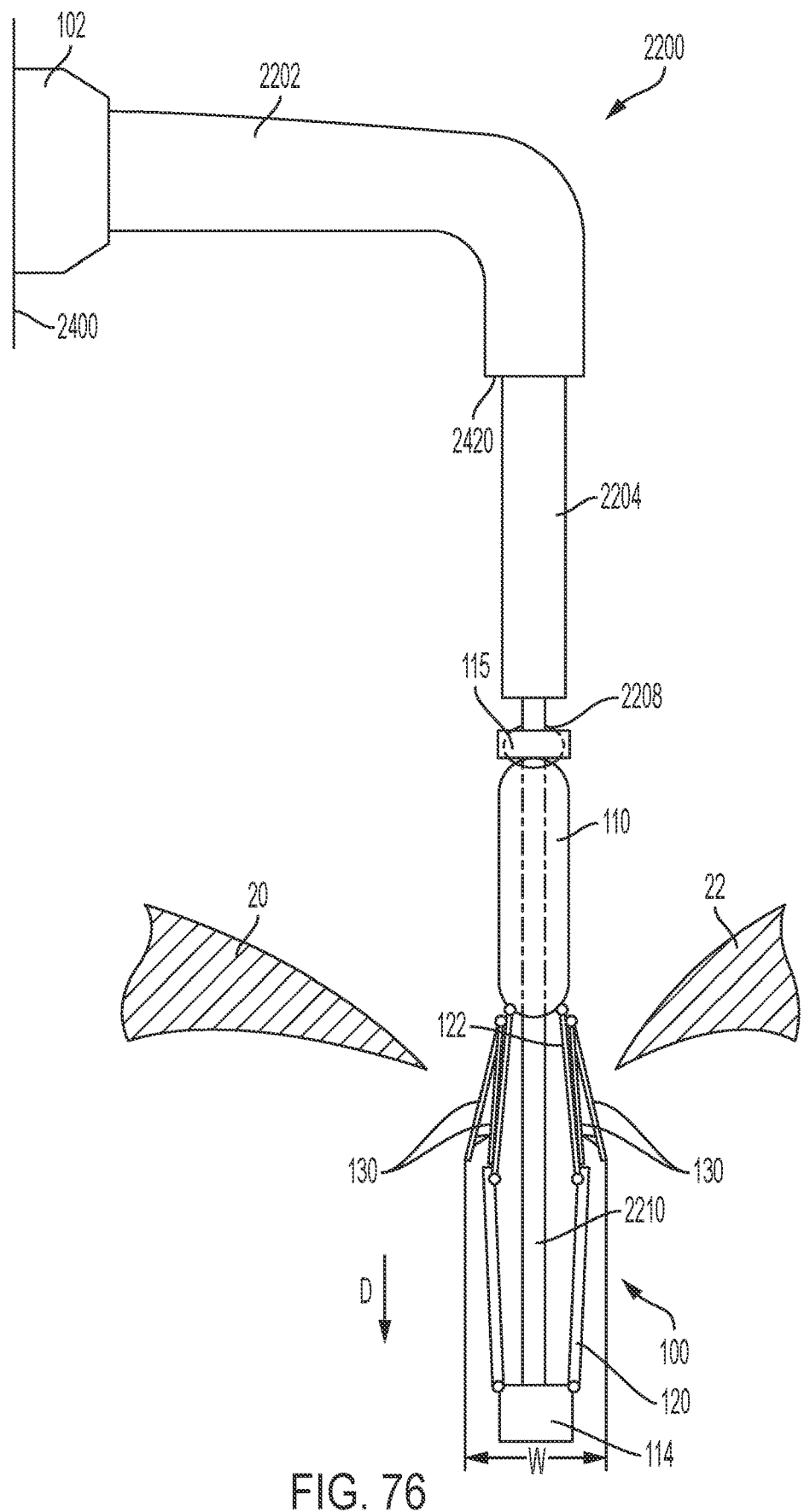

Referring to FIG. 76, after the device 100 is no longer engaged with the native valve, the device 100 can optionally be moved to the elongated and fully open position, which places the device 100 in a position having its smallest width W (to provide for an easier removal of the device 100). The device 100 is moved to the fully open position by further movement of the actuation member 2210 in the direction D, which causes the cap 114 to move in the direction D. This movement of the cap 114 in the direction D until the cap 114 reaches a fully open state causes the device to be in the fully open position (as described herein with reference to FIGS. 8-14). Also, the device can be moved to the fully open position to remove the device from the valve leaflets.

Figure 77:
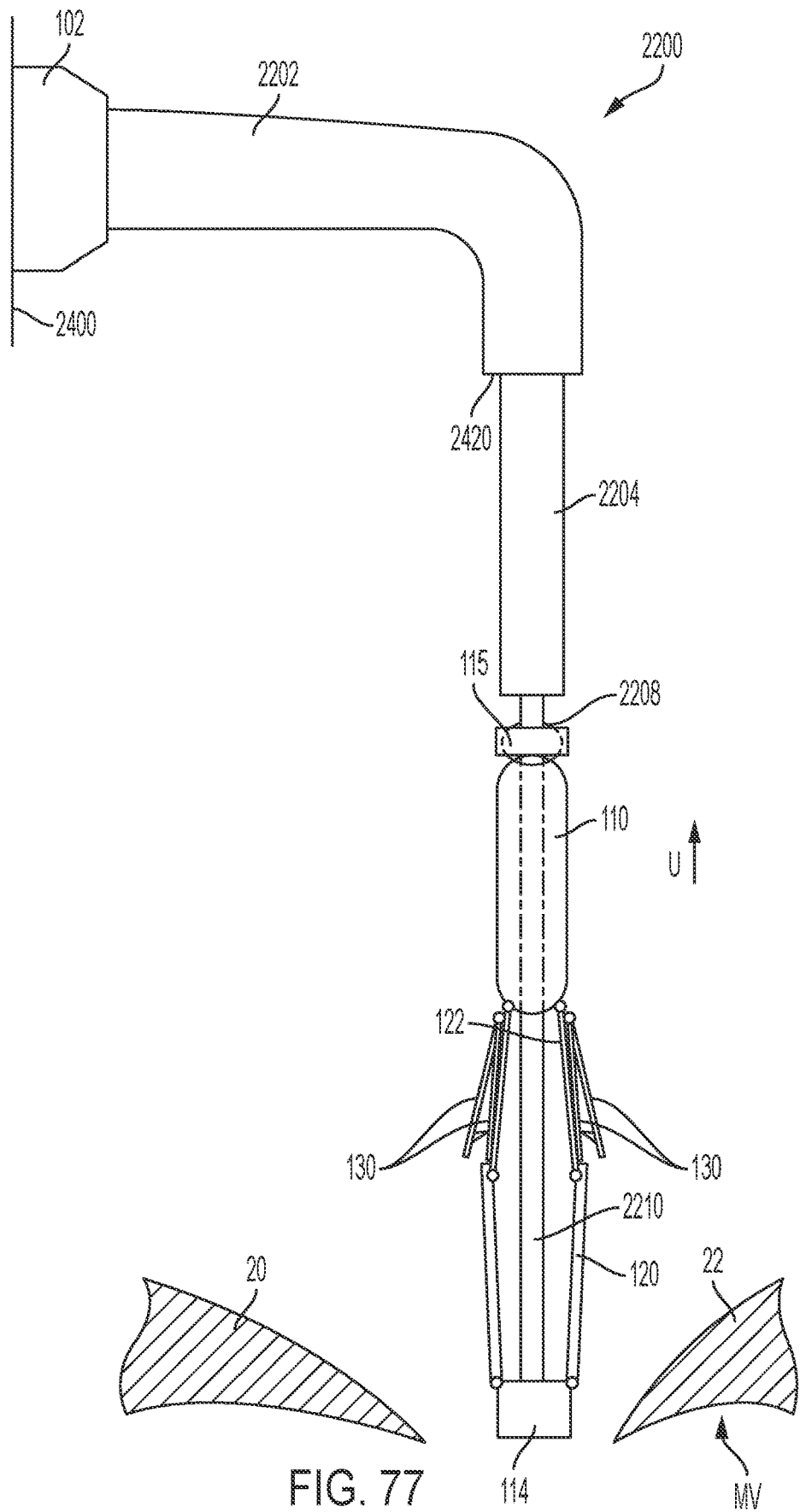

Referring to FIG. 77, the implanted device 100 is moved in the upward direction U to remove the implanted device from the heart of the patient. In the illustrated embodiment, the implanted device 100 is moved in the upward direction U after the device is moved to a fully open state. In other embodiments, the implanted device can be moved in the upward direction U without moving the implanted device to the fully open state. In certain embodiments, the retrieval device 2200 and the implanted device 100 are retracted into the sheath 102, and the sheath 102 (containing the retrieval device 2200 and the implanted device 100) is removed from the patient's heart.

Referring now to FIGS. 39-42, an example embodiment of a retrieval device 2200 is shown that is configured to remove and retrieve a device that was previously implanted within a patient's native valve (e.g., implanted device 100 shown in FIGS. 8-14 and 21). The previously implanted device can be retrieved after it has been implanted for various periods of time. In some embodiments, the retrieval device 2200 can be used to retrieve a device 100 that has been implanted within a patient's native valve for one month or less, such as 30 days or less, such as 25 days or less, such as 20 days or less, such as 15 days or less, such as 10 days or less, such as seven days or less, such as six days or less, such as five days or less, such as four days or less, such as three days or less, such as two days or less, such as one day or less, such as 20 hours or less, such as 15 hours or less, such as 10 hours or less, such as five hours or less, such as one hour or less, such as 30 minutes or less, such as 10 minutes or less, such as 5 minutes or less, such as one minute or less. In some embodiments, the retrieval device 2200 can be used to retrieve a device 100 that has been implanted within a patient's native valve for more than one month. While the retrieval device is described as retrieving the implanted device 100, it should be understood that the retrieval device 2200 can be used to retrieve any suitable type of device that is implanted within a native valve of a patient.

Figure 39:
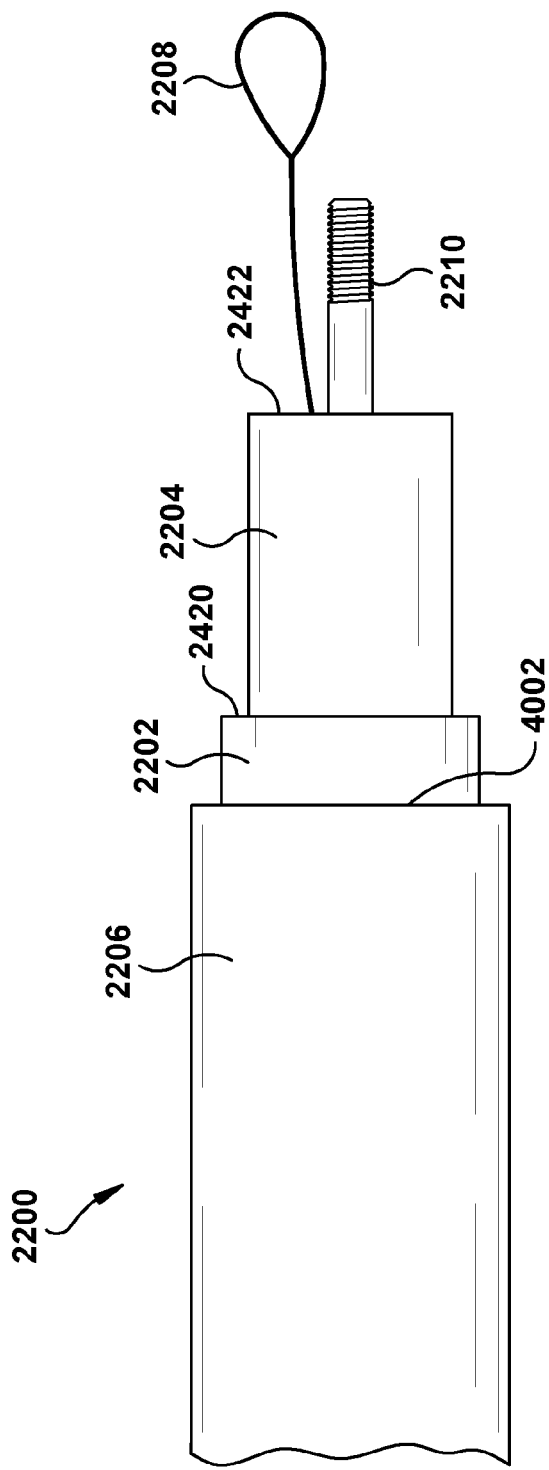
FIG. 39 shows an example embodiment of a retrieval device for retrieving an implanted prosthetic device from a native valve.

Referring to FIG. 39, the example retrieval device 2200 includes a catheter 2202 that is configured to position the retrieval device 2200 to engage the implanted device 100, a retrieval shaft 2204, and one or more components (2206, 2208, 2210) for engaging and removing the implanted device 100 from a patient's native valve. In the illustrated embodiment, the one or more components include a capturing member 2206, securing member 2208, and an actuation member 2210. In some embodiments, the capturing member 2206 can be a hollow shaft that extends around the catheter 2202. The retrieval shaft 2204 can also have one or more lumens or bores for guiding the other components (2208, 2210). All of the other components (2208, 2210) can be disposed in a single lumen, each of the other components can be disposed in a lumen by itself, or any other suitable number of lumens can be used to guide the other components.

The securing member 2208 can take any suitable form that is capable of securing the retrieval device 2200 to the implanted device 100, such as, for example, any form described in the present application. In the illustrated embodiment, the securing member 2208 is a snare having a wire loop, in which the wire loop is configured to extend around a collar 115 of the implanted device 100. The securing member 2208 can be made of, for example, metal, such as steel, nitinol, etc.

The actuation member or actuation element 2210 can take any suitable form that is capable of engaging the implanted device 100 to remove the implanted device from the native valve of the patient, such as, for example, any form described in the present application. In the illustrated embodiment, the actuation member or actuation element 2210 is an actuation wire that is extended from the distal end 2422 of the retrieval shaft 2204 and configured to engage the cap 114 of the implanted device 100 to move the implanted device from a closed position to an open position. The actuation member/element 2210 can be made of, for example, metal, such as steel, nitinol, etc.

Figure 40:
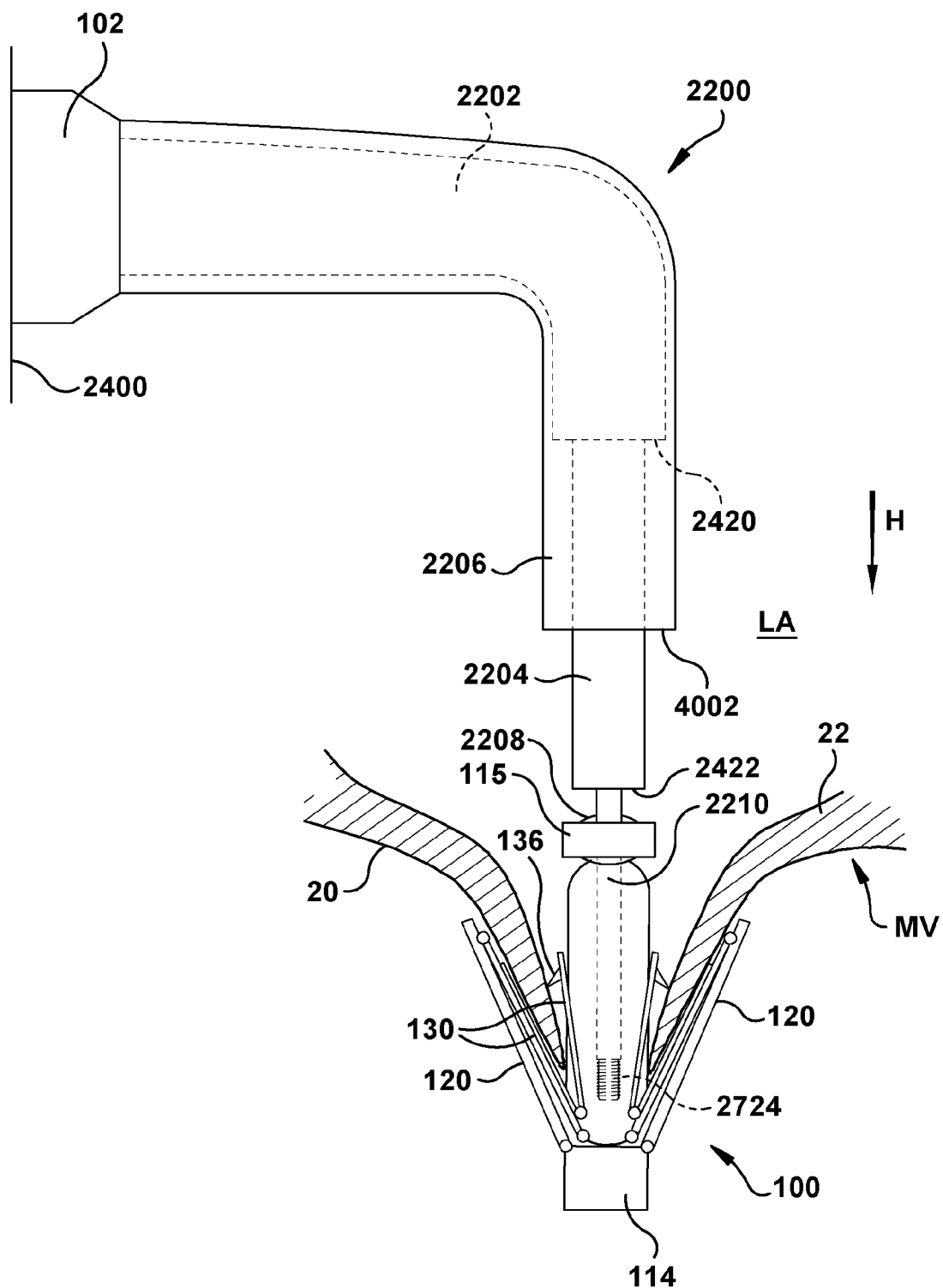
FIGS. 40-42 show the example retrieval device of FIG. 39 being positioned to engage and engaging the implanted prosthetic device of FIG. 22 to remove the implanted prosthetic device from a native valve.
Figure 41:
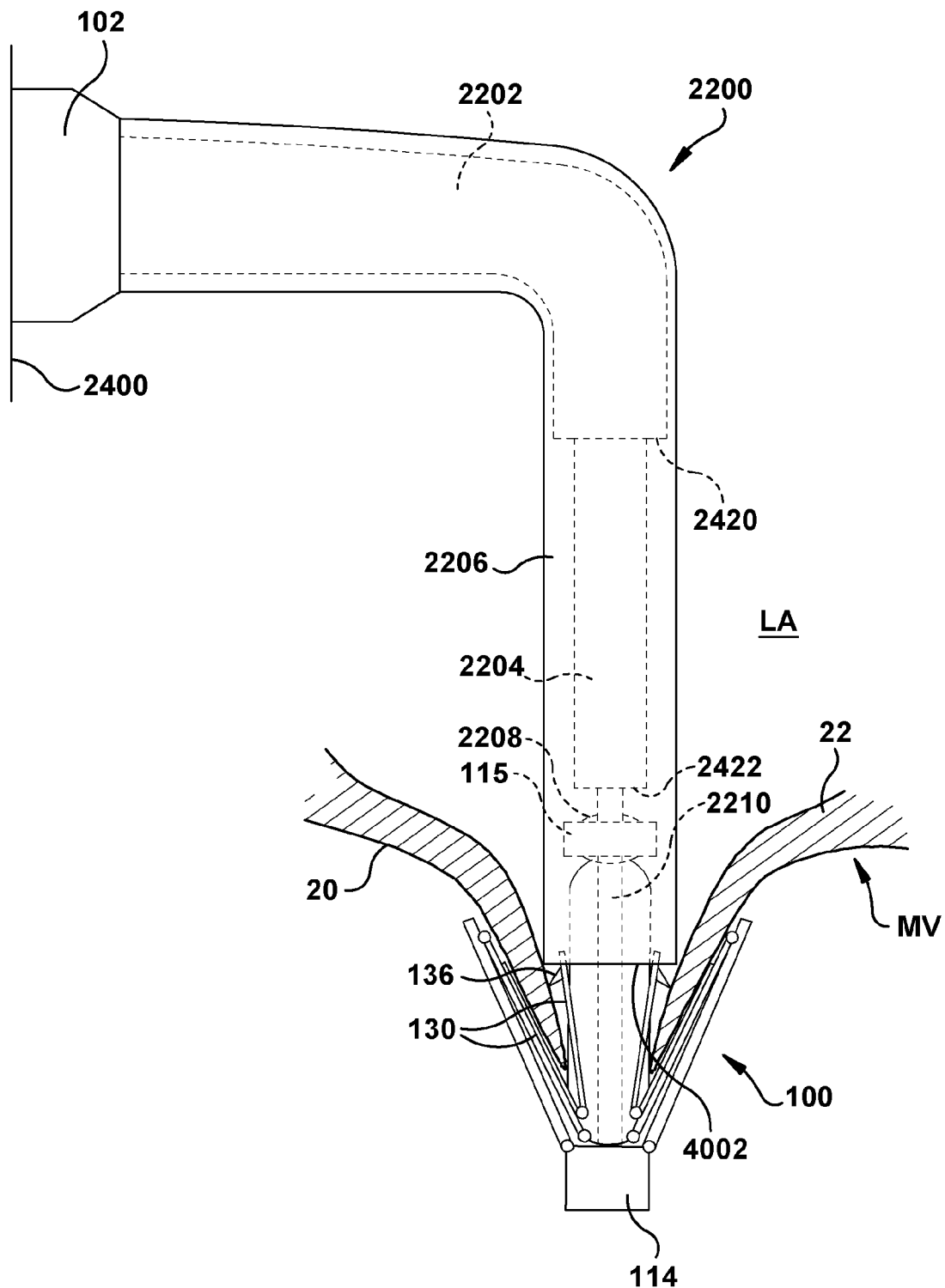
Figure 42:
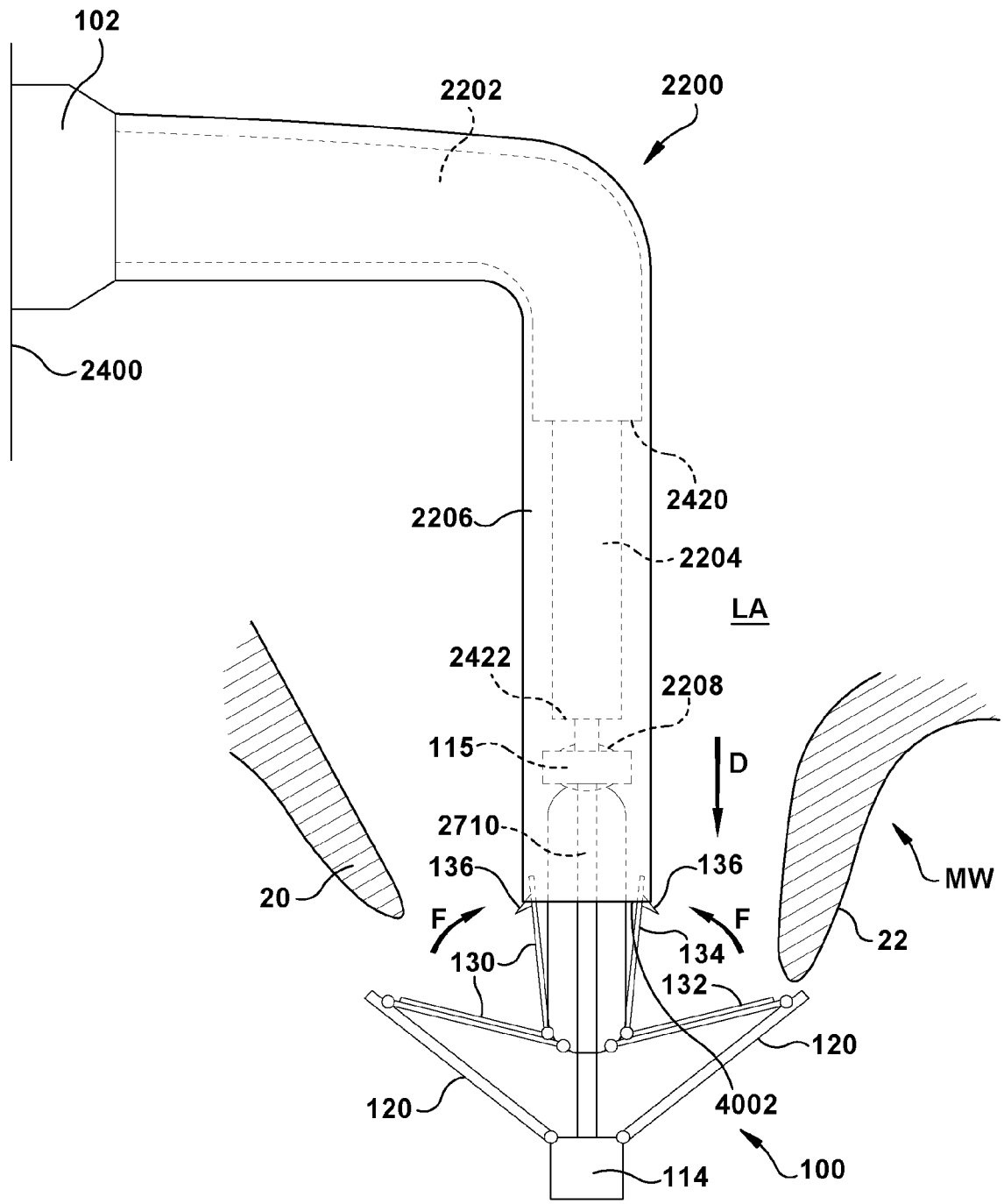

Referring now to FIGS. 40-42, the retrieval device 2200 is shown being positioned to engage and engaging an implanted device 100 on the native valve, or native mitral valve MV in this example, to remove the implanted device from the native valve. The retrieval device 2200 is shown extending through the septum 2400 of a heart such that the retrieval device 2200 is positioned in the left atrium LA of the heart. In certain embodiments, a delivery sheath 102 is used to deliver the retrieval device 2200 to the heart of a patient. The delivery sheath 102 can deliver the retrieval device to the patient's heart by any suitable means, such as, for example, by any means described in the present application regarding the delivering and implanting of the implantable device 100. After the sheath 102 is positioned in the left atrium LA, the catheter 2202 can be configured to be steerable such that the distal end 2420 of the catheter 2202 can be positioned above the implanted device 100. After the distal end 2420 of the catheter 2202 is positioned above the implanted device 100, the retrieval shaft 2204 can be extended out of a distal end 2420 of the catheter 2202 such that the one or more components (2206, 2208, 2210) are positioned to engage and retrieve the implanted device 100. In certain embodiments, the distal end 2422 of the retrieval shaft 2204 is positioned near the collar 115 of the device 100.

Referring to FIG. 40, once the distal end 2422 of the retrieval shaft 2204 is positioned near or in contact with the collar 115 of the device 100, the securing member 2208 is extended from the retrieval shaft 2204 to engage the collar 115 to secure the retrieval device 2200 to the implanted device 100. In the illustrated embodiment, the securing member 2208 is a snare having a wire loop, in which the wire loop is configured to extend around the collar 115.

Referring to FIGS. 40 and 41, after the securing member 2208 secures the retrieval device 2200 to the implanted device 100, the actuation member or actuation element 2210 is extended from the distal end 2422 of the retrieval shaft 2204 to engage the cap 114 of the implanted device 100. In particular, the actuation member 2210 has a distal end 2724 that is configured to engage the cap 114. In certain embodiments, the distal end 2724 of the actuation member 2210 is configured to be attached to the cap 114 (as shown in FIG. 41). For example, the actuation member 2210 and the cap 114 can be connected by a threaded connection, a snap-fit connection, a frictional connection, a magnetic connection, a twist and lock type connection, or any other suitable connection. In the illustrated embodiment, the actuation member 2210 is threaded such that rotation of the actuation member connects the actuation member to the cap 114 of the implanted device 100. The actuation member 2210 can, however, take a wide variety of different forms, such as, for example, any form described for actuation element 112 in FIGS. 8-14 or any other actuation member or actuation element described anywhere herein.

Still referring to FIGS. 40-41, the capturing member 2206 is extended over the catheter 2202 and the retrieval shaft 2204 in the direction H (as shown in FIG. 40) until a distal end 4002 of the capturing member 2206 engages gripping clasps 130 (as shown in FIG. 41). In the illustrated embodiment, the capturing member 2206 is a hollow shaft that is configured to extend over a portion of the gripping clasps 130.

Referring to FIG. 42, after the capturing member 2206 engages the gripping clasps 130, the retrieval device 2200 is used to move the device 100 to the partially opened position (as described above with reference to FIGS. 8-14) by moving the actuation member 2210 in the direction D while holding the position of the collar 115 with the securing member 2208 and/or the retrieval shaft 2204. The actuation member 2210 moves the cap 114 in the direction D. As the cap 114 moves in the direction D, and the device 100 moves to the partially opened position, the engagement between the capturing member 2206 and the gripping clasps 130 causes the gripping clasps to be removed from the leaflets 20, 22 of the native valve. That is, as the actuation member 2210 causes the fixed arms 132 of the gripping clasps 130 and the paddles 120 to move to the partially opened position (as shown in FIG. 42), the capturing member 2206 provides a force on the movable arms 134 of the gripping clasps 130 in the direction F that causes the barbs 136 of the gripping clasps 130 to be removed from the native valve.

After the barbs 136 of the gripping clasps 130 are released from the leaflets 20, 22, the device 100 is no longer engaged with the native valve, and the device 100 can moved to the elongated and fully open position (as described above herein with reference to FIGS. 8-14). In some embodiments, the device 100 is moved to the fully open position by further movement of the actuation member 2210 in the direction D (as shown in FIG. 42), which causes the cap 114 to move in the direction D. This movement of the cap 114 in the direction D until the cap 114 reaches a fully open state causes the device to be in the fully open position.

After the device 100 is in the fully open position the retrieval shaft 2204 and the device 100 are retracted into the sheath. Then, the sheath 102 containing the retrieval device 2200, and the device 100, are removed from the patient's heart.

Referring now to FIGS. 50-57, an example embodiment of a retrieval device 2200 is shown that is configured to remove and retrieve a device that was previously implanted within a patient's native valve (e.g., implanted device 100 shown in FIGS. 8-14 and 21). The previously implanted device can be retrieved after it has been implanted for various periods of time. In some embodiments, the retrieval device 2200 can be used to retrieve a device 100 that has been implanted within a patient's native valve for one month or less, such as 30 days or less, such as 25 days or less, such as 20 days or less, such as 15 days or less, such as 10 days or less, such as seven days or less, such as six days or less, such as five days or less, such as four days or less, such as three days or less, such as two days or less, such as one day or less, such as 20 hours or less, such as 15 hours or less, such as 10 hours or less, such as five hours or less, such as one hour or less, such as 30 minutes or less, such as 10 minutes or less, such as 5 minutes or less, such as one minute or less. In some embodiments, the retrieval device 2200 can be used to retrieve a device 100 that has been implanted within a patient's native valve for more than one month. While the retrieval device is described as retrieving the implanted device 100, it should be understood that the retrieval device 2200 can be used to retrieve any suitable type of device that is implanted within a native valve of a patient.

Figure 50:
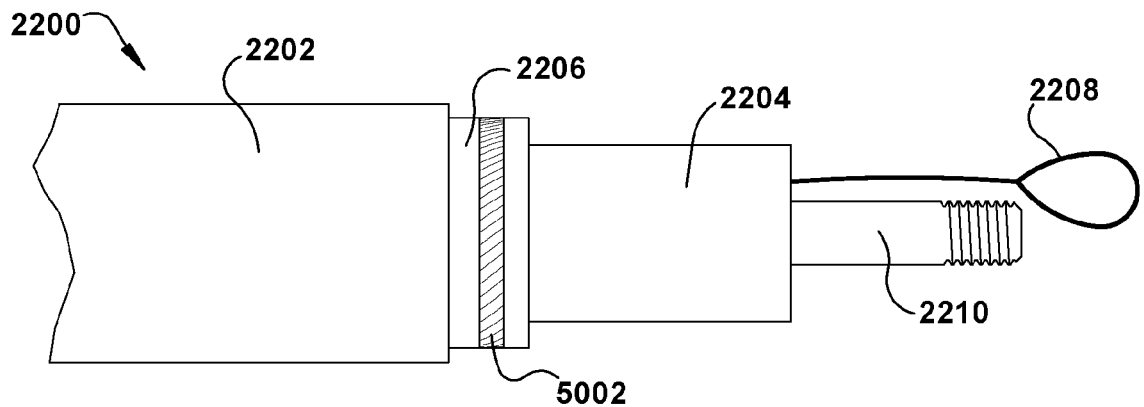
FIG. 50 shows an example embodiment of another retrieval device for retrieving an implanted prosthetic device from a native valve.

Referring to FIG. 50, the example retrieval device 2200 includes a catheter 2202 that is configured to position the retrieval device 2200 to engage the implanted device 100, a retrieval shaft 2204, and one or more components (2206, 2208, 2210) for engaging and removing the implanted device 100 from a patient's native valve. In the illustrated embodiment, the one or more components include a capturing member 2206, securing member 2208, and an actuation member 2210. In certain embodiments, the retrieval shaft 2204 can have one or more lumens or bores for guiding at least some of the one or more components (2206, 2208, 2210). For example, at least some of the one or more components can be disposed in a single lumen, each of the components can be disposed in a lumen by itself, or any other suitable number of lumens can be used to guide the one or more components.

In the illustrated embodiment, the capturing member 2206 can be a hollow shaft that extends around the retrieval shaft 2204, in which the hollow shaft includes one or more capturing elements 5002. The capturing element 5002 can take any suitable form that is capable of attaching to the gripping clasps 130 of an implanted device 100 to maintain the gripping clasps 130 in a desired position such that movement of the implanted device from a closed position to an open position causes the gripping clasps to be removed from valve tissue of a patient.

Figure 51:
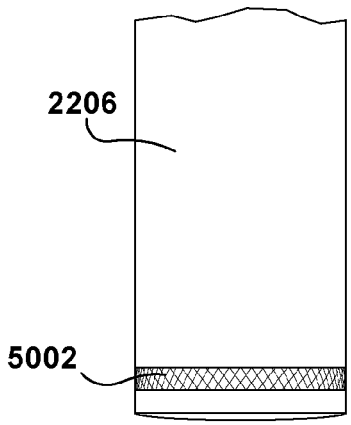
FIGS. 51-54 show various embodiments of capturing member for the example retrieval device of FIG. 50.
Figure 52:
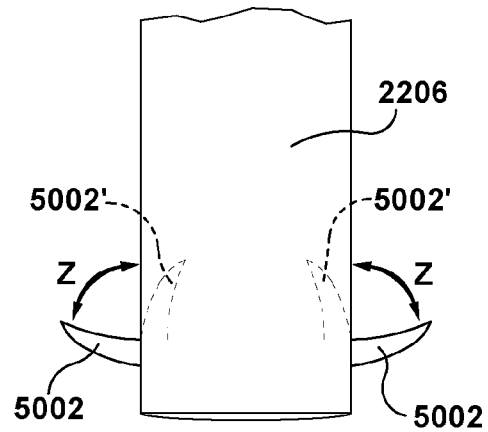
Figure 53:
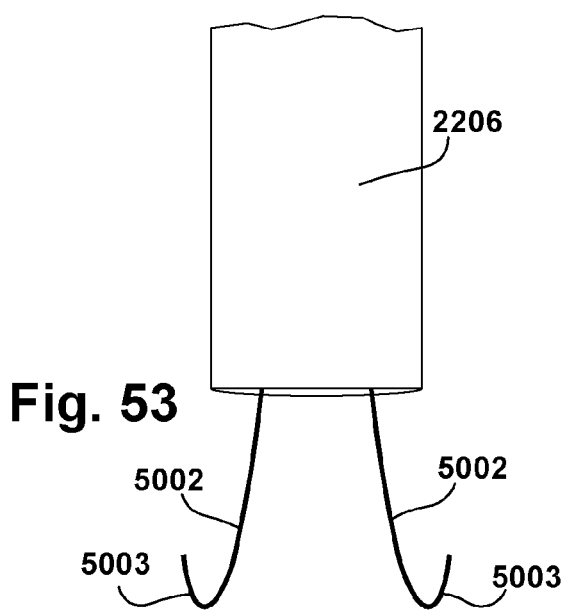
Figure 54:
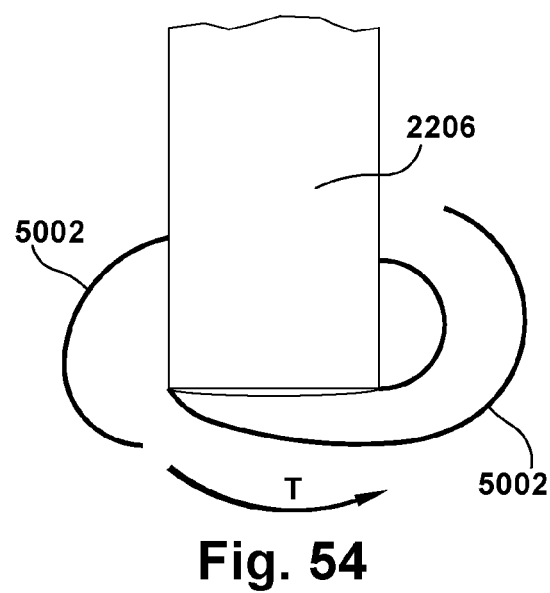

Various example embodiments of capturing elements 5002 are shown in FIGS. 51-54. Referring to FIG. 51, the capturing element 5002 is a hook and loop connector that is configured to connect to a hook and loop connector of the gripping clasps 130. Referring to FIG. 52, the capturing elements 5002 are a pair of barbs that are movable in the direction Z between a normal position (as shown by reference character 5002) and a collapsible position (as shown by reference character 5002'). Referring to FIG. 53, the capturing elements 5002 are a pair of wires with hooks 5003, in which the hooks 5003 are configured to engage the gripping clasps 130 to attach the capturing member 2206 to the gripping clasps. The wire 5003 can be made of, for example, metal, such as, steel, nitinol, etc. Referring to FIG. 54, the capturing elements 5002 are a pair of curved hooks that are movable between an unlocked position and a locked position. That is, when the capturing member 2206 is positioned to engage an implanted device 100, the curved hooks of the capturing elements 5002 are in an unlocked position with the gripping clasps 130, and movement of the curved hooks in the direction T causes the curved hooks to engage the gripping clasps such that the capturing elements 5002 are secured to the gripping clasps. While FIGS. 51-54 show various embodiments of capturing elements 5002 of the capturing member 2206, it should be understood that various other capturing elements can be used that are capable of being attached to the gripping clasps 130 of an implanted device 100 to maintain the gripping clasps in a desired position.

The securing member 2208 can take any suitable form that is capable of securing the retrieval device 2200 to the implanted device 100, such as, for example, any form described in the present application. In the illustrated embodiment, the securing member 2208 is a snare having a wire loop, in which the wire loop is configured to extend around a collar 115 of the implanted device 100. The securing member 2208 can be made of, for example, metal, such as steel, nitinol, etc.

The actuation member/element 2210 can take any suitable form that is capable of engaging the implanted device 100 to remove the implanted device from the native valve of the patient, such as, for example, any form described in the present application. In the illustrated embodiment, the actuation member/element 2210 is an actuation wire that is extended from the distal end 2422 of the retrieval shaft 2204 and configured to engage the cap 114 of the implanted device 100 to move the implanted device from a closed position to an open position. The actuation member 2210 can be made of, for example, metal, such as steel, nitinol, etc.

Figure 55:
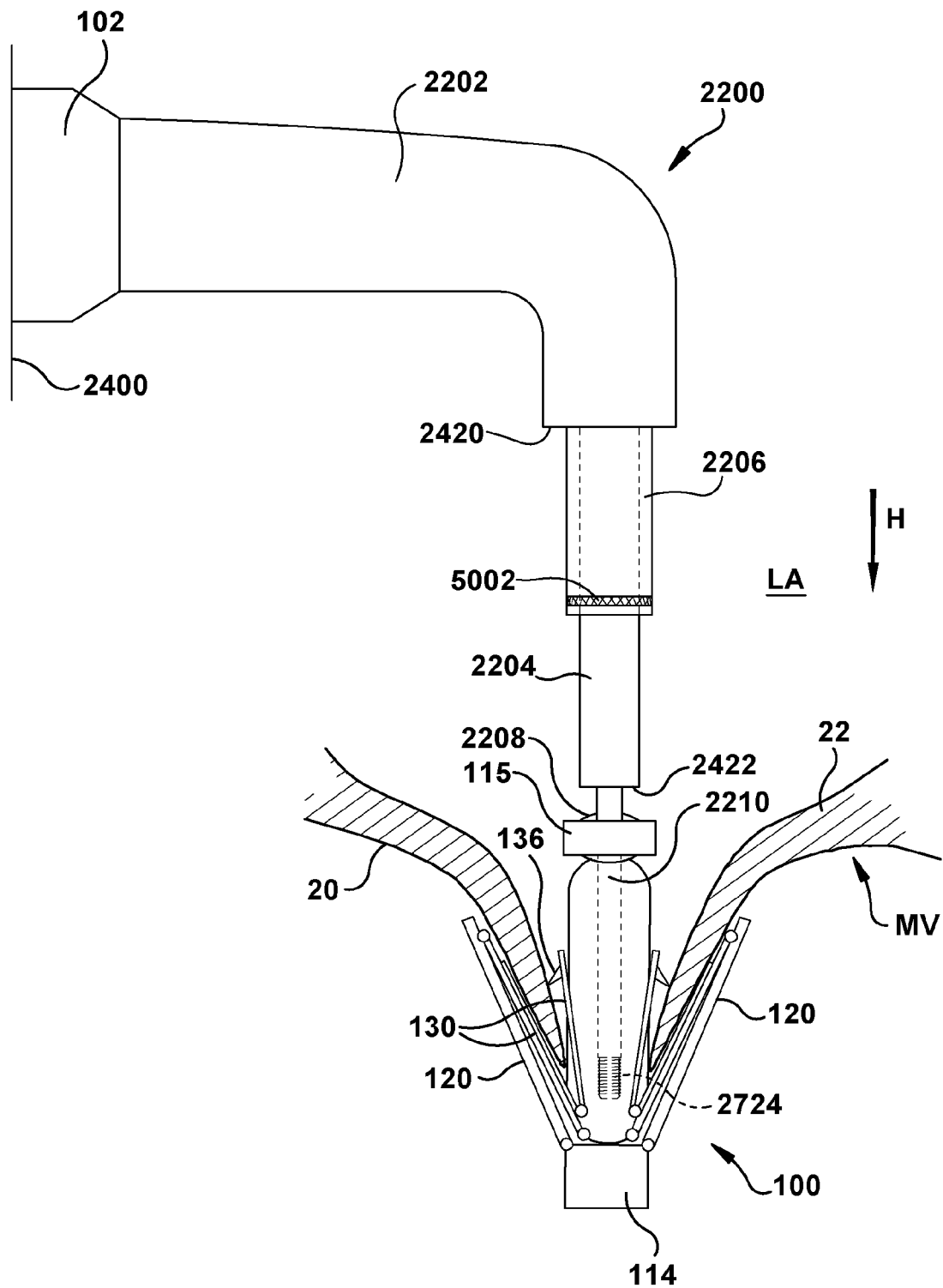
FIGS. 55-57 show the example retrieval device of FIG. 50 being positioned to engage and engaging the implanted prosthetic device of FIG. 22 to remove the implanted prosthetic device from a native valve.
Figure 56:
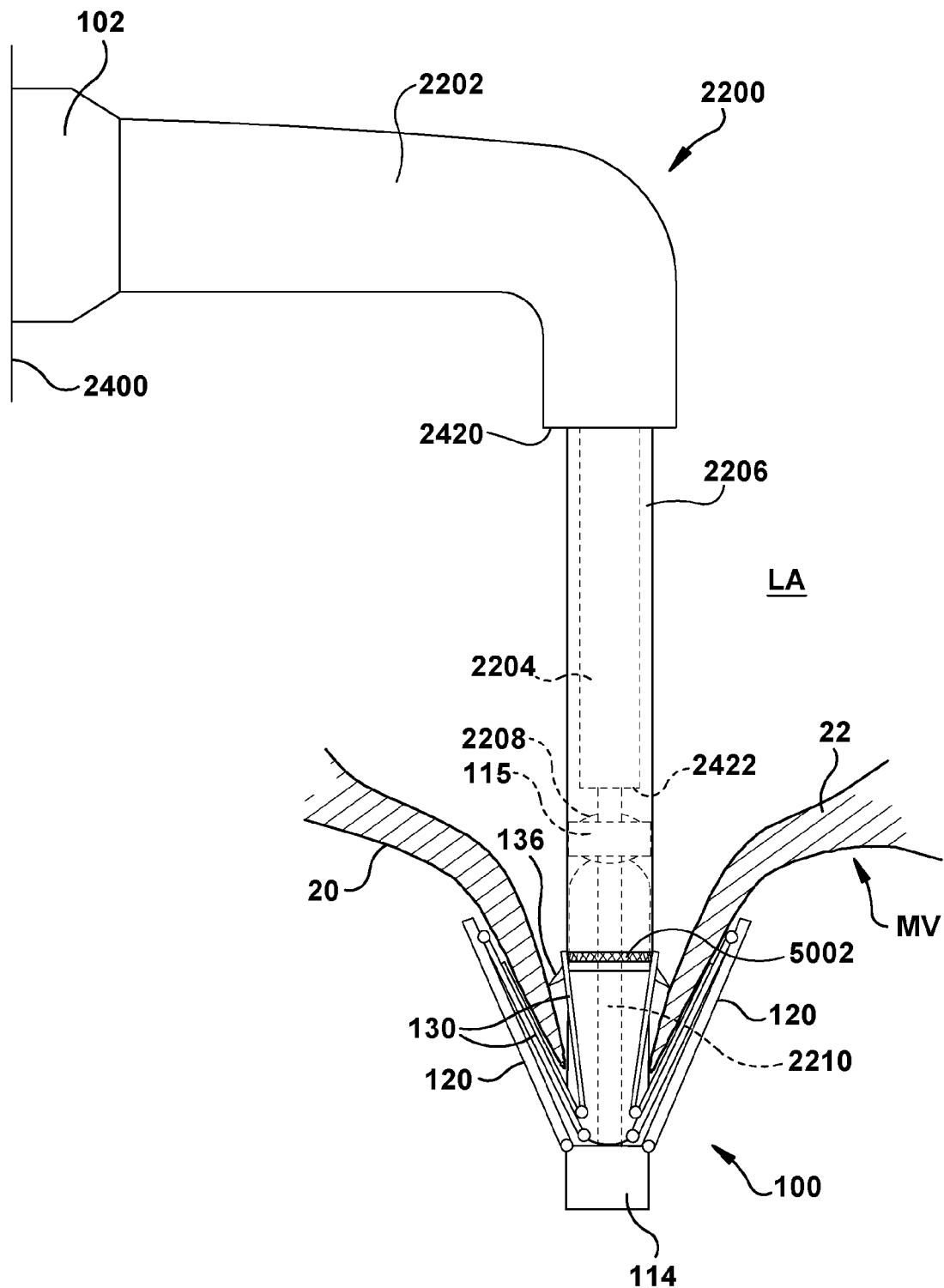
Figure 57:
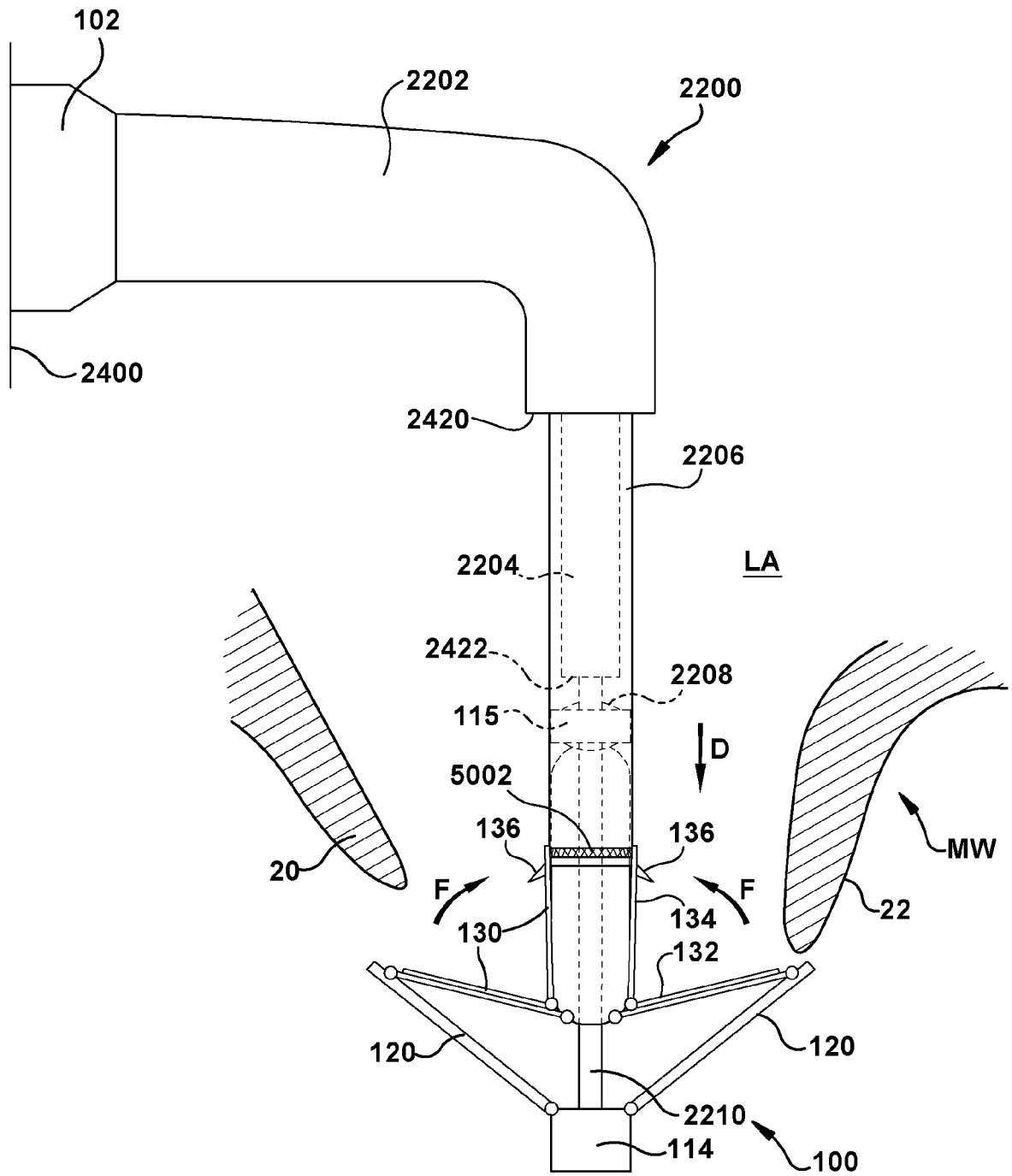

Referring now to FIGS. 55-57, the retrieval device 2200 is shown engaging an implanted device 100 on a native valve, or on the native mitral valve MV in this example, to remove the implanted device from the native valve. The retrieval device 2200 is shown extending through the septum 2400 of a heart such that the retrieval device 2200 is positioned in the left atrium LA of the heart. In certain embodiments, a delivery sheath 102 is used to deliver the retrieval device 2200 to the heart of a patient. The delivery sheath 102 can deliver the retrieval device to the patient's heart by any suitable means, such as, for example, by any means described in the present application regarding the delivering and implanting of the implantable device 100. After the sheath 102 is positioned in the left atrium LA, the catheter 2202 can be configured to be steerable such that the distal end 2420 of the catheter 2202 can be positioned above the implanted device 100. After the distal end 2420 of the catheter 2202 is positioned above the implanted device 100, the retrieval shaft 2204 can be extended out of a distal end 2420 of the catheter 2202 such that the one or more components (2208, 2210) are positioned to engage and retrieve the implanted device 100, and the capturing member 2206 can be extended out of the distal end 2420 of the catheter 2202 and positioned to engage the gripping clasps 130 of the implanted device 100. In certain embodiments, the distal end 2422 of the retrieval shaft 2204 is positioned near the collar 115 of the device 100.

Referring to FIG. 55, once the distal end 2422 of the retrieval shaft 2204 is positioned near or in contact with the collar 115 of the device 100, the securing member 2208 is extended from the retrieval shaft 2204 to engage the collar 115 to secure the retrieval device 2200 to the implanted device 100. In the illustrated embodiment, the securing member 2208 is a snare having a wire loop, in which the wire loop is configured to extend around the collar 115.

Referring to FIGS. 55 and 56, after the securing member 2208 secures the retrieval device 2200 to the implanted device 100, the actuation member or actuation element 2210 is extended from the distal end 2422 of the retrieval shaft 2204 to engage the cap 114 of the implanted device 100. In particular, the actuation member 2210 has a distal end 2724 that is configured to engage the cap 114. In certain embodiments, the distal end 2724 of the actuation member 2210 is configured to be attached to the cap 114 (as shown in FIG. 56). For example, the actuation member 2210 and the cap 114 can be connected by a threaded connection, a snap-fit connection, a frictional connection, a magnetic connection, a twist and lock type connection, or any other suitable connection. In the illustrated embodiment, the actuation member 2210 is threaded such that rotation of the actuation member connects the actuation member to the cap 114 of the implanted device 100. The actuation member 2210 can, however, take a wide variety of different forms, such as, for example, any form described for actuation element 112 in FIGS. 8-14.

Still referring to FIGS. 55-56, the capturing member 2206 is extended over the retrieval shaft 2204 in the direction H (as shown in FIG. 55) until a distal end 5004 of the capturing member 2206 engages gripping clasps 130 (as shown in FIG. 56). In the illustrated embodiment, the capturing member 2206 is a hollow shaft that includes a capturing element 5002 that is configured to engage the gripping clasps 130 such that the capturing member 2206 is attached to the gripping clasps 130. The capturing element 5002 can take any form described in FIGS. 51-54 or elsewhere herein, or any other suitable form for attaching the capturing member 2206 to the gripping clasps 130.

Referring to FIG. 57, after the capturing element 5002 of the capturing member 2206 engages the gripping clasps 130, the retrieval device 2200 is used to move the device 100 to the partially opened position (as described above with reference to FIGS. 8-14) by moving the actuation member 2210 in the direction D while holding the position of the collar 115 with the securing member 2208 and/or the retrieval shaft 2204. The actuation member 2210 moves the cap 114 in the direction D. As the cap 114 moves in the direction D, and the device 100 moves to the partially opened position, the engagement between the capturing element 5002 and the gripping clasps 130 causes the gripping clasps to be removed from the leaflets 20, 22 of the native valve. That is, as the actuation member 2210 causes the fixed arms 132 of the gripping clasps 130 and the paddles 120 to move to the partially opened position (as shown in FIG. 57), the capturing element 5002 provides a force on the movable arms 134 of the gripping clasps 130 in the direction F that causes the barbs 136 of the gripping clasps 130 to be removed from the native valve.

After the barbs 136 of the gripping clasps 130 are released from the leaflets 20, 22, the device 100 is no longer engaged with the native valve, and the device 100 can moved to the elongated and fully open position (as described above herein with reference to FIGS. 8-14). In certain embodiments, the device 100 is moved to the fully open position by further movement of the actuation member 2210 in the direction D (as shown in FIG. 57), which causes the cap 114 to move in the direction D. This movement of the cap 114 in the direction D until the cap 114 reaches a fully open state causes the device to be in the fully open position.

After the device 100 is in the fully open position the retrieval shaft 2204 and the device 100 are retracted into the sheath. Then, the sheath 102 containing the retrieval device 2200, and the device 100, are removed from the patient's heart.

Referring now to FIGS. 43-49, an example embodiment of a retrieval device 2200 is shown that is configured to remove and retrieve a device that was previously implanted within a patient's native valve (e.g., implanted device 100 shown in FIGS. 8-14 and 21). The previously implanted device can be retrieved after it has been implanted for various periods of time. In some embodiments, the retrieval device 2200 can be used to retrieve a device 100 that has been implanted within a patient's native valve for one month or less, such as 30 days or less, such as 25 days or less, such as 20 days or less, such as 15 days or less, such as 10 days or less, such as seven days or less, such as six days or less, such as five days or less, such as four days or less, such as three days or less, such as two days or less, such as one day or less, such as 20 hours or less, such as 15 hours or less, such as 10 hours or less, such as five hours or less, such as one hour or less, such as 30 minutes or less, such as 10 minutes or less, such as 5 minutes or less, such as one minute or less. In some embodiments, the retrieval device 2200 can be used to retrieve a device 100 that has been implanted within a patient's native valve for more than one month. While the retrieval device is described as retrieving the implanted device 100, it should be understood that the retrieval device 2200 can be used to retrieve any suitable type of device that is implanted within a native valve of a patient.

Figure 43:
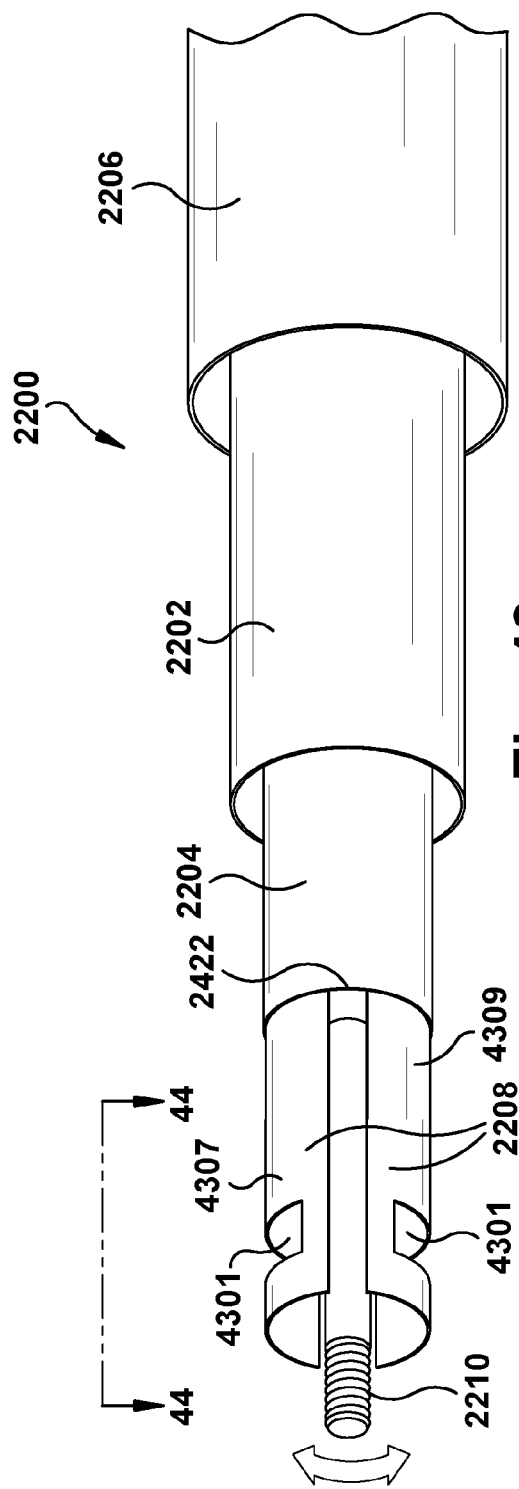
FIG. 43 shows an example embodiment of another retrieval device for retrieving an implanted prosthetic device from a native valve.
Figure 44:
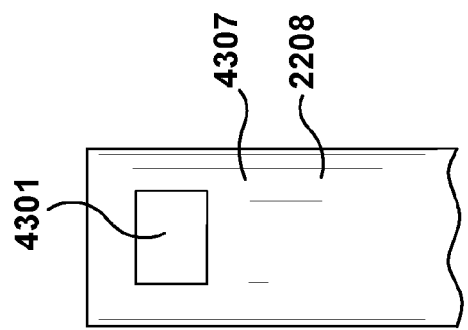
FIG. 44 shows a partial view of the example retrieval device of FIG. 43 taken along the line 44-44 of FIG. 43.
Figure 45:
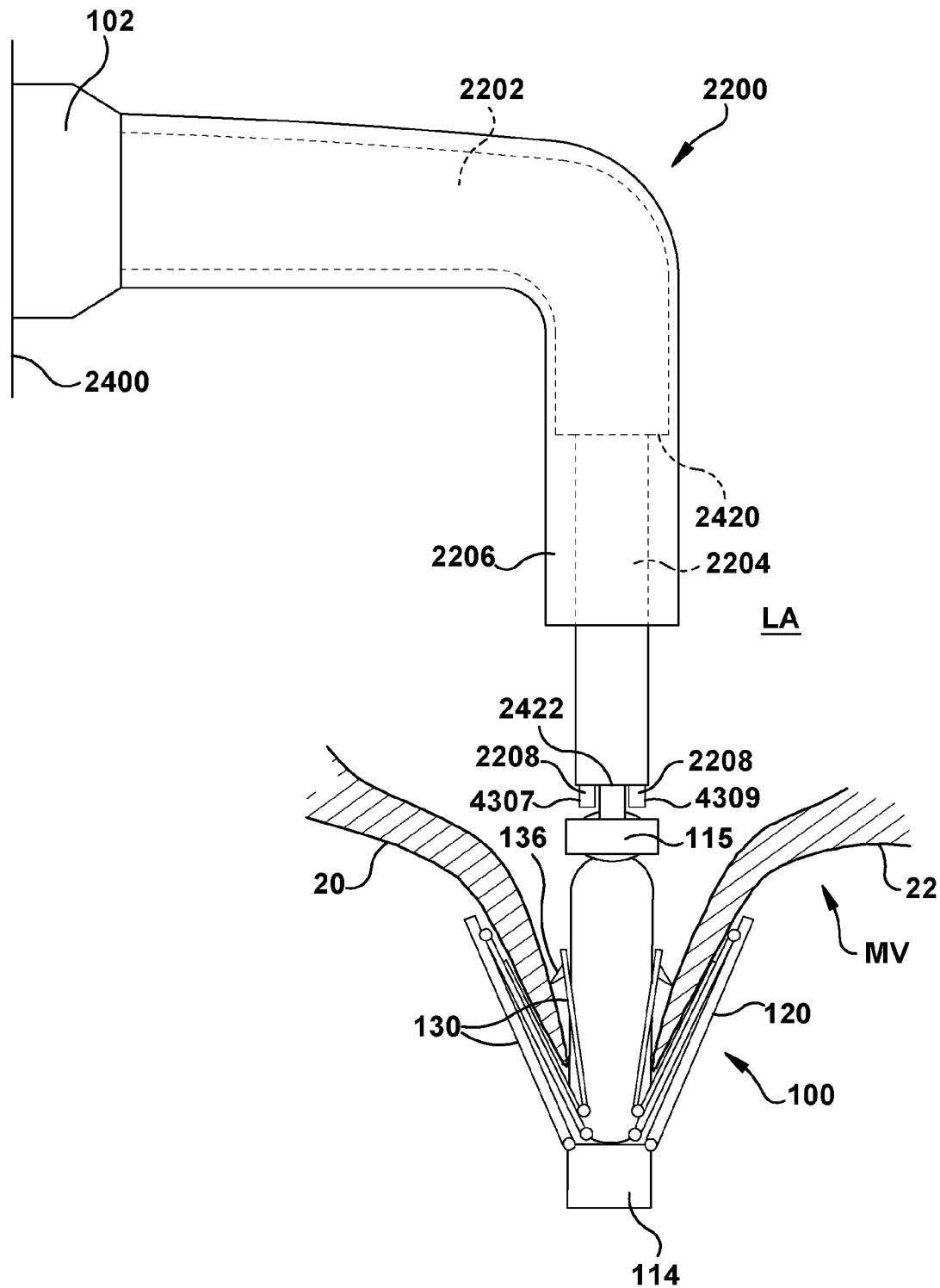
FIGS. 45-49 show the example retrieval device of FIG. 43 being positioned to engage and engaging the implanted prosthetic device of FIG. 22 to remove the implanted prosthetic device from a native valve.

Referring to FIGS. 43-44, the example retrieval device 2200 includes a catheter 2202 that is configured to position the retrieval device 2200 to engage the implanted device 100, a retrieval shaft 2204, and one or more components (2206, 2208, 2210) for engaging and removing the implanted device 100 from a patient's native valve. In the illustrated embodiment, the one or more components include a capturing member 2206, a securing member 2208, and an actuation member/element 2210. In some embodiments, the capturing member 2206 can be a hollow shaft that extends around the catheter 2202. In these embodiments, the capturing member 2206 can engage the device 100 as described herein with reference to FIGS. 40-42. In other embodiments, one or more components can include one or more capturing members that take any other form described in the present application. The retrieval shaft 2204 can also have one or more lumens or bores for guiding the other components (2208, 2210). All of the other components (2208, 2210) can be disposed in a single lumen, each of the other components can be disposed in a lumen by itself, or any other suitable number of lumens can be used to guide the other components.

Still referring to FIGS. 43-44, the securing member 2208 can include a first securing portion 4307 and a second securing portion 4309. Each securing portion 4307, 4309 includes an attachment mechanism 4301 for attaching the securing portions 4307, 4309 to the collar 115 of the implanted device 100. In the illustrated embodiment the attachment mechanism 4301 is an attachment window. In some embodiments, the attachment mechanism 4301 can take any suitable form that is capable of attaching the securing portions 4307, 4309 to the collar 115 of the implanted device 100, such as, for example, an adhesive, a hook and loop fastener, a snap fit connector, a magnet, etc.

The actuation member or actuation element 2210 can take any suitable form that is capable of engaging the implanted device 100 to remove the implanted device from the native valve of the patient, such as, for example, any form described in the present application. In the illustrated embodiment, the actuation member or actuation element 2210 is an actuation wire that is extended from the distal end 2422 of the retrieval shaft 2204 and configured to engage the cap 114 of the implanted device 100 to move the implanted device from a closed position to an open position. The actuation member 2210 can be made of, for example, metal, such as steel, nitinol, etc.

Referring now to FIGS. 45-49, the retrieval device 2200 is shown being positioned to engage and engaging an implanted device 100 on the native valve, or native mitral valve MV in this example, to remove the implanted device from the native valve. The retrieval device 2200 is shown extending through the septum 2400 of a heart such that the retrieval device 2200 is positioned in the left atrium LA of the heart. In certain embodiments, a delivery sheath 102 is used to deliver the retrieval device 2200 to the heart of a patient. The delivery sheath 102 can deliver the retrieval device to the patient's heart by any suitable means, such as, for example, by any means described in the present application regarding the delivering and implanting of the implantable device 100. After the sheath 102 is positioned in the left atrium LA, the catheter 2202 can be configured to be steerable such that the distal end 2420 of the catheter 2202 can be positioned above the implanted device 100. After the distal end 2420 of the catheter 2202 is positioned above the implanted device 100, the retrieval shaft 2204 can be extended out of a distal end 2420 of the catheter 2202 such that the one or more components (2206, 2208, 2210) are positioned to engage and retrieve the implanted device 100. In certain embodiments, the distal end 2422 of the retrieval shaft 2204 is positioned near the collar 115 of the device 100.

Figure 46:
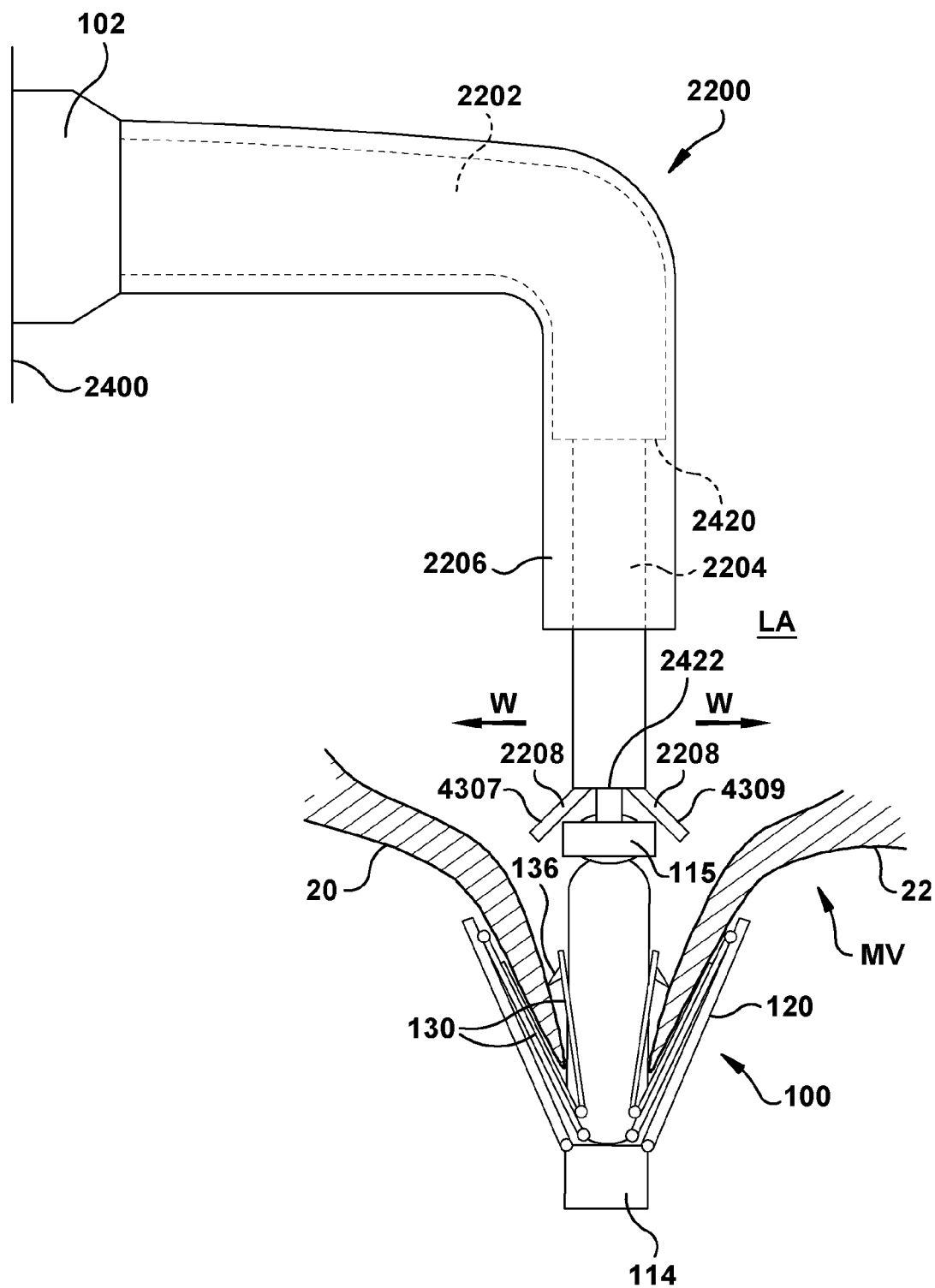
Figure 47:
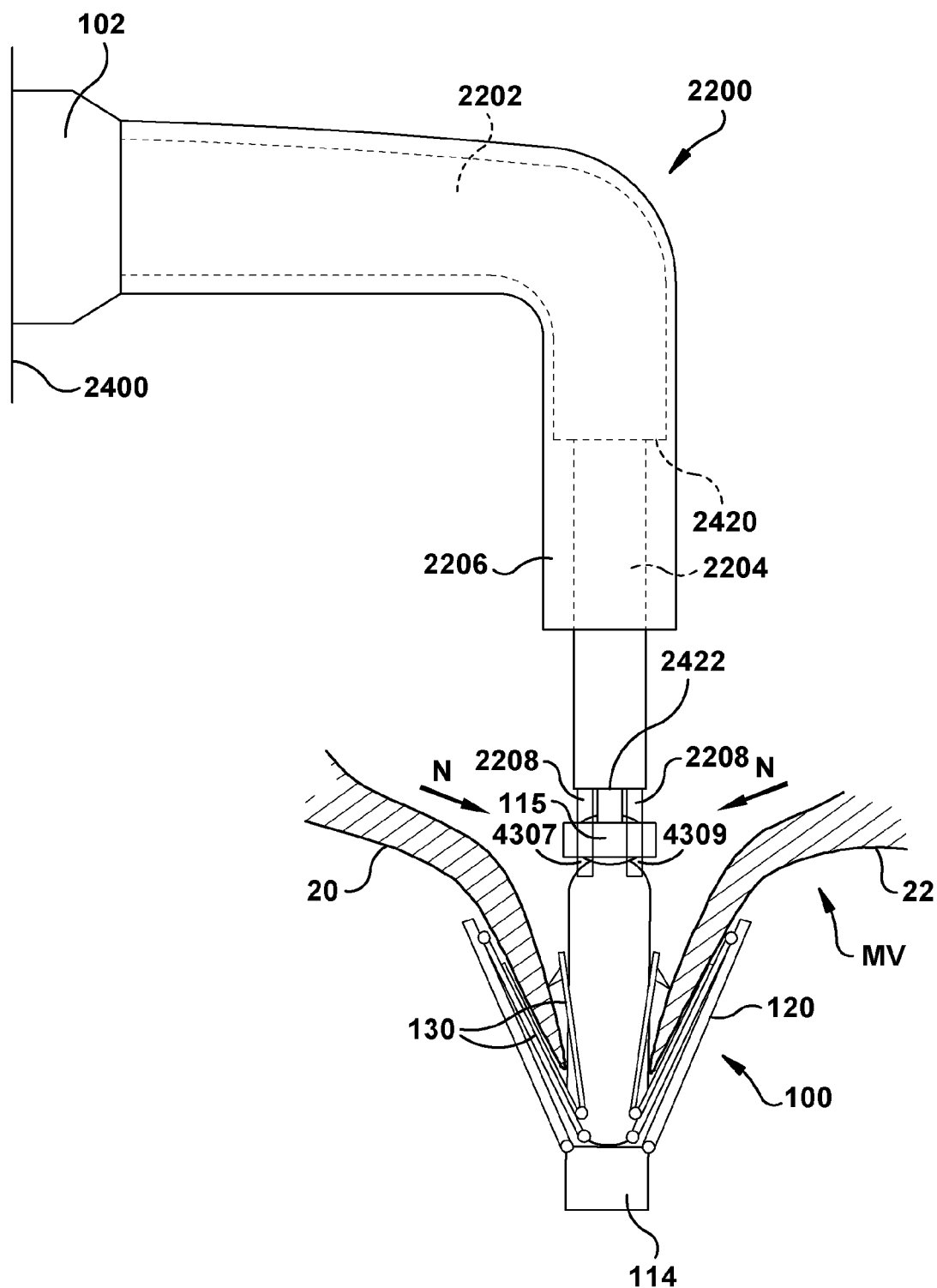

Referring to FIGS. 46-47, once the distal end 2422 of the retrieval shaft 2204 is positioned near or in contact with the collar 115 of the device 100, the securing member 2208 is extended from the retrieval shaft 2204 to engage the collar 115 to secure the retrieval device 2200 to the implanted device 100. Referring to FIG. 46, the securing portions 4307, 4309 are moved in an outward direction W to position the attachment mechanism 4301 (FIGS. 43-44) to attach the securing portions 4307, 4309 to the collar 115. Referring to FIG. 47, after the securing portions 4307, 4309 are moved in the outward direction W (as shown in FIG. 46), the securing portions 4307, 4309 are moved in the inward direction N to secure the securing member 2208 to the collar 115 of the implanted device 100. That is, the attachment mechanism 4301 of the securing portions 4307, 4309 are securing windows, and securing portions are placed such that the collar 115 extends through the securing windows to secure the retrieval device 2200 to the implanted device 100.

Figure 48:
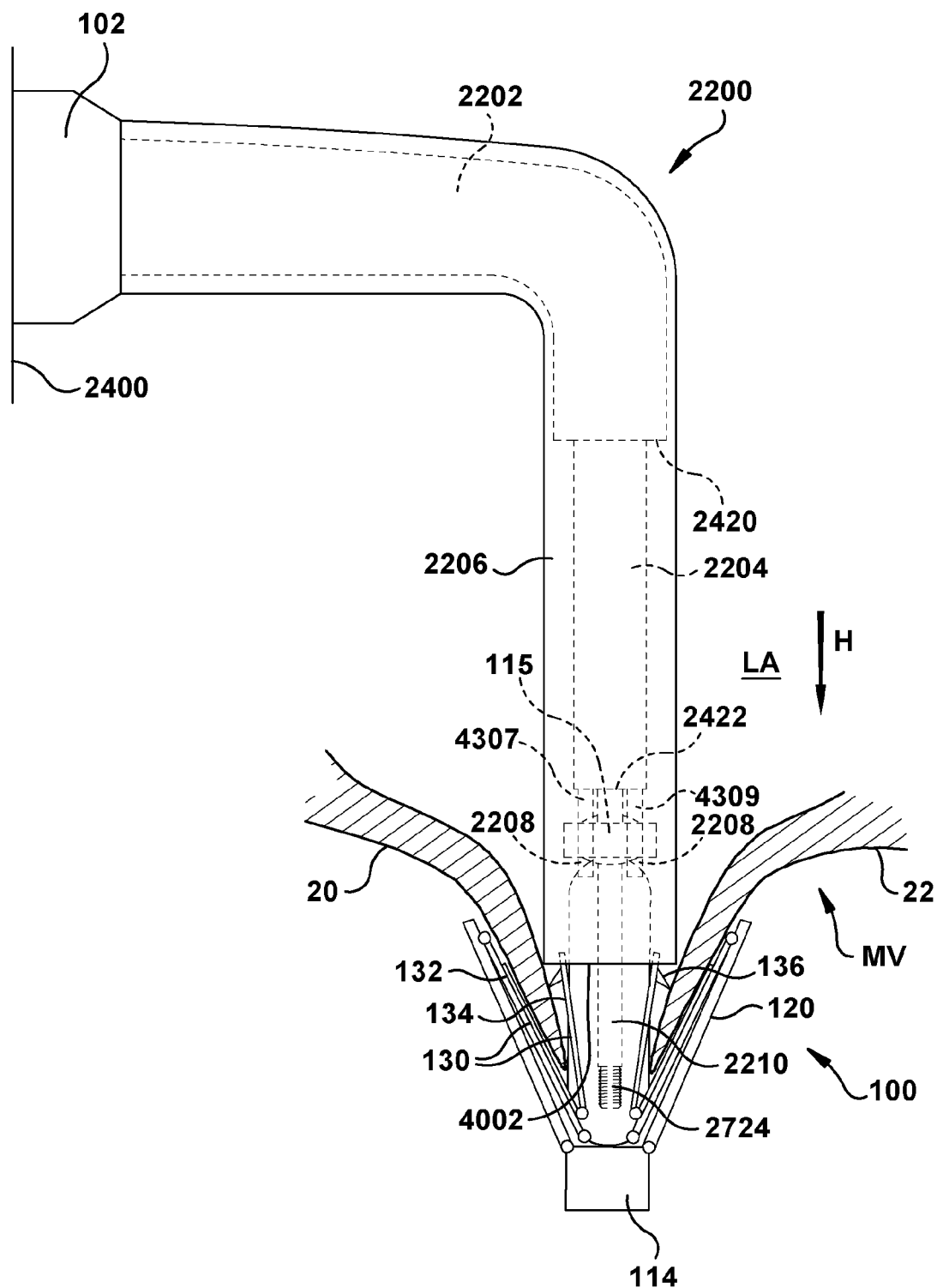
Figure 49:
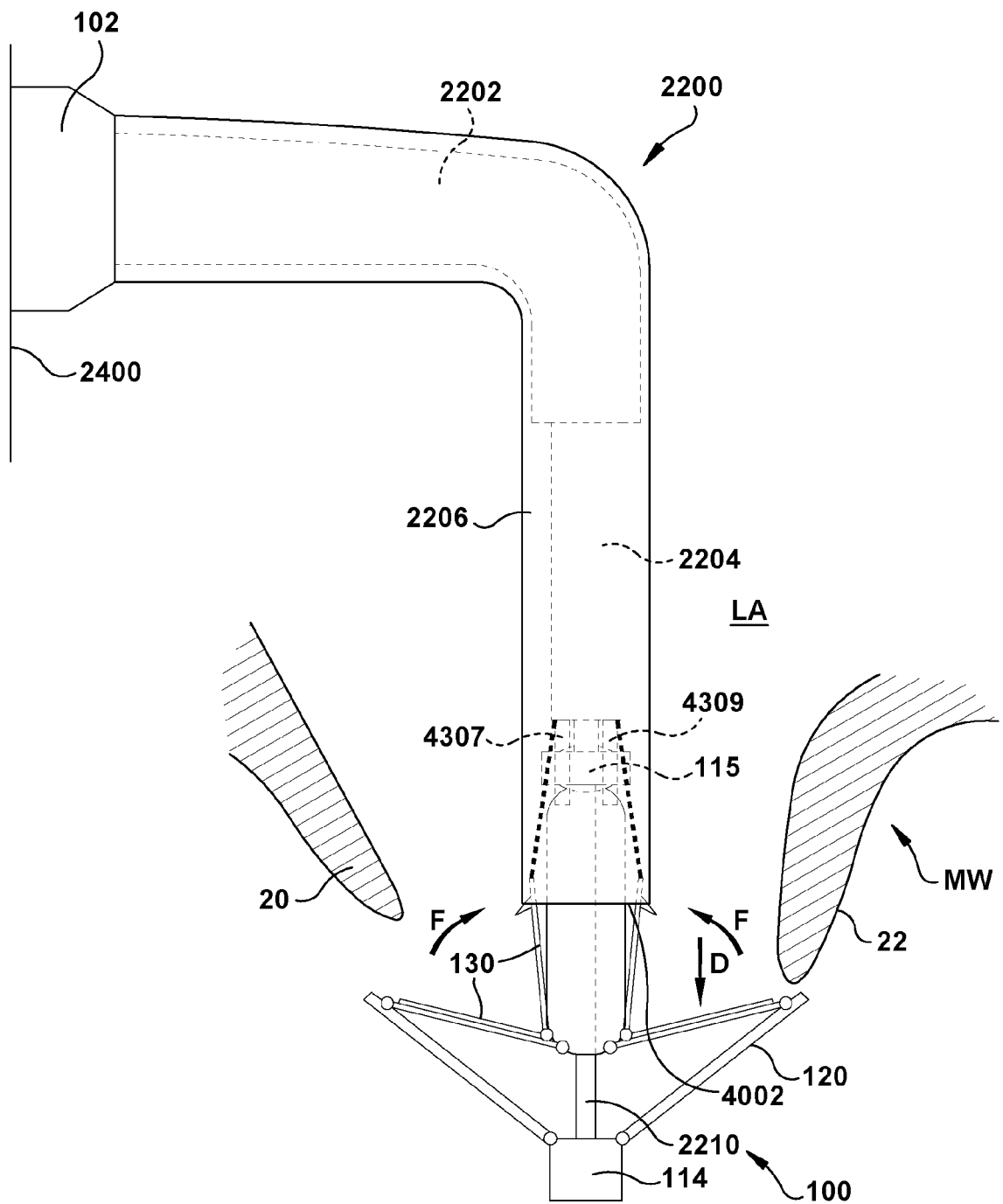

Referring to FIGS. 48-49, after the securing member 2208 secures the retrieval device 2200 to the implanted device 100, the actuation member/element 2210 is extended from the distal end 2422 of the retrieval shaft 2204 to engage the cap 114 of the implanted device 100. In particular, the actuation member 2210 has a distal end 2724 that is configured to engage the cap 114. In certain embodiments, the distal end 2724 of the actuation member 2210 is configured to be attached to the cap 114 (as shown in FIG. 49). For example, the actuation member 2210 and the cap 114 can be connected by a threaded connection, a snap-fit connection, a frictional connection, a magnetic connection, a twist and lock type connection, or any other suitable connection. In the illustrated embodiment, the actuation member 2210 is threaded such that rotation of the actuation member connects the actuation member to the cap 114 of the implanted device 100. The actuation member 2210 can, however, take a wide variety of different forms, such as, for example, any form described for actuation element 112 in FIGS. 8-14.

Still referring to FIGS. 48-49, after the securing member 2208 secures the retrieval device 2200 to the implanted device 100, the capturing member 2206 is extended over the catheter 2202 and the retrieval shaft 2204 in the direction H (as shown in FIG. 48) until a distal end 4002 of the capturing member 2206 engages gripping clasps 130. In the illustrated embodiment, the capturing member 2206 is a hollow shaft that is configured to extend over a portion of the gripping clasps 130 (e.g., the capturing member 2206 described herein with reference to FIGS. 39-42). In other embodiments, the one or more components can include one or more capturing members that take any suitable form that is capable of engaging and removing a gripping clasp 130 from the native valve, such as, for example, any capturing member described in the present application.

Referring to FIG. 49, after the capturing member 2206 engages the gripping clasps 130, the retrieval device 2200 is used to move the device 100 to the partially opened position (as described above with reference to FIGS. 8-14) by moving the actuation member 2210 in the direction D while holding the position of the collar 115 with the securing member 2208 and/or the retrieval shaft 2204. The actuation member 2210 moves the cap 114 in the direction D. In the illustrated embodiment, as the cap 114 moves in the direction D, and the device 100 moves to the partially opened position, the engagement between the capturing member 2206 and the gripping clasps 130 causes the gripping clasps 130 to be removed from the leaflets 20, 22 of the native valve. That is, as the actuation member 2210 causes the fixed arms 132 of the gripping clasps 130 and the paddles 120 to move to the partially opened position, the capturing member 2206 provides a force on the movable arms 134 of the gripping clasps 130 in the direction F that causes the barbs 136 of the gripping clasps 130 to be removed from the native valve.

After the barbs 136 of the gripping clasps 130 are released from the leaflets 20, 22, the device 100 is no longer engaged with the native valve, and the device 100 can moved to the elongated and fully open position (as described above herein with reference to FIGS. 8-14). In some embodiments, the device 100 is moved to the fully open position by further movement of the actuation member 2210 in the direction D (as shown in FIG. 49), which causes the cap 114 to move in the direction D. This movement of the cap 114 in the direction D until the cap 114 reaches a fully open state causes the device to be in the fully open position.

After the device 100 is in the fully open position the retrieval shaft 2204 and the device 100 are retracted into the sheath. Then, the sheath 102 containing the retrieval device 2200, and the device 100, are removed from the patient's heart.

Figure 35:
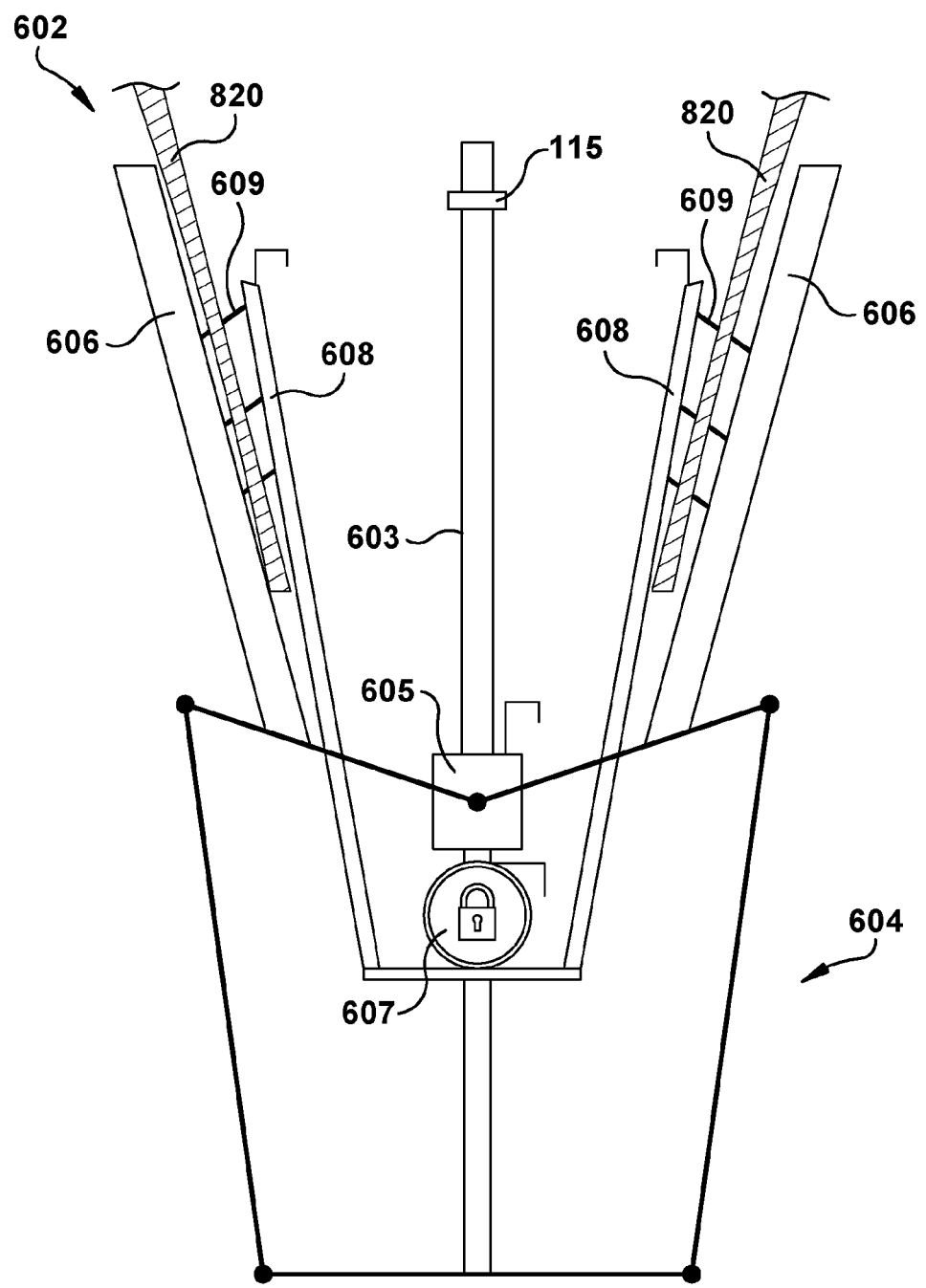
FIG. 35 shows an example embodiment of an implantable prosthetic device implanted within a native valve.

Referring now to FIG. 35, another implantable prosthetic device 602 is shown in a closed position and attached to a patient's valve tissue 820 (e.g., the leaflets of the native mitral valve, leaflets of the native tricuspid valve, etc.). The implantable prosthetic device 602 is described in more detail in U.S. patent application Ser. No. 15/865,962, which is incorporated herein by reference in its entirety. The implantable device 602 includes a base assembly 604, a pair of paddles 606, and a pair of gripping clasps 608. In one example embodiment, the paddles 606 can be integrally formed with the base assembly. For example, the paddles 606 can be formed as extensions of links of the base assembly. In the illustrated example, the base assembly 604 of the valve repair device 602 has a shaft 603, a coupler 605 configured to move along the shaft, and a lock 607 configured to lock the coupler in a stationary position on the shaft. The coupler 605 is mechanically connected to the paddles 606, such that movement of the coupler 605 along the shaft 603 causes the paddles to move between an open position and a closed position. In this way, the coupler 605 serves as means for mechanically coupling the paddles 606 to the shaft 603 and, when moving along the shaft 603, for causing the paddles 606 to move between their open and closed positions.

In certain embodiments, the gripping clasps 608 are connected to the base assembly 604 (e.g., the gripping clasps 608 can be connected to the shaft 603, or any other suitable member of the base assembly), such that the gripping clasps can be moved to adjust the width of the opening between the paddles 606 and the gripping clasps 608. The gripping clasps 608 can include a barbed portion 609 for attaching the gripping members to valve tissue when the implantable prosthetic device 602 is attached to the valve tissue. The gripping clasps 608 forms a means for gripping the valve tissue (in particular tissue of the valve leaflets) with a sticking means or portion such as the barbed portion 609.

When the paddles 606 are in the closed position, the paddles engage the gripping clasps 608, such that, when valve tissue 820 is attached to the barbed portion 609, the paddles act as holding or securing means to hold the valve tissue at the gripping clasps and to secure the valve repair device 602 to the valve tissue. In some embodiments, the gripping clasps 608 are configured to engage the paddles 606 such that the barbed portion 609 engages the valve tissue and the paddles 606 to secure the valve repair device 602 to the valve tissue. For example, in certain situations, it may be advantageous to have the paddles 606 maintain an open position and have the gripping clasps 608 move outward toward the paddles 606 to engage valve tissue and the paddles 606. While the embodiment shown in FIG. 35 illustrates an implantable prosthetic device 602 having a pair of paddles 606 and a pair of gripping clasps 608, it should be understood that the implantable device 602 can include any suitable number of paddles and gripping clasps, and the paddles and gripping clasps can be in any configuration.

Figure 36:
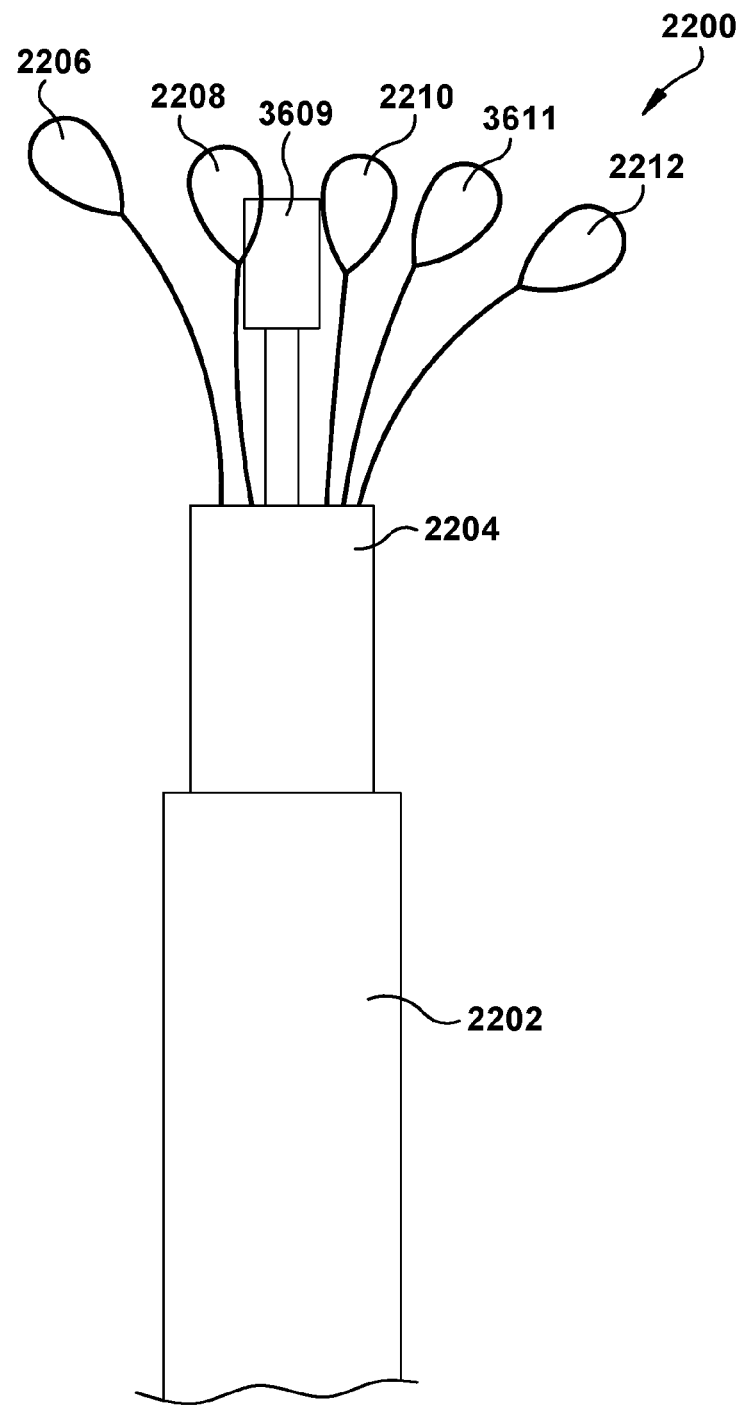
FIG. 36 shows an example embodiment of a retrieval device for retrieving an implanted prosthetic device from a native valve.

Referring to FIG. 36, an example retrieval device 2200 is shown that is configured to remove and retrieve a device that was previously implanted within a patient's native valve (e.g., implanted device 602 shown in FIG. 35). The previously implanted device can be retrieved after it has been implanted for various periods of time. In some embodiments, the retrieval device 2200 can be used to retrieve a device 602 that has been implanted within a patient's native valve for one month or less, such as 30 days or less, such as 25 days or less, such as 20 days or less, such as 15 days or less, such as 10 days or less, such as seven days or less, such as six days or less, such as five days or less, such as four days or less, such as three days or less, such as two days or less, such as one day or less, such as 20 hours or less, such as 15 hours or less, such as 10 hours or less, such as five hours or less, such as one hour or less, such as 30 minutes or less, such as 10 minutes or less, such as 5 minutes or less, such as one minute or less. In some embodiments, the retrieval device 2200 can be used to retrieve a device 602 that has been implanted within a patient's native valve for more than one month. While the retrieval device is described as retrieving the implanted device 602, it should be understood that the retrieval device 2200 can be used to retrieve any suitable type of device that is implanted within a native valve of a patient.

The example retrieval device 2200 includes a catheter 2202 that is configured to position the retrieval device 2200 to engage the implanted device 602, a retrieval shaft 2204, and one or more retrieval components (2206, 2208, 2210, 2212, 3609, 3611) housed within the retrieval shaft 2204. The one or more retrieval components (2206, 2208, 2210, 2212, 3609, 3611) are configured to engage the implanted device 602 to remove the implanted device from the valve tissue 802. In the illustrated embodiment, the one or more components include a first securing member 2208, a second securing member 3609, a first actuation member 2210, a second actuation member 3611, and one or more capturing members (2206, 2212). The first and second actuation members 2210, 3611 can take any suitable form, such as, for example, a wire with a loop, a clip, a magnet, a detent mechanism, a coupler, a hook and loop connection, any frictional connection, a twist to lock type connection, any other known fastening arrangement, or any form described with respect to other actuation members/elements anywhere herein.

The first and second securing members 2208, 3609 can take any suitable form, such as, for example, a shaft, a wire with a loop, a clip, a magnet, a detent mechanism, a coupler, a hook and loop connection, any frictional connection, a twist to lock type connection, any other known fastening arrangement, or any form described with respect to other securing members anywhere herein. In some embodiments, the first securing member 2208 can take the form of the securing member 2208 shown in FIGS. 43-49.

The one or more capturing members (2206, 2212) can take any suitable form, such as, for example, a wire with a loop, a clip, a magnet, a detent mechanism, a coupler, a hook and loop connection, any frictional connection, a twist to lock type connection, any other known fastening arrangement, or any form described with respect to other capturing members anywhere herein. In some embodiments, the retrieval device 2200 can include a capturing member that takes the form of the capturing member 2206 shown in FIGS. 39-49.

The one or more retrieval components (2206, 2208, 2210, 2212, 3609, 3611) can be disposed in one or more lumens or bores of the retrieval shaft 2204 (e.g., the lumens 2214, 2216, 2218 shown in FIG. 23). For example, all of the components (2206, 2208, 2210, 2212, 3609, 3611) can be disposed in a single lumen, each of the components can be disposed in a lumen by itself, or any other suitable number of lumens can be used to house the components.

Figure 37:
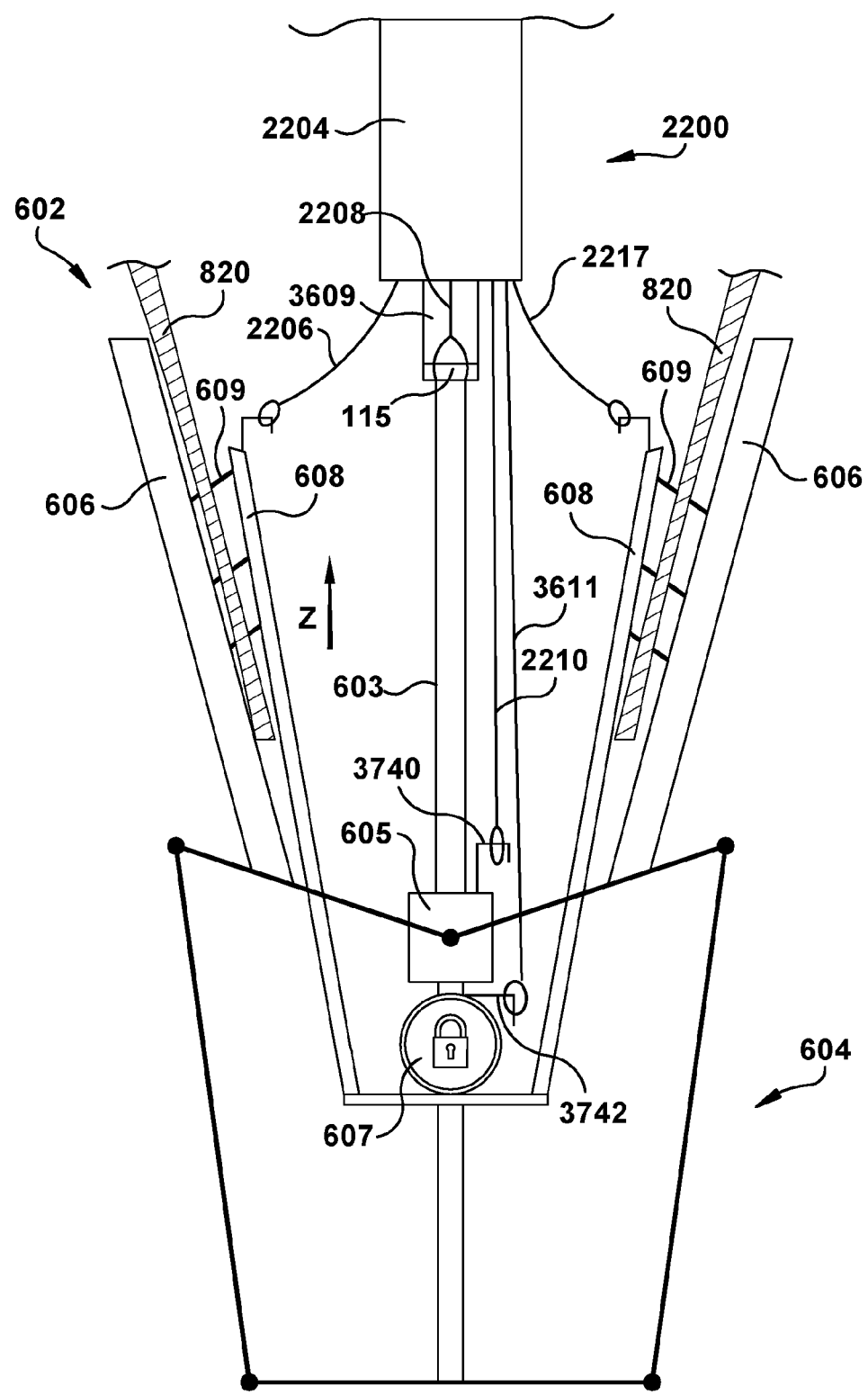
FIG. 37 shows the example retrieval device of FIG. 36 engaging the implanted prosthetic device of FIG. 35 to remove the implanted prosthetic device from the native valve.
Figure 38:
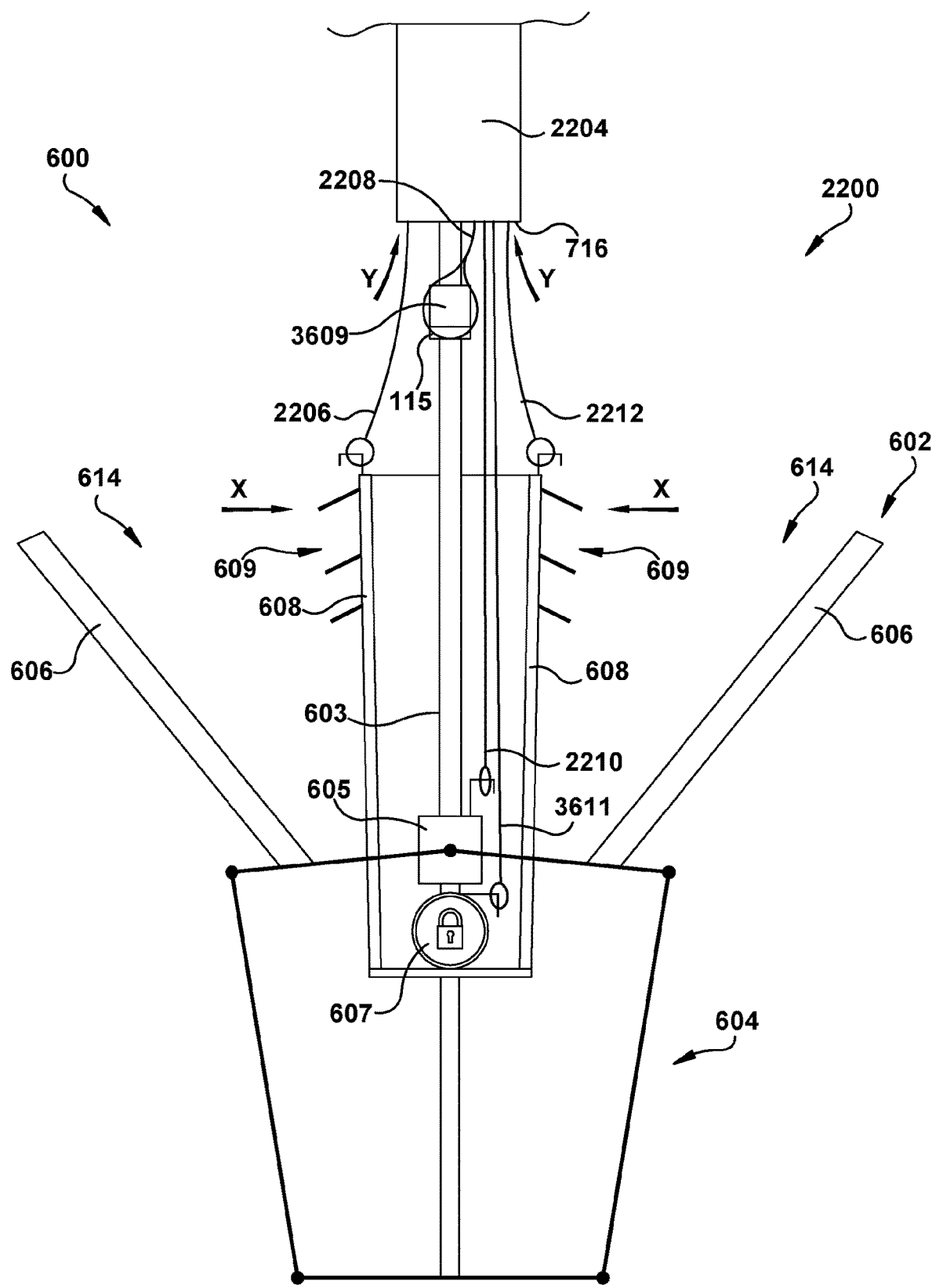
FIG. 38 shows the example retrieval device of FIG. 36 attached to the implantable prosthetic device of FIG. 35 after the implantable prosthetic device has been removed from the native valve.

Referring to FIGS. 37 and 38, the retrieval device 2200 is shown engaging the implanted device 602 to remove the implanted device from the valve tissue 820. Referring to FIG. 37, the securing member 2208 is configured to attach to a collar 115 or another portion of the shaft 603 of the implanted device 602. In the illustrated embodiment, the securing member 2208 is a wire with a loop that attaches to the collar 115 such that the retrieval device 2200 is properly positioned relative to the implanted device 602. After the retrieval device 2200 is properly positioned, the securing member 3609 can be used to attach the retrieval device 2200 to the shaft 603 of the implanted device 602. In the illustrated embodiment, the securing member 3609 is a shaft that is connectable to the shaft 603 of the implanted device 602. The securing member 3609 can be connected to the shaft 603 by a threaded connection, a snap fit connection, a frictional connection, a magnetic connection, a twist and lock type connection, or any other suitable connection.

Still referring to FIG. 37, after the retrieval device 2200 is secured to the implanted device 602 by the securing members 2208, 3609, the actuation members/elements 2210, 3611 and the capturing members 2206, 2212 can be used to engage the implanted device 602. The first actuation member 2210 is configured to engage the coupler 605 of the implanted device 602. In the illustrated embodiment, the first actuation member 2210 is a wire with a loop, and the coupler has an attachment member 3740. The attachment member 3740 can be, for example, a hook, a loop, a magnet, hook or loop connection material, or any other arrangement that facilitates attachment of the first actuation member 2210. In some embodiments, the wire loop of the first actuation member 2210 is configured to connect to the attachment member 3740 (e.g., hook) of the coupler 605.

The second actuation member/element 3611 is configured to engage the lock 607 of the implanted device 602. In the illustrated embodiment, the second actuation member 3611 is a wire with a loop, and the coupler has an attachment member 3742. The attachment member 3742 can be, for example, a hook, a loop, a magnet, hook or loop connection material, any form described with respect to other attachment members anywhere herein, or any other arrangement that facilitates attachment of the second actuation member 3611. In some embodiments, the wire loop of the first actuation member 2210 is configured to connect to the attachment member 3740 (e.g., hook) of the coupler 605. The lock 607 serves as a locking means for locking the coupler 605 in a stationary position with respect to the shaft 603 and can take a wide variety of different forms. In one embodiment, the lock 607 takes the form of locks often used in caulk guns. That is, the lock 607 includes a pivotable plate having a hole, in which the shaft 603 is disposed within the hole of the pivotable plate. In this embodiment, when the pivotable plate is in the tilted position, the pivotable plate engages the shaft 603 to maintain a position on the shaft 603, but, when the pivotable plate is in a substantially non-tilted position, the pivotable plate can be moved along the shaft (which allows the coupler 605 to move along the shaft 603). In other words, the coupler 605 is prevented from moving along the shaft 603 when the pivotable plate of the lock 607 is in a tilted (or locked) position, and the coupler is allowed to move along the shaft 603 when the pivotable plate is in a substantially non-tilted (or unlocked) position. In embodiments in which the lock 607 includes a pivotable plate, the attachment member 3742 is attached to the pivotable plate and engaging the attachment member 3742 with the actuation member 3611 can cause the pivotable plate to move the plate between the tilted and substantially non-tilted positions. In certain embodiments, the pivotable plate of the lock 607 is biased in the tilted (or locked) position, and the actuation member 3611 is used to move the plate from the tilted position to the substantially non-tilted (or unlocked) position. The lock 607, however, can take any other suitable form that is capable of being unlocked by the actuation member 3611.

The capturing members 2206, 2212 are configured to attach to the gripping clasps 608 to remove the gripping clasps from engagement with the valve tissue 820. In the illustrated embodiment the capturing members 2206, 2212 are wires with a loop, and each of the gripping clasps 608 has an attachment member 3726. The attachment member 3726 can be, for example, a hook, a loop, a magnet, hook or loop connection material, or any other arrangement that facilitates attachment of the capturing members 2206, 2212. In some embodiments, the wire loop of the capturing members 2206, 2212 are configured to connect to the attachment member 3740 (e.g., hook) of the gripping clasps 608.

Referring to FIGS. 37 and 38, the paddles 606 of the implanted device 602 are removed from the valve tissue 820 by moving the paddles 606 from the closed position (as shown in FIG. 37) to the open position (as shown in FIG. 38). After the retrieval device 2200 is secured to the implanted device 602 by the securing members 2208, 3609, the actuation member 3611 is used (e.g., retracted) to unlock the lock 607, which allows the coupler 605 to move along the shaft 603. The actuation member 2210 is used to move the unlocked coupler 605 in the direction Z, which cause the paddles 606 to move from the closed position to the open position.

Referring to FIG. 38, after the paddles 606 are in the open position, the capturing members 2206, 2212 are moved in the direction Y, which causes the gripping clasps 608 to move in the direction X. This movement of the gripping clasps 608 in the direction X causes the gripping clasps 608 to be removed from the valve tissue 820 (FIG. 37). After the paddles 606 are opened and the gripping clasps 608 are removed from the valve tissue 820, the implanted device is no longer engaging the valve tissue 820. The retrieval shaft 2204 and the device 602 can be retracted into the catheter 2202. The catheter 2202 containing the device 602 can then be removed from the patient's body.

While various inventive aspects, concepts and features of the disclosures may be described and illustrated herein as embodied in combination in the example embodiments, these various aspects, concepts, and features may be used in many additional embodiments, either individually or in various combinations and sub-combinations thereof. Unless expressly excluded herein all such combinations and sub-combinations are intended to be within the scope of the present application. Still further, while various additional embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available embodiments, whether presently known or later developed. Those skilled in the art may readily adopt one or more of the inventive aspects, concepts, or features into additional embodiments and uses within the scope of the present application even if such embodiments are not expressly disclosed herein. Further, the treatment techniques, methods, operations, steps, etc. described or suggested herein can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

The invention claimed is:
1. An assembly, comprising:
  a retrieval device for retrieving a previously implanted valve repair device on leaflets of a native valve;
  the previously implanted valve repair device comprising:
    an anchor portion comprising a pair of paddles;
    a spacer coupled to and disposed between the pair of paddles;

wherein the spacer is configured to block blood flow through the spacer;
a collar disposed at a proximal end of the spacer;
the retrieval device comprising:
a catheter;
a retrieval shaft disposed within the catheter;
wherein the retrieval shaft is configured to be extended from the catheter;
one or more retrieval components coupled to the retrieval shaft, the one or more retrieval components comprising:
at least one securing member selected from the group consisting of a wire loop, a snare, a lasso, a ring, a hoop, a clip, a magnet, a detent mechanism, and a coupler;
wherein the securing member becomes attached to the collar while the previously implanted device is implanted on the leaflets of the native valve;
at least one actuation member selected from the group consisting of a rod, a shaft, a bar, a wire, a line, a hook, and a suture;
wherein the actuation member becomes engaged with the anchor portion while the previously implanted device is implanted on the leaflets of the native valve; and
wherein the securing member and the actuation member are configured such that moving the actuation member relative to the securing member moves the pair of paddles of the anchor portion of the previously implanted device from a closed configuration to an open configuration.

2. The assembly according to claim 1, wherein the actuation member engages a cap of the previously implanted device to move the pair of paddles from the closed configuration to the open configuration.

3. The assembly according to claim 1, wherein the previously implanted device includes a pair of gripping clasps that secure the previously implanted device to the native valve.

4. The assembly according to claim 3, further comprising at least one capturing member that engages the pair of gripping clasps of the previously implanted device while the previously implanted device is implanted on the leaflets of the native valve to remove the pair of gripping clasps from the native valve, wherein the at least one capturing member is selected from the group consisting of a wire, a wire loop, a wire with a barb, a snare, a lasso, a hook, a tether, a line, a ring, and a hoop.

5. The assembly according to claim 4, wherein the at least one capturing member comprises a first capturing member configured to engage a first gripping clasp of the pair of gripping clasps and a second capturing member configured to engage a second gripping clasp of the pair of gripping clasps.

6. The assembly according to claim 4, wherein the at least one capturing member comprises a wire with a loop, and wherein the at least one capturing member is configured to attach to an attachment member of each of the pair of gripping clasps.

7. The assembly according to claim 6, wherein the attachment member comprises a hook.

8. The assembly according to claim 1, wherein the securing member comprises a wire with a loop.

9. The assembly according to claim 1, wherein the one or more retrieval components further comprise a second securing member for attaching the retrieval device to the previously implanted device.

\* \* \* \* \*